(12) United States Patent
Rozema et al.

(10) Patent No.: US 12,116,573 B2
(45) Date of Patent: Oct. 15, 2024

(54) TARGETING LIGANDS FOR THERAPEUTIC COMPOUNDS

(71) Applicant: Arrowhead Pharmaceuticals, Inc., Pasadena, CA (US)

(72) Inventors: David B. Rozema, Middleton, WI (US); Darren H. Wakefield, Fitchburg, WI (US); Andrei V. Blokhin, Fitchburg, WI (US); Jonathan D. Benson, Madison, WI (US); Zhen Li, Westfield, NJ (US); Tao Pei, Monona, WI (US); Fred Fleitz, Pasadena, CA (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 308 days.

(21) Appl. No.: 17/184,575

(22) Filed: Feb. 24, 2021

(65) Prior Publication Data
US 2021/0189394 A1 Jun. 24, 2021

Related U.S. Application Data

(63) Continuation of application No. 16/363,108, filed on Mar. 25, 2019, now abandoned, which is a continuation of application No. 15/452,423, filed on Mar. 7, 2017, now Pat. No. 10,246,709.

(60) Provisional application No. 62/426,916, filed on Nov. 28, 2016, provisional application No. 62/370,754, filed on Aug. 4, 2016, provisional application No. 62/304,652, filed on Mar. 7, 2016.

(51) Int. Cl.
*C12N 15/113* (2010.01)
*A61K 31/713* (2006.01)
*A61K 47/54* (2017.01)
*C07H 15/04* (2006.01)

(52) U.S. Cl.
CPC .......... *C12N 15/113* (2013.01); *A61K 31/713* (2013.01); *A61K 47/549* (2017.08); *C07H 15/04* (2013.01); *C12N 2310/14* (2013.01); *C12N 2310/317* (2013.01); *C12N 2310/32* (2013.01); *C12N 2310/321* (2013.01); *C12N 2310/322* (2013.01); *C12N 2310/351* (2013.01); *C12N 2310/3515* (2013.01)

(58) Field of Classification Search
CPC .............. C12N 15/113; C12N 2310/14; C12N 2310/32; C12N 2310/321; C12N 2310/322; C12N 2310/351; C12N 2310/3515; A61K 31/713; A61K 47/549
USPC ........................................................ 536/17
See application file for complete search history.

(56) References Cited

U.S. PATENT DOCUMENTS

| | | | |
|---|---|---|---|
| 4,469,863 | A | 9/1984 | Ts'o et al. |
| 4,751,219 | A | 6/1988 | Kempen |
| 5,885,968 | A | 3/1999 | Biessen et al. |
| 5,994,517 | A | 11/1999 | Ts'o et al. |
| 5,998,203 | A | 12/1999 | Matulic-Adamic |
| 6,300,319 | B1 | 10/2001 | Manoharan |
| 6,383,812 | B1 | 5/2002 | Chen et al. |
| 6,525,031 | B2 | 2/2003 | Manoharan |
| 6,620,916 | B1 | 9/2003 | Takahara et al. |
| 6,660,720 | B2 | 12/2003 | Manoharan |
| 6,906,182 | B2 | 6/2005 | Ts'o et al. |
| 6,908,903 | B1 | 6/2005 | Theodore et al. |
| 7,041,818 | B2 | 5/2006 | Susaki et al. |
| 7,109,165 | B2 | 9/2006 | Matulic-Adamic et al. |
| 7,262,177 | B2 | 8/2007 | Ts'o et al. |
| 7,439,043 | B2 | 10/2008 | DeFrees et al. |
| 7,491,805 | B2 | 2/2009 | Vargeese et al. |
| 7,582,744 | B2 | 9/2009 | Manoharan et al. |
| 7,723,509 | B2 | 5/2010 | Manoharan et al. |

(Continued)

FOREIGN PATENT DOCUMENTS

| | | |
|---|---|---|
| EP | 3023495 | 5/2019 |
| WO | 199720563 | 6/1997 |

(Continued)

OTHER PUBLICATIONS

Lee et al., "New and More Efficient Multivalent glyco-ligands for asialoglycoprotein receptor of mammalian hepatocytes" Bioorganic & Medicinal Chemistry; 19: 2494-2500; (2011).

(Continued)

*Primary Examiner* — Yih-Horng Shiao
*Assistant Examiner* — Jaret J Crews
(74) *Attorney, Agent, or Firm* — Honigman LLP; Andrew N. Weber; Jonathan P. O'Brien

(57) ABSTRACT

Described are novel targeting ligands that may be linked to compounds, such therapeutic compounds, that are useful in directing the compounds to the target in vivo. The targeting ligands disclosed herein can serve to target expression-inhibiting oligomeric compounds, such as RNAi agents, to liver cells to modulate gene expression. The targeting ligands disclosed herein, when conjugated to an expression-inhibiting oligomeric compound, may be used in a variety of applications, including use in therapeutic, diagnostic, target validation, and genomic discovery applications. Compositions including the targeting ligands disclosed herein when linked to expression-inhibiting oligomeric compounds are capable of mediating expression of target nucleic acid sequences in liver cells, such as hepatocytes, which may be useful in the treatment of diseases or conditions that respond to inhibition of gene expression or activity in a cell, tissue, or organism.

3 Claims, 16 Drawing Sheets

Specification includes a Sequence Listing.

(56) References Cited

U.S. PATENT DOCUMENTS

| | | | |
|---|---|---|---|
| 7,833,992 B2 | 11/2010 | Vargeese et al. | |
| 7,851,615 B2 | 12/2010 | Manoharan et al. | |
| 7,964,578 B2 | 6/2011 | Vargeese et al. | |
| 8,106,022 B2 | 1/2012 | Manoharan et al. | |
| 8,137,695 B2 | 3/2012 | Rozema et al. | |
| 8,158,601 B2 | 4/2012 | Chen et al. | |
| 8,313,772 B2 | 11/2012 | Rozema et al. | |
| 8,344,125 B2 | 1/2013 | Manoharan et al. | |
| 8,349,308 B2 | 1/2013 | Yurkovetskiy et al. | |
| 8,404,862 B2 | 3/2013 | Manoharan et al. | |
| 8,426,377 B2 | 4/2013 | Manoharan et al. | |
| 8,435,491 B2 | 5/2013 | Wang et al. | |
| 8,450,467 B2 | 5/2013 | Manoharan et al. | |
| 8,501,930 B2 * | 8/2013 | Rozema | A61K 47/549 530/300 |
| 8,541,548 B2 | 9/2013 | Rozema | |
| 8,552,163 B2 | 10/2013 | Lee et al. | |
| 8,828,956 B2 | 9/2014 | Manohanan et al. | |
| 8,877,917 B2 | 11/2014 | Forst et al. | |
| 9,127,276 B2 | 9/2015 | Prakash et al. | |
| 9,181,549 B2 | 11/2015 | Prakash et al. | |
| 9,290,760 B2 | 3/2016 | Rajeev et al. | |
| 9,309,513 B2 | 4/2016 | Bhat et al. | |
| 9,352,048 B2 | 4/2016 | Bhat et al. | |
| 9,540,639 B2 | 1/2017 | Tellers et al. | |
| 9,803,205 B2 | 10/2017 | Kanner et al. | |
| 9,932,586 B2 * | 4/2018 | Melquist | C12N 15/1137 |
| 10,246,709 B2 * | 4/2019 | Rozema | A61K 31/713 |
| 10,294,474 B2 | 5/2019 | Li et al. | |
| 10,308,941 B2 | 6/2019 | Kanner et al. | |
| 10,450,565 B2 | 10/2019 | Li et al. | |
| 2002/0086356 A1 | 7/2002 | Tuschl et al. | |
| 2003/0119724 A1 | 6/2003 | Ts'o et al. | |
| 2003/0143732 A1 | 7/2003 | Fosnaugh et al. | |
| 2003/0148928 A1 | 8/2003 | Beigelman et al. | |
| 2004/0110296 A1 | 6/2004 | Vargeese et al. | |
| 2004/0259247 A1 | 12/2004 | Tuschl et al. | |
| 2005/0164235 A1 | 7/2005 | Manoharan et al. | |
| 2006/0148740 A1 | 7/2006 | Platenburg | |
| 2006/0183886 A1 | 8/2006 | Ts'o et al. | |
| 2008/0108801 A1 | 5/2008 | Manoharan et al. | |
| 2008/0206869 A1 | 8/2008 | Smith et al. | |
| 2008/0281041 A1 | 11/2008 | Rozema et al. | |
| 2008/0281044 A1 | 11/2008 | Monahan et al. | |
| 2009/0203135 A1 | 8/2009 | Forst et al. | |
| 2009/0239814 A1 | 9/2009 | Manoharan et al. | |
| 2009/0286973 A1 | 11/2009 | Manoharan et al. | |
| 2010/0240730 A1 | 9/2010 | Beigelman et al. | |
| 2011/0077386 A1 | 3/2011 | Lee et al. | |
| 2011/0097264 A1 | 4/2011 | Wang et al. | |
| 2011/0123520 A1 | 5/2011 | Manoharan et al. | |
| 2011/0201798 A1 | 8/2011 | Manoharan | |
| 2011/0207799 A1 | 8/2011 | Rozema et al. | |
| 2011/0269814 A1 | 11/2011 | Manoharan et al. | |
| 2012/0035115 A1 | 2/2012 | Manoharan et al. | |
| 2012/0095075 A1 | 4/2012 | Manoharan et al. | |
| 2012/0128760 A1 | 5/2012 | Manoharan et al. | |
| 2012/0136042 A1 | 5/2012 | Manoharan et al. | |
| 2012/0157509 A1 | 6/2012 | Hadwiger et al. | |
| 2012/0165393 A1 | 6/2012 | Rozema et al. | |
| 2012/0183602 A1 | 7/2012 | Chen et al. | |
| 2012/0225927 A1 | 9/2012 | Sah et al. | |
| 2012/0230938 A1 | 9/2012 | Rozema et al. | |
| 2013/0004427 A1 | 1/2013 | El-sayed et al. | |
| 2013/0035366 A1 | 2/2013 | Swayze et al. | |
| 2013/0121954 A1 | 5/2013 | Wakefield et al. | |
| 2013/0178512 A1 | 9/2013 | Manoharan et al. | |
| 2013/0236968 A1 | 9/2013 | Manoharan et al. | |
| 2013/0317079 A1 * | 11/2013 | Wakefield | A61K 47/32 525/330.3 |
| 2015/0018540 A1 | 1/2015 | Prakash et al. | |
| 2015/0065558 A1 | 3/2015 | Forst et al. | |
| 2015/0246133 A1 | 9/2015 | Tellers et al. | |
| 2015/0361427 A1 | 12/2015 | Wooddell et al. | |
| 2015/0368642 A1 | 12/2015 | Albaek et al. | |
| 2016/0017323 A1 | 1/2016 | Prakash et al. | |
| 2016/0078088 A1 | 3/2016 | Venkatesh et al. | |
| 2016/0102120 A1 | 4/2016 | Hadwiger et al. | |
| 2016/0272970 A1 | 9/2016 | Rozema et al. | |
| 2017/0035796 A1 | 2/2017 | Wooddell et al. | |
| 2017/0096665 A1 | 4/2017 | Melquist et al. | |
| 2017/0253875 A1 | 9/2017 | Rozema et al. | |
| 2018/0064819 A1 | 3/2018 | Li et al. | |
| 2019/0211333 A1 | 7/2019 | Rozema et al. | |
| 2019/0256849 A1 | 8/2019 | Li et al. | |

FOREIGN PATENT DOCUMENTS

| | | |
|---|---|---|
| WO | 199720563 A1 | 6/1997 |
| WO | 199746098 | 12/1997 |
| WO | 199746098 A1 | 12/1997 |
| WO | 199965925 | 12/1999 |
| WO | 199965925 A1 | 12/1999 |
| WO | 2002043771 | 6/2002 |
| WO | 2002043771 A2 | 6/2002 |
| WO | 2002085908 | 10/2002 |
| WO | 2002085908 A1 | 10/2002 |
| WO | 2002094185 | 11/2002 |
| WO | 2002094185 A2 | 11/2002 |
| WO | 2004024757 | 3/2004 |
| WO | 2004024757 A2 | 3/2004 |
| WO | 2004080406 | 9/2004 |
| WO | 2004080406 A2 | 9/2004 |
| WO | 2004090108 | 10/2004 |
| WO | 2004090108 A2 | 10/2004 |
| WO | 2004094595 | 11/2004 |
| WO | 2004094595 A2 | 11/2004 |
| WO | 2004101619 | 11/2004 |
| WO | 2004101619 A1 | 11/2004 |
| WO | 2006020768 | 2/2006 |
| WO | 2006020768 A2 | 2/2006 |
| WO | 2006031461 | 3/2006 |
| WO | 2006031461 A2 | 3/2006 |
| WO | 2008098788 | 8/2008 |
| WO | 2008098788 A2 | 8/2008 |
| WO | 2009073809 | 6/2009 |
| WO | 2009073809 A2 | 6/2009 |
| WO | 2009082606 | 7/2009 |
| WO | 2009082606 A2 | 7/2009 |
| WO | 2009126933 | 10/2009 |
| WO | 2009126933 A2 | 10/2009 |
| WO | 2009134487 | 11/2009 |
| WO | 2009134487 A2 | 11/2009 |
| WO | 2010048585 | 4/2010 |
| WO | 2010048585 A2 | 4/2010 |
| WO | 2011038356 | 3/2011 |
| WO | 2011038356 A2 | 3/2011 |
| WO | 2012037254 | 3/2012 |
| WO | 2012037254 A1 | 3/2012 |
| WO | 2012083046 | 6/2012 |
| WO | 2012083046 A2 | 6/2012 |
| WO | 2012083185 | 6/2012 |
| WO | 2012083185 A2 | 6/2012 |
| WO | 2012089352 | 7/2012 |
| WO | 2012089352 A1 | 7/2012 |
| WO | 2012089602 | 7/2012 |
| WO | 2012089602 A1 | 7/2012 |
| WO | 2013033230 | 3/2013 |
| WO | 2013033230 A1 | 3/2013 |
| WO | 2013165816 | 11/2013 |
| WO | 2013165816 A2 | 11/2013 |
| WO | 2013166121 | 11/2013 |
| WO | 2013166121 A1 | 11/2013 |
| WO | 2014025805 | 2/2014 |
| WO | 2014025805 A1 | 2/2014 |
| WO | 2014076195 | 5/2014 |
| WO | 2014076195 A1 | 5/2014 |
| WO | 2014076196 | 5/2014 |
| WO | 2014076196 A1 | 5/2014 |
| WO | 2014118267 | 8/2014 |
| WO | 2014118267 A1 | 8/2014 |
| WO | 2014118272 | 8/2014 |
| WO | 2014118272 A1 | 8/2014 |
| WO | 2014179620 | 11/2014 |

(56) References Cited

FOREIGN PATENT DOCUMENTS

| WO | 2014179620 A1 | 11/2014 |
|---|---|---|
| WO | 2014179627 | 11/2014 |
| WO | 2014179627 A2 | 11/2014 |
| WO | 2014179629 | 11/2014 |
| WO | 2014179629 A2 | 11/2014 |
| WO | 2015006740 | 1/2015 |
| WO | 2015006740 A2 | 1/2015 |
| WO | 2015069587 | 5/2015 |
| WO | 2015069587 A2 | 5/2015 |
| WO | 2015168618 | 11/2015 |
| WO | 2015168618 A2 | 11/2015 |
| WO | 2015188194 | 12/2015 |
| WO | 2015188194 A1 | 12/2015 |
| WO | 2016055601 | 4/2016 |
| WO | 2016055601 A1 | 4/2016 |
| WO | 2018/132432 | 1/2018 |
| WO | 2018/044350 | 3/2018 |
| WO | 2018/140920 | 8/2018 |
| WO | 2016/149020 | 9/2018 |

OTHER PUBLICATIONS

Kornilova et al.; "Development of a fluorescence poloarization binding assay for asialoglycoprotein receptor" Analytical Biochemistry; 425; 43-46; (2012).
Lee et al., "Synthesis of multivalent neoglyconjugates of MUCI by the conjurgation of carobhydratecentered, triazole-linked glycoclusters to MUCI peptides using click chemistry." J. Org Chem; 77: 7564-7571; (2012).
Liang et al., "Hepatitis Be Antigen—The Dangerous Endgame of Hepatitis B" N. Engl J Med.; 347: 208-210; (2012).
Pujol et al., "A Sulfur Tripod Glycoconjugate that Releases a High-Affinity Copper Chelator in Hepatocytes" Angew. Chem. Int. Ed.; 51: 7445-7448; (2012).
Kanasty et al.; "Delivery Materials for siRNA Therapeutics" Nature Materials; 12: 967-977; (2013).
Tober et al., "Self-Metathesis of Polyol Allyl Ethers towards Carbohydrate-Based Oligohydroxy Derivatives" Eur. J. Org. Chem.; 3: 566-577; (2013).
Ming et al., "Bioconjugates for Targeted Delivery of Therapeutic Oligonucleotides" Advanced Drug Delivery Review (2015) vol. 87, pp. 81-89 (2015).
Riedi et al., "Targeting the Eph System with Peptides and Peptide Conjugates" Current Drug Targets (2015) vol. 16, No. 10, pp. 1031-1047 (2015).
Zhu et al., "Aptamer-Drug Conjugates" Bioconjugate Chemistry (2015) vol. 26, No. 11, pp. 2186-2197 (2015).
Alnylam; RNAi Roundtable: Advances in Delivery of RNAi Therapeutics with Enhanced Stabilization Chemsitry (ESC)-GalNAc-siRNA Conjugates; (Jul. 22, 2014).
Nair et al. "Multivalent N-Acetylgalactosamine-conjugated siRNA Localizes in Hepatocytes and Elicits Robust RNAi-Mediated Gene Silencing", Journal of the American Chemical Society, vol. 136, No. 49, Dec. 10, 2014.
International Search Report and Written Opinion for corresponding International Application No. PCT/US17/21147.
International Search Report and Written Opinion for corresponding International Application No. PCT/US17/21175.
Jayaprakash, K. Nair et al.; "Multivalent N-Acetylgalactosamine Conjugated siRNA Localizes in Hepatocytes and Elicits Robust RNAiMediated Gene Silencing" Journal of The American Chemical Society; 136(49); 16958-16961; (Dec. 2014).
Connolly et al.; "Binding and Endocytosis of Cluster Glycosides by Rabbin Hepatocytes"; J. Biol. Chem; 257 (2):939-945; (1982).
Lee et al., "New Synthetic cluster ligands for galactose/N-acetylgalactosamine-specific lectin of mammalian liver" Biochem; 23: 4255-4261; (1984).
Lee et al., "Preparation of Cluster Glycosides of N-acetylgalactosamine That Have Subnanomolar Binding Constants Towards the Mammalian Hepatic Gal/GalNAc-specific Receptor" Glycoconjugate J.; 4: 317-328; (1987).
Englisch et al.; "Chemically Modified Oligonucleotides as Probes and Inhibitors" Agnew Chem. Int. Ed. Engl.; 30: 613-629; (1991).
Manoharan et al., "Introduction of a lipophilic thioether tether in the minor groove of nucleic acids for antisense applications" Bioorg. Med. Chem. Lett.; 4: 1053-1060; (1993).
Manoharan et al., "Cholic Acid-Oligonucleotide Conjugates for Antisense Applications" Bioorg. Med. Chem. Lett.: 4: 1053-1060; (1994).
Merwin et al., "Targeted delivery of DNA using YEE(GalNAcAH)3, a synthetic glycopeptide ligand for the asialoglycoprotein receptor." bioconjug Chem; 5(6): 612-620; (1994).
Biessen et al. "Synthesis of Cluster Galactosides with High Affinity for the Hepatic Asialoglycoprotein Receptor" Journal of Medicinal Chemistry; 38(9): 1538-1546; (1995).
Biessen et al.; "The Cholesterol Derivative of a Triantennary Galactoside with High Affinity for Hepatic Asialoglycoprotein Receptor: A Potent Cholesterol Lowering Agent"; J. Med. Chem; 38(11): 1846-1852; (1995).
Manoharan et al., "Lipidic Nucleic Acids" Tetrahedron Lett.; 36(21): 3651-3654; (1995).
Manoharan et al., "Oligonucleotide Conjugates: Alteration of the Pharmacokinetic Properties of Antisense Agents" Nucleosides & Nucleotides: 14 (3-5: 969-973; (1995).
Iobst ST et al.; "Selective Sugar Binding to the Carbohydrate Recognition Domains of the Rat Hepatic and Macrophage Asialoglycoprotein Receptors." Journal of Biological Chemistry; 271(12), p. 6686-6693; (1996).
Lee et al.; "Facile Synthesis of a High-Affinity Ligand for Mammalian Hepatic Lectin Containing Three Terminal N-Acetylgalactosamine Residues" Bioconjugate Chem.; 8: 762-765; (1997).
Murata et al.; "Design of Quaternary Chitosan Conjugate having Antennary Galactose Residues as a Gene Delivery Tool"; Carbohyd. Polym.; 32(2): 105-109; (1997).
Rajur et al., "Covalent Protein-Oligonucleotide Conjugates for Efficient Delivery of Antisense Molecules" Bioconjugate Chem.; 8: 935-940; (1997).
Vaino et al.; "Synthesis of a D-Lactosyl Cluster-Nucleoside Conjugate"; Chem. Commun.; 19: 1871-1872; (1997).
Valentijn et al., "Solid-phase synthesis of lysine-based cluster galactosides with High Affinity for the Asialoglycoprotein Receptor" Tetrahedron; 53(2); 759-770; (1997).
Crossman et al. "Synthesis of Some Second-Generation Substrate Analogues of Early Intermediates in the Biosynthetic Pathway of Glycosylphosphatidylinositol Membrane Anchors"; Carbohyd. Res.; 321 (1-2): 42-51; (1999).
Sliedregt et al.; "Design and Synthesis of Novel Amphiphilic Dendritic Galactosides for Selective Targeting of Liposomes to the Hepatic Asialoglycoprotein Receptor"; J. Med. Chem.; 42(4): 609-618; (1999).
Elbashir et al.; Duplexes of 21-nucleotide RNAs mediate RNA interference in cultured mammalian cells; Nature; 411: 494-498; (2001).
Kato et al., "N-acetylgalactosamine incorporation into a peptide containing consecutive threonine residues by UDP-N-acetyl-D-galactosaminide:polypeptide N-acetylgalactosaminyltransferases" Glyobiology: 11: 821-829; (2001).
Liu et al.; "Targeted Drug Deligery to Chemoresistant Cells: Folic Acid Derivatization of FdUMP [10] Enhances Cytotoxicity Toward 5-FU-Resistant Human Colorector Tumor Cells"; J. Org. Chem.; 66(17): 5655-5663; (2001).
Rensen et al.; "Determination of the Upper Size Limit for Uptake and Processing of Ligands by the Asialoglycoprotein Receptor on Hepatocytes in Vitro and in Vivio" J. biol. Chem.; 276(40): 37577-37584; (2001).
Chen et al., Synthesis of Antisense Oligonucleotide-Peptide Conjugate Targeting GLUT-1 in HepG-2 and MCF-7 Cells Bioconjugate Chemistry (2002) vol. 13, pp. 525-529 (20020.
Chiu et al.; "RNAi in Human Cells: Basic Structural and Functional Features of Small Interfering RNA"; Mol. Cell; 10: 549-561; (2002).

(56) References Cited

OTHER PUBLICATIONS

Coltart et al.; "Principles of Mucin Architecture: Structural Studies on Synthetic Clycopeptides Bearing Clustered Mono-, Di-, Tri-, and Hexasaccharide Clycodomains"; J. Am. Chem. Soc.; 124: 9833-9844; (2002).
Manoharan, "Oligonucleotide Conjugates as Potential Antisense Drugs with Improved Uptake, Biodistribution, Targeted Delivery, and Mechanism of Action" Antisense & Nucleic Acid Drug Development; 12: 103-128; (2002).
Dubber et al.; "Solid-Phase Synthesis of Multivalent Glycoconjugates on a DNA Synthesizer"; Bioconjugate Chem.; 14(1): 239-246; (2003).
Hamzavi et al.; "Modulation of the Pharmacokinetic Properties of PNA: Preparation of Galactosyl, Mannosyl, Fucosl, N-Acetylgalactosaminyl, and N-Acetylglucosaminyl Derivatives of Aminoethylglycine Peptide Nucleic Acid Monomers and Their Incorporation into PNA Oligomers"; Bioconjugate Chem.; 14:941-954; (2003).
Lee et al., "Synthesis of Peptide-Based Trivalent Scaffold for Preparation of Cluster Glycosides" Methods in Enzymology; 362: 38-43; (2003).
Maier et al.; "Synthesis of Antisense Oligonucleotides Conjugated to a Multivalent Carbohydrate Cluster for Cellular Targeting"; Bioconjugate Chem.; 14: 18-29; (2003).
Zheng et al.; "Distribution and Anti-HBV Effects of Antisense Oligodeoxynucleotides Conjugated to Galactosylated Poly-L-Lysine"; World J. Gastroentero 9(6): 1251-1255; (2003).
Andre et al.; "Determination of modulation of ligand properties of synthetic complex-type biantennary N-glycans by introduction of bisecting GlcNAc in silico, in vitro and in vivo"; Cur. J. Biochem.; 271:118-134; (2004).
Katajisto et al.; "Solid-Phase Synthesis of Multiantennary Oligonucleotide Glycoconjugates Utilizing On-Support Oximation"; Bioconjurage Chem.; 15(4): 890-896; (2004).
Katajisto et al.; Solid-Phase Synthesis of Oligonucleotide Glycoconjugates Bearing Three Different Glycosyl Groups: Orthogonally Protected Bis(hydroxymethyl)-N, N-bis(3-hydroxypropyl)malondiamide Phosphoramidite as Key Building Block. Journal of Organic Chemistry, vol. 69, pp. 7609-7614, 2004.
Rensen et al.; "Design and Synthesis of Novel N-Acetylgalactosamine-Terminated Glycolipids for Targeting of Lipoproteins to the Hepatic Asialoglycoprotein Receptor"; J. Med. Chem.; 47(23): 5798-5808; (2004).
Westerlind et al., "Ligands of the asialoglycoprotein receptor for targeted gene delivery, part 1: Synthesis of and binding studies with biotinylated cluster glycosides containing N-acetylgalactosamine" Glycoconjugate Journal; 21: 227-241; (2004).
Wu et al., "A New N-Acetylgalactosamine Containing Peptide as a Targeting Vehicle for Mammalian Hepatocytes Via Asialoglycoprotein Receptor Endocytosis" Current Drug Delivery; 1: 119-127; (2004).
Zatsepin et al.; "Synthesis and Applications of Oligonucleotide-Carbohydrate Conjugates"; Chem. Biodivers; 1(10): 1401-1417; (2004).
Park et al., "The asialolycoprotein receptor clears glycoconjugates terminating with sialic acid alpha2 6GalNAc" PNAS; 102(47): 17125-17129; (2005).
Guo et al.; "Construction of Folate-Conjugated pRNA of Bateriophase phi29 DNA Packagin Motor for Delivery of Chimeric siRNA to Nasopharyngeal Carcinoma Cells"; Gene Ther.; 13(10): 814-820; (2006).
Ikeda et al.; "Ligand-Targeted Delivery of Therapeutic siRNA"; Pharm. Res.; 23(8): 1631-1640; (2006).
Lee et al., "Protein microarrays to study carobhydrate-recognition events" Bioorg Med Chem Lett; 16(19): 5132-5135; (2006).
Rensen et al., "Stimulation of Liver-Directed Cholesterol Flux in Mice by Novel N-Acetylgalactosamine-Terminated Glycolipids With High Affinity for the Asialoglycoprotein Receptor" Arterioscler Thromb Vase Biol; 26: 169-175; (2006).
Zhang et al. Design of multivalent galactoside ligands and their binding to hepatic asialoglycoprotein receptor; Chinese Journal of Chemistry; 24(8): 1058-1061; (2006).
Maierhofer et al., "Probing multivalent carbohydrate-lectin interactions by an enzyme-linked lectin assay employing covalently immobilized carbohydrates" Bioorganic & Medicinal Chemistry; 15: 7661-7676; (2007).
Karskela et al.; "Synthesis and Cellular Uptake of Fluorescently Labeled Multivalent Hyaluronan Disaccharide Conjugates of Oligonucleotide Phosphorothioates"; Bioconjugate Chem.; 19(12): 2549-2558 (2008).
Khorev et al.; "Trivalent, Gal/GalNAc-containing ligands designed for the asialoglycoprotein receptor" Bioorganic & Medicinal Chemistry; 16: 5216-5231; (2008).
Akinc et al.; "Targeted Delivery of RNAi Therapeutics with Endogenous and Exogenous Ligan-Based Mechanisms"; Molecular Therapy 18(7): 1357-1364; (2010).
Jayaprakash et al.; "Non-nucloside Building Blocks for Copper-Assisted and Copper-Free Click Chemistry for the Efficient Synthesis of RNA Conjugates" Organic Letters; 12(23); 5410-5413; (2010).
Akinc et al.; "Targeted Delivery of RNAi Therapeutics with Endogenous and Exogenous Ligand-Based Mechanisms"; Molecular Therapy 18(7): 1357-1364; (2010).
Andre et al.; "Determination of modulation of ligand properties of synthetic complex-type biantennary N-glycans by introduction of bisecting GlcNAc in silico, in vitro and in vivo"; Eur. J. Biochem.; 271:118-134; (2004).
Katajisto et al.; "Solid-Phase Synthesis of Multiantennary Oligonucleotide Glycoconjugates Utilizing On-Support Oximation"; J. Org. Chem. 2004, 69, 7609-7615.
Kato et al., "N-acetylgalactosamine incorporation into a peptide containing consecutive threonine residues by UDP-N-acetyl-D-galactosaminide:polypeptide N-acetylgalactosaminyltransferases" Glycobiology: 11: 821-829; (2001).
Manoharan et al., "Introduction of a Lipophilic Tbioether Tether in the Minor Groove of Nucleic Acids for Antisense Applications" Bioorg. Med. Chem. Lett.; 3(12): 2765-2770; (1993).

\* cited by examiner

TARGETING LIGANDS FOR THERAPEUTIC COMPOUNDS

CROSS REFERENCE TO RELATED APPLICATIONS

This application is a continuation of U.S. patent application Ser. No. 16/363,108, filed Mar. 25, 2019, which is a continuation of U.S. patent application Ser. No. 15/542,423, filed Mar. 7, 2017, which claims priority to U.S. Provisional Patent Application Ser. No. 62/304,652, filed on Mar. 7, 2016, and U.S. Provisional Patent Application Ser. No. 62/370,754, filed on Aug. 4, 2016, and U.S. Provisional Patent Application Ser. No. 62/426,916, filed on Nov. 28, 2016, the contents of each of which are incorporated herein by reference in their entirety.

BACKGROUND

Many compounds need to be delivered to a specific location (for example, to desired cell(s)) to have a therapeutic effect or to be useful for diagnostic purposes. This is frequently the case when attempting to deliver a therapeutic compound in vivo. Further, being able to efficiently deliver a compound to a specific location can limit or potentially eliminate unintended consequences (such as off-target effects) that may be caused by administration of the compound. One method to facilitate delivery of a compound, such as a therapeutic compound, to a desired location in vivo, is by linking or attaching the compound to a targeting ligand.

One class of therapeutic compounds that can be targeted using targeting ligands are oligomeric compounds. Oligomeric compounds that include nucleotide sequences at least partially complementary to a target nucleic acid have been shown to alter the function and activity of the target both in vitro and in vivo. When delivered to a cell containing a target nucleic acid (such as mRNA), oligomeric compounds have been shown to modulate the expression of the target resulting in altered transcription or translation of the target nucleic acid. In certain instances, the oligomeric compound can reduce the expression of the gene by inhibiting the nucleic acid target and/or triggering the degradation of the target nucleic acid.

If the target nucleic acid is mRNA, one mechanism by which an expression-inhibiting oligomeric compound can modulate the expression of the mRNA target is through RNA interference. RNA interference is a biological process by which RNA or RNA-like molecules (such as chemically modified RNA molecules) are able to silence gene expression through degradation. The process of post-transcriptional gene silencing is thought to be an evolutionarily-conserved cellular defense mechanism used to prevent the expression of foreign genes.

Synthetic RNA and RNA-like molecules have been shown to elicit RNA interference in vivo. For example, Elbashir et al. (*Nature* 2000, 411, 494-98) describes RNAi induced by introduction of duplexes of synthetic 21-nucleotide RNA molecules in cultured mammalian cells. The types of synthetic RNA or RNA-like molecules that can trigger the RNAi response mechanism may be comprised of modified nucleotides and/or one or more non-phosphodiester linkages.

Additionally, single-stranded RNA and RNA-like molecules, which can also include modified nucleotides and have one or more non-phosphodiester linkages, can also alter the expression of a target nucleic acid, such as a target mRNA.

SUMMARY

Disclosed herein are targeting ligands that can enhance the delivery of therapeutic compounds to a specific target site, e.g., a specific organ or tissue, within a subject such as a human patient or animal. In some embodiments, the targeting ligands described herein can enhance the targeted delivery of expression-inhibiting oligomeric compounds. In some embodiments, the targeting ligands can enhance the delivery of expression-inhibiting oligomeric compounds to the liver.

The targeting ligands disclosed herein include or consist of one or more targeting moieties, one or more tethers, one or more branch point groups, and one or more linkers.

Disclosed herein are targeting ligands that include, consist of, or consist essentially of the general structure of Formula A of FIG. 20, wherein n is an integer from 1 to 4 (e.g., 1, 2, 3 or 4).

In some embodiments, the targeting ligands disclosed herein include, consist of, or consist essentially of the structure of Formula B:

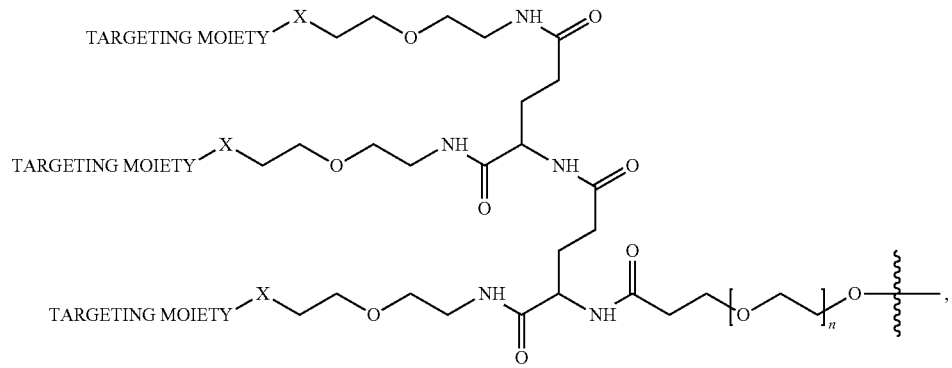

wherein n is an integer from 1 to 20 (e.g., 1, 2, 3, 4, 5, 6, 7, 8, 9, 10, 11, 12, 13, 14, 15, 16, 17, 18, 19, or 20); X is O, S, or NH; and Targeting Moiety is selected from the group consisting of: N-acetyl-galactosamine, galactose, galactosamine, N-formyl-galactosamine, N-propionyl-galactosamine, N-n-butanoylgalactosamine, and N-iso-butanoyl-galactosamine.

In some embodiments, the targeting ligands disclosed herein include, consist of, or consist essentially of, the following structure:

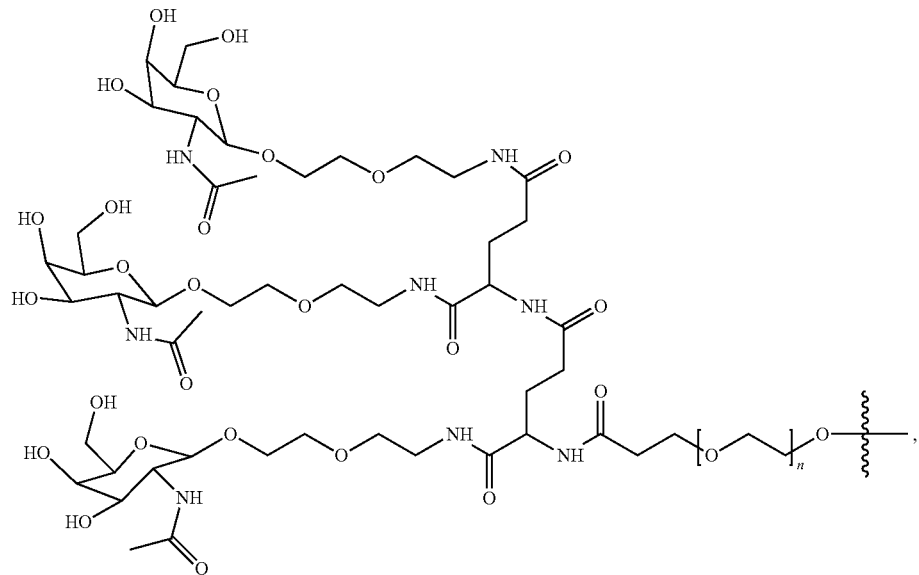

wherein n is an integer from 1 to 20 (Structure 1).

In some embodiments, the targeting ligands disclosed include, consist of, or consist essentially of, the structure selected from:

(Structure 101)

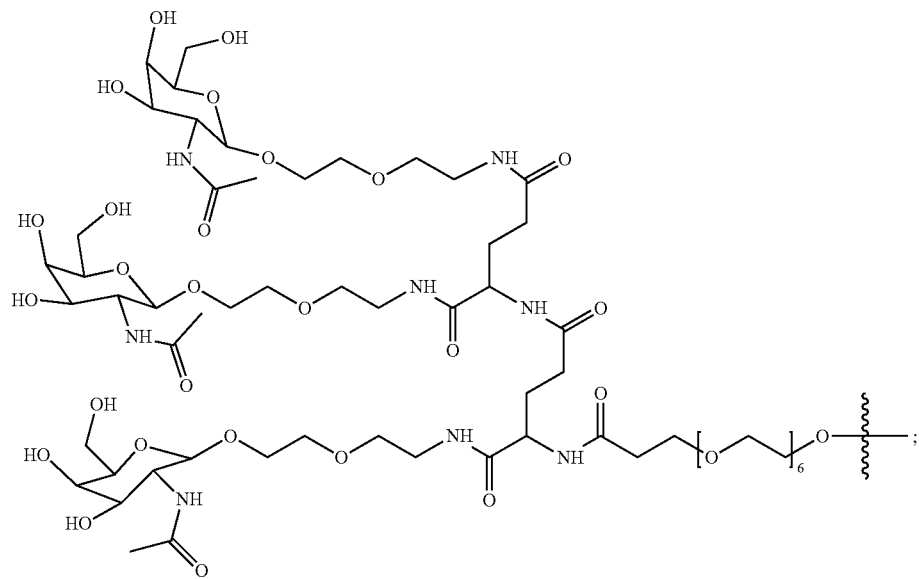

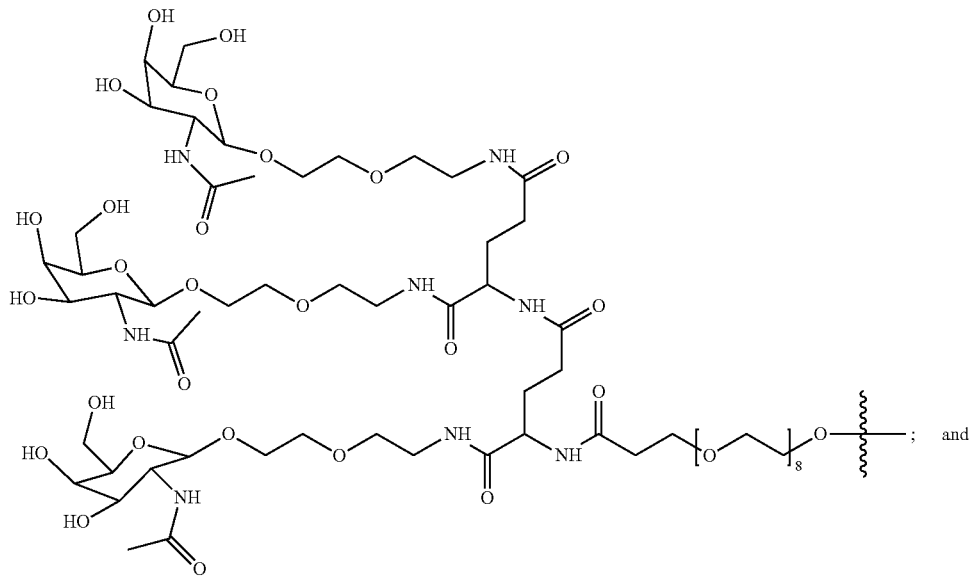

(Structure 102)

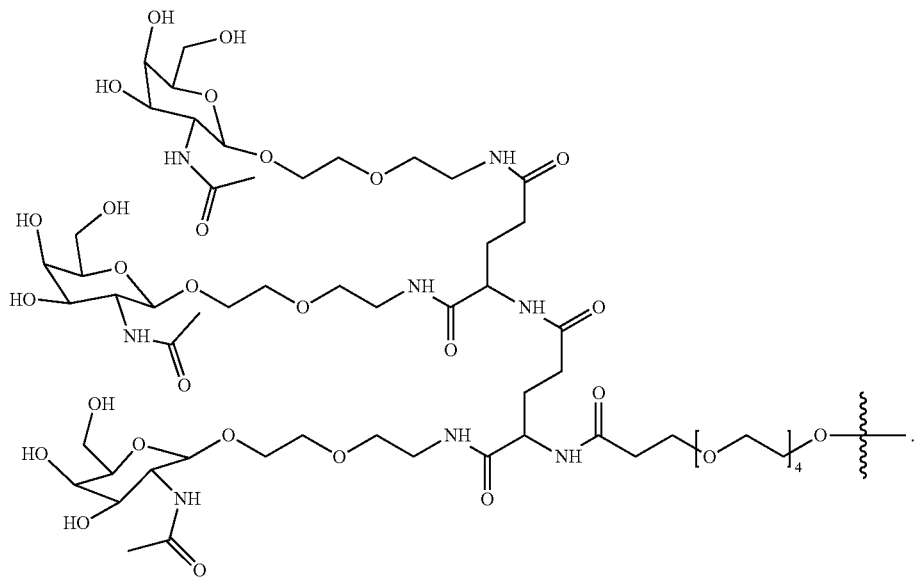

(Structure 103)

The targeting ligands disclosed herein include one or more targeting moieties. In some embodiments, the targeting ligands disclosed herein include N-acetyl-galactosamine as the targeting moiety.

The targeting ligands disclosed herein can be linked, directly or indirectly, to a compound, such as a therapeutic compound, e.g., an expression-inhibiting oligomeric compound, for example, to the 3' or 5' terminal end of the expression-inhibiting oligomeric compound. In some embodiments, the expression-inhibiting oligomeric compound includes one or more modified nucleotides. In some embodiments, the expression-inhibiting oligomeric compound is an RNAi agent, such as a double-stranded RNAi agent. In some embodiments, the targeting ligands disclosed herein are linked to the 5' terminal end of the sense strand of a double-stranded RNAi agent. In some embodiments, the targeting ligands disclosed herein are linked to the RNAi agent via a phosphate, phosphorothioate, or phosphonate group at the 5' terminal end of the sense strand of a double-stranded RNAi agent.

Disclosed herein are compositions including a targeting ligand and an expression-inhibiting oligomeric compound. Disclosed herein are compositions including a targeting ligand and an RNAi agent.

In some embodiments, the compositions disclosed herein including a targeting ligand and an RNAi agent have the structure represented by:

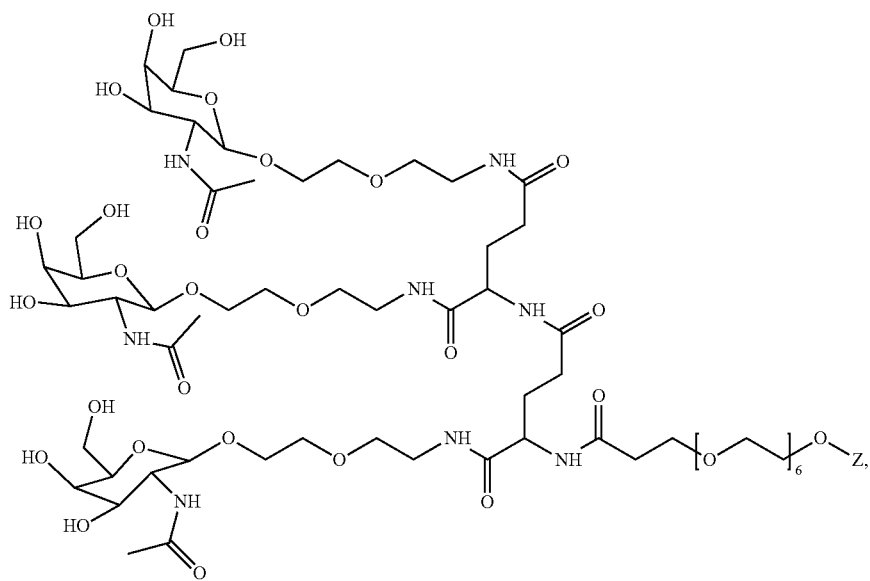
wherein Z includes or consists of an expression-inhibiting oligomeric compound (Structure 101a);
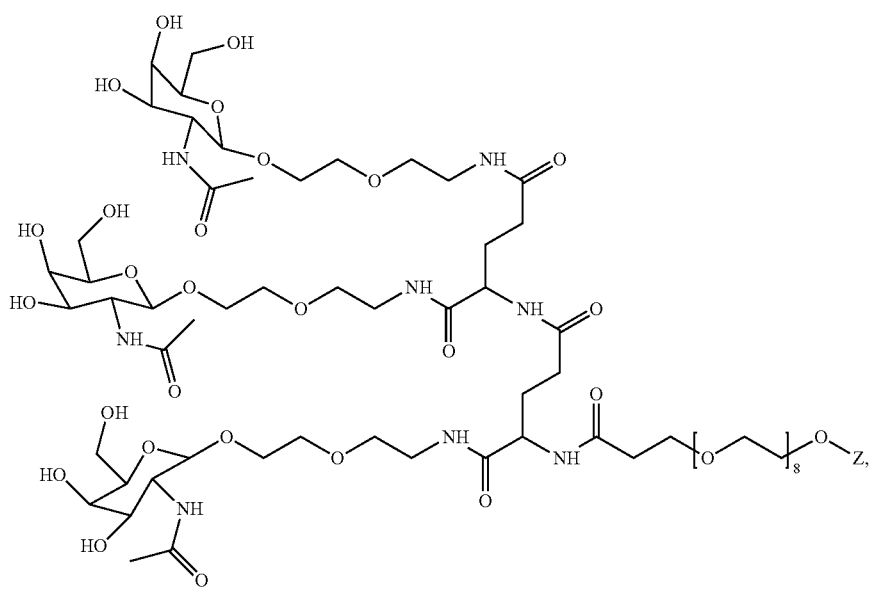
wherein Z includes or consists of an expression-inhibiting oligomeric compound (Structure 102a); and

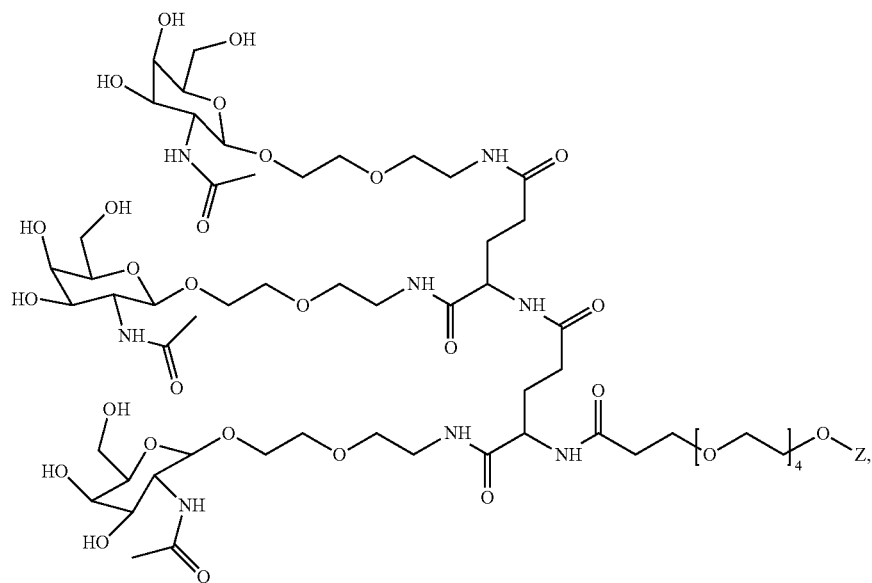
wherein Z includes or consists of an expression-inhibiting oligomeric compound (Structure 103a).
Disclosed herein are phosphoramidite compounds including targeting ligands.
In some embodiments, the phosphoramidite compounds including targeting ligands disclosed herein have the structure represented by:
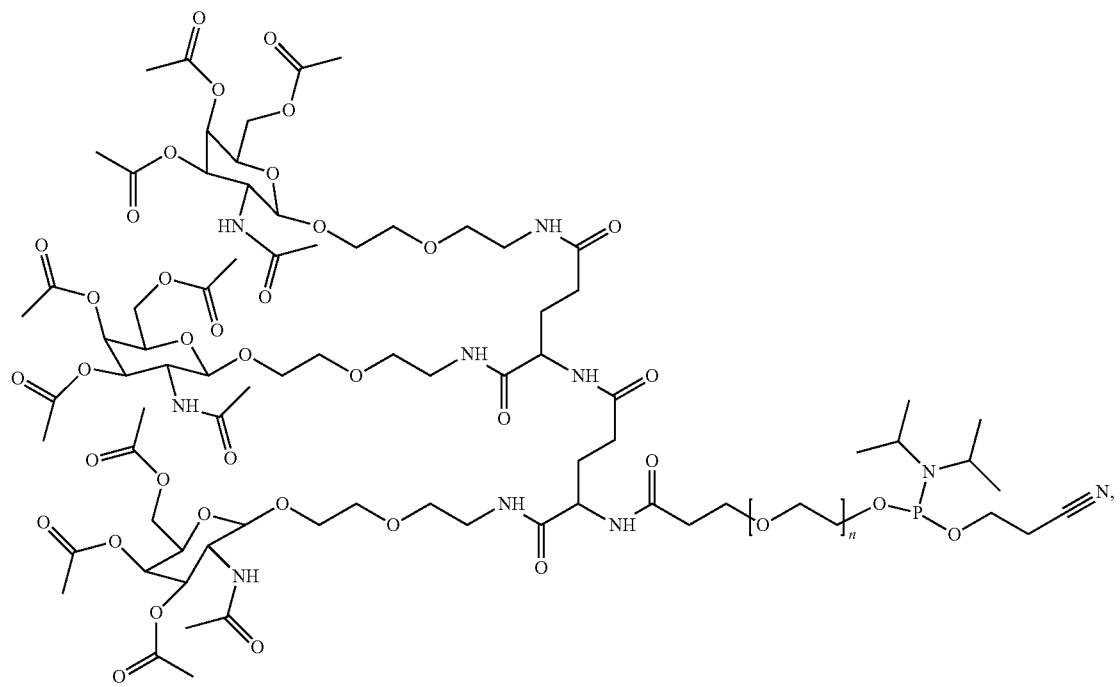
wherein n is an integer from 1 to 20 (e.g., 1, 2, 3, 4, 5, 6, 7, 8, 9, 10, 11, 12, 13, 14, 15, 16, 17, 18, 19, or 20) (Structure 1d);

(Structure 101d)

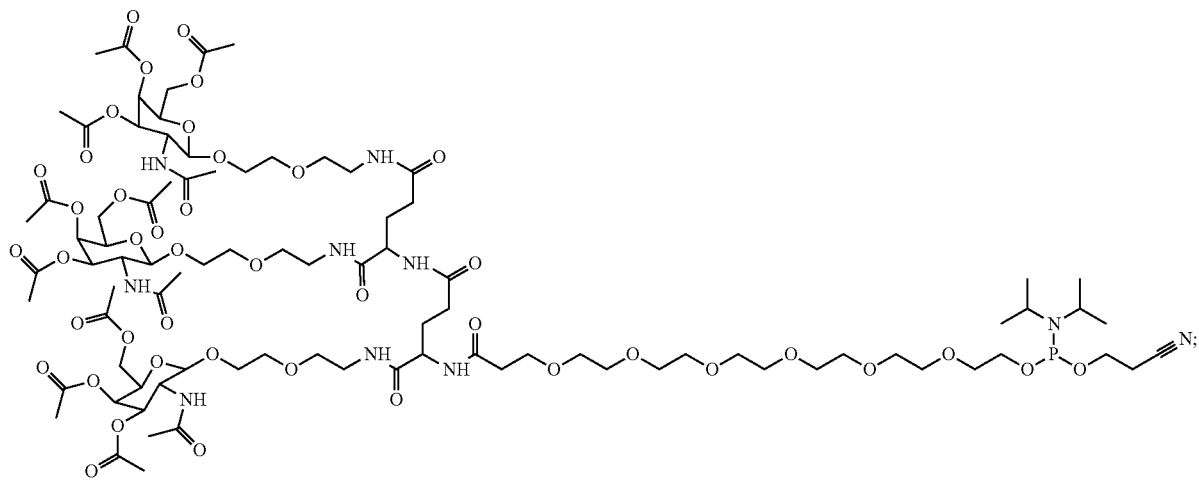

(Structure 102d)

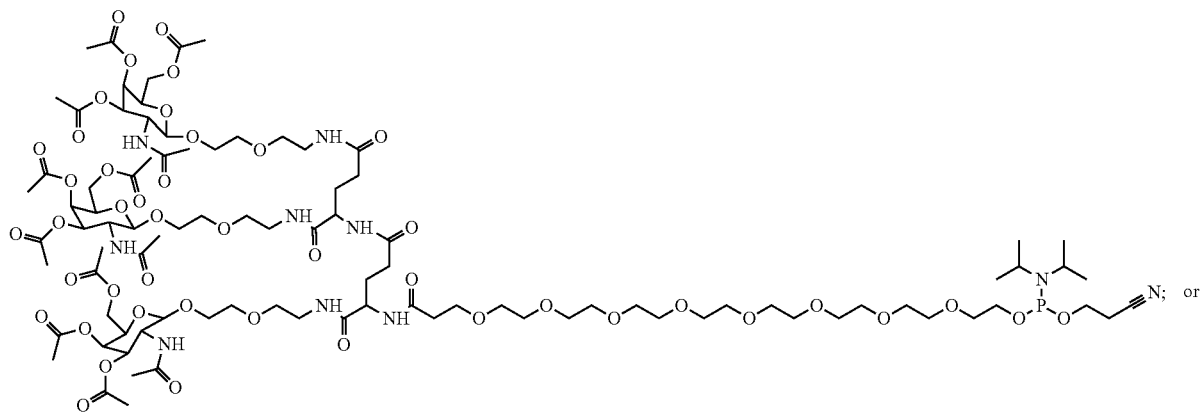

(Structure 103d)

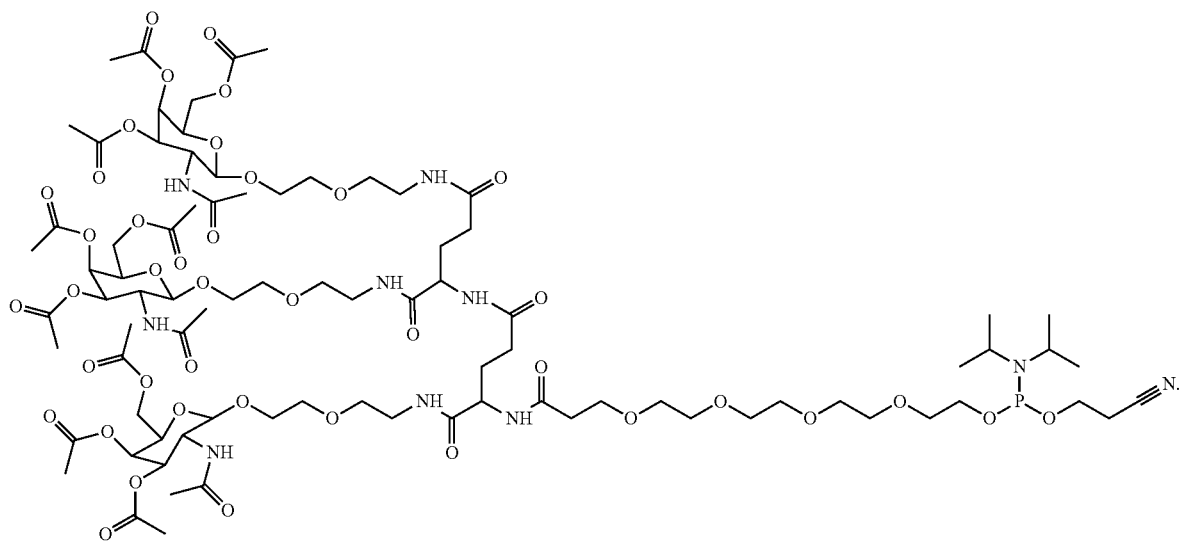

Also disclosed are pharmaceutical compositions that include the targeting ligands disclosed herein.

Disclosed are methods of treating a disease or disorder that would benefit from administration of a therapeutic oligomeric compound, the method including administering to a subject a therapeutic oligomeric compound linked to a targeting ligand disclosed herein.

Disclosed herein are methods of inhibiting expression of a target nucleic acid in a subject, the method including administering a therapeutic amount of an expression-inhibiting oligomeric compound linked to the targeting ligands disclosed herein.

Disclosed herein are methods of delivering an expression-inhibiting oligomeric compound to the liver in vivo, comprising administering an expression-inhibiting oligomeric compound linked to a targeting ligand disclosed herein to a subject.

As used herein, the term "linked" when referring to the connection between two molecules means that two molecules are joined by a covalent bond or that two molecules are associated via noncovalent bonds (e.g., hydrogen bonds or ionic bonds). In some examples, where the term "linked" refers to the association between two molecules via noncovalent bonds, the association between the two different molecules has a $K_D$ of less than $1\times10^{-4}$ M (e.g., less than $1\times10^{-5}$ M, less than $1\times10^{-6}$ M, or less than $1\times10^{-7}$ M) in physiologically acceptable buffer (e.g., phosphate buffered saline).

As used herein, the term "directly linked" refers to a first compound or group being linked to a second compound or group without any intervening atoms or groups of atoms. As used herein, the term "indirectly linked" refers to a first compound being linked to a second compound or group through an intermediary group, compound, or molecule, such as, for example, a linking group. Unless otherwise stated, the term "linked" as used herein includes both "directly linked" and "indirectly linked" as those terms are defined herein.

As used herein, an "oligomeric compound" is a nucleotide sequence containing about 10-50 nucleotides or nucleotide base pairs. In some embodiments, an oligomeric compound has a nucleobase sequence that is at least partially complementary to a coding sequence in an expressed target nucleic acid or target gene within a cell. In some embodiments, the oligomeric compounds, upon delivery to a cell expressing a gene, are able to inhibit the expression of the underlying gene, and are referred to herein as "expression-inhibiting oligomeric compounds." The gene expression can be inhibited in vitro or in vivo. "Oligomeric compounds" include, but are not limited to: oligonucleotides, single-stranded oligonucleotides, single-stranded antisense oligonucleotides, short interfering RNAs (siRNAs), double-strand RNAs (dsRNA), micro RNAs (miRNAs), short hairpin RNAs (shRNA), ribozymes, interfering RNA molecules, and dicer substrates.

As used herein, the term "oligonucleotide" means a polymer of linked nucleosides each of which can be independently modified or unmodified.

As used herein, the term "single-stranded oligonucleotide" means a single-stranded oligomeric compound having a sequence at least partially complementary to a target mRNA, that is capable of hybridizing to a target mRNA through hydrogen bonding under mammalian physiological conditions (or comparable conditions in vitro). In some embodiments, a single-stranded oligonucleotide is a single stranded antisense oligonucleotide.

As used herein, an "RNAi agent" means an agent that contains an RNA or RNA-like (e.g., chemically modified RNA) oligonucleotide molecule that is capable of degrading or inhibiting translation of messenger RNA (mRNA) transcripts of a target mRNA in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action. RNAi agents include, but are not limited to: single-stranded oligonucleotides, single-stranded antisense oligonucleotides, short interfering RNAs (siRNAs), double-strand RNAs (dsRNA), micro RNAs (miRNAs), short hairpin RNAs (shRNA), and dicer substrates. The RNAi agents described herein are comprised of an oligonucleotide having a strand that is at least partially complementary to the mRNA being targeted. In some embodiments, the RNAi agents described herein are double-stranded, and are comprised of an antisense strand and a sense strand that is at least partially complementary to the antisense strand. RNAi agents may be comprised of modified nucleotides and/or one or more non-phosphodiester linkages. In some embodiments, the RNAi agents described herein are single-stranded.

As used herein, the terms "silence," "reduce," "inhibit," "down-regulate," or "knockdown" when referring to expression of a given gene, mean that the expression of the gene, as measured by the level of RNA transcribed from the gene or the level of polypeptide, protein or protein subunit translated from the mRNA in a cell, group of cells, tissue, organ, or subject in which the gene is transcribed, is reduced when the cell, group of cells, tissue, organ, or subject is treated with oligomeric compounds linked to the targeting ligands described herein as compared to a second cell, group of cells, tissue, organ, or subject that has not or have not been so treated.

As used herein, the term "sequence" or "nucleotide sequence" mean a succession or order of nucleobases or nucleotides, described with a succession of letters using the standard nucleotide nomenclature.

As used herein, and unless otherwise indicated, the term "complementary," when used to describe a first nucleotide sequence (e.g., RNAi agent sense strand or targeted mRNA) in relation to a second nucleotide sequence (e.g., single-stranded antisense oligonucleotide or a double-stranded RNAi agent antisense strand), means the ability of an oligonucleotide or polynucleotide including the first nucleotide sequence to hybridize (form base pair hydrogen bonds under mammalian physiological conditions (or comparable conditions in vitro)) and form a duplex or double helical structure under certain conditions with an oligonucleotide or polynucleotide including the second nucleotide sequence. Complementary sequences include Watson-Crick base pairs or non-Watson-Crick base pairs and include natural or modified nucleotides or nucleotide mimics, at least to the extent that the above requirements with respect to the ability to hybridize are fulfilled.

As used herein, "perfectly complementary" or "fully complementary" means that all (100%) of the bases in a contiguous sequence of a first polynucleotide will hybridize with the same number of bases in a contiguous sequence of a second polynucleotide. The contiguous sequence may comprise all or a part of a first or second nucleotide sequence.

As used herein, "partially complementary" means that in a hybridized pair of nucleobase sequences, at least 70%, but not all, of the bases in a contiguous sequence of a first polynucleotide will hybridize with the same number of bases in a contiguous sequence of a second polynucleotide.

As used herein, "substantially complementary" means that in a hybridized pair of nucleobase sequences, at least 85%, but not all, of the bases in a contiguous sequence of a first polynucleotide will hybridize with the same number of bases in a contiguous sequence of a second polynucleotide. The terms "complementary," "fully complementary," and "substantially complementary" herein may be used with respect to the base matching between the sense strand and the antisense strand of a double-stranded RNAi agent, between the antisense strand of a double-stranded RNAi agent and a sequence of a target mRNA, or between a single-stranded antisense oligonucleotide and a sequence of a target mRNA.

As used herein, the terms "treat," "treatment," and the like, mean the methods or steps taken to provide relief from or alleviation of the number, severity, and/or frequency of one or more symptoms of a disease in a subject.

As used herein, the phrase "introducing into a cell," when referring to an oligomeric compound, means functionally delivering the oligomeric compound into a cell. The phrase "functional delivery," means that delivering the oligomeric compound to the cell in a manner that enables the oligomeric compound to have the expected biological activity, e.g., sequence-specific inhibition of gene expression.

Unless stated otherwise, use of the symbol ⟋ as used herein means that any group or groups may be linked thereto that is in accordance with the scope of the inventions described herein.

As used herein, the term "isomers" refers to compounds that have identical molecular formulae, but that differ in the nature or the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images are termed "enantiomers," or sometimes optical isomers. A carbon atom bonded to four non-identical substituents is termed a "chiral center."

As used herein, unless specifically identified in a structure as having a particular conformation, for each structure in which asymmetric centers are present and thus give rise to enantiomers, diastereomers, or other stereoisomeric configurations, each structure disclosed herein is intended to represent all such possible isomers, including their optically pure and racemic forms. For example, the structures disclosed herein are intended to cover mixtures of diastereomers as well as single stereoisomers.

The term "substituted," as used herein, means that any one or more hydrogens on the designated atom, usually a carbon, oxygen, or nitrogen atom, is replaced with any group as defined herein, provided that the designated atom's normal valency is not exceeded, and that the substitution results in a stable compound. Non-limiting examples of substituents include C1-C6 alkyl, C2-C6 alkenyl, C2-C6 alkynyl, cyano, hydroxyl, oxo, carboxyl, cycloalkyl, cycloalkenyl, heterocyclyl, heteroaryl, aryl, keto, alkoxycarbonyl, aryloxycarbonyl, heteroaryloxycarbonyl, or halo (e.g., F, Cl, Br, I). When a substituent is keto or oxo (i.e., =O), then two (2) hydrogens on the atom are replaced. Ring double bonds, as used herein, are double bonds that are formed between two adjacent ring atoms (e.g., C=C, C=N, N=N, etc.).

Some compounds of the present disclosure can exist in a tautomeric form that is also intended to be encompassed within the scope of the present disclosure. "Tautomers" are compounds whose structures differ markedly in the arrangement of atoms, but which exist in easy and rapid equilibrium. It is to be understood that compounds of the present disclosure may be depicted as different tautomers. It should also be understood that when compounds have tautomeric forms, all tautomeric forms are intended to be within the scope of the disclosure, and the naming of the compounds does not exclude any tautomeric form.

The compounds and pharmaceutically acceptable salts of the present disclosure can exist in one or more tautomeric forms, including ketone-enol, amide-nitrile, lactam-lactim, amide-imidic acid tautomerism in heterocyclic rings (e.g., in the nucleobases guanine, thymine, and cytosine), amine-enamine and enamine-enamine and geometric isomers and mixtures thereof. Ring-chain tautomerism, exhibited by glucose and other sugars, arises as a result of the aldehyde group (—CHO) in a sugar chain molecule reacting with one of the hydroxy groups (—OH) in the same molecule to give it a cyclic (ring-shaped) form. All such tautomeric forms are included within the scope of the present disclosure. Tautomers exist as mixtures of a tautomeric set in solution. In solid form, usually one tautomer predominates. Even though one tautomer may be described, the present disclosure includes all tautomers of the compounds disclosed herein. The concept of tautomers that are interconvertible by tautomerizations is called tautomerism. In tautomerism, a simultaneous shift of electrons and a hydrogen atom occurs.

Tautomerizations are catalyzed by: Base: 1. deprotonation; 2. formation of a delocalized anion (e.g. an enolate); 3. protonation at a different position of the anion; Acid: 1. protonation; 2. formation of a delocalized cation; 3. deprotonation at a different position adjacent to the cation.

As used herein, the term "alkyl" refers to a saturated aliphatic hydrocarbon group, straight chain or branched, having from 1 to 10 carbon atoms unless otherwise specified. For example, "C1-C6 alkyl" includes alkyl groups having 1, 2, 3, 4, 5, or 6 carbons in a linear or branched arrangement. As used herein, the term "aminoalkyl" refers to an alkyl group as defined above, substituted at any position with one or more amino groups as permitted by normal valency. The amino groups may be unsubstituted, monosubstituted, or di-substituted.

As used herein, the term "cycloalkyl" means a saturated or unsaturated nonaromatic hydrocarbon ring group having from 3 to 14 carbon atoms, unless otherwise specified. Examples of cycloalkyl groups include, but are not limited to, cyclopropyl, methyl-cyclopropyl, 2,2-dimethyl-cyclobutyl, 2-ethyl-cyclopentyl, cyclohexyl, etc. Cycloalkyls may include multiple spiro- or fused rings. Cycloalkyl groups are optionally mono-, di-, tri-, tetra-, or penta-substituted on any position as permitted by normal valency.

As used herein, the term "alkenyl" refers to a non-aromatic hydrocarbon radical, straight or branched, containing at least one carbon-carbon double bond, and having from 2 to 10 carbon atoms unless otherwise specified. Up to five carbon-carbon double bonds may be present in such groups. For example, "C2-C6" alkenyl is defined as an alkenyl radical having from 2 to 6 carbon atoms. Examples of alkenyl groups include, but are not limited to, ethenyl, propenyl, butenyl, and cyclohexenyl. The straight, branched, or cyclic portion of the alkenyl group may contain double bonds and is optionally mono-, di-, tri-, tetra-, or penta-substituted on any position as permitted by normal valency. The term "cycloalkenyl" means a monocyclic hydrocarbon group having the specified number of carbon atoms and at least one carbon-carbon double bond.

As used herein, the term "alkynyl" refers to a hydrocarbon radical, straight or branched, containing from 2 to 10 carbon atoms, unless otherwise specified, and containing at least one carbon-carbon triple bond. Up to 5 carbon-carbon triple bonds may be present. Thus, "C2-C6 alkynyl" means an alkynyl radical having from 2 to 6 carbon atoms. Examples of alkynyl groups include, but are not limited to, ethynyl, 2-propynyl, and 2-butynyl. The straight or branched portion of the alkynyl group may contain triple bonds as permitted by normal valency, and may be optionally mono-, di-, tri-, tetra-, or penta-substituted on any position as permitted by normal valency.

As used herein, "alkoxyl" or "alkoxy" refers to an alkyl group as defined above with the indicated number of carbon atoms attached through an oxygen bridge. $C_{1-6}$alkoxy, is intended to include $C_1$, $C_2$, $C_3$, $C_4$, $C_5$, and $C_6$ alkoxy groups. $C_{1-8}$ alkoxy, is intended to include $C_1$, $C_2$, $C_3$, $C_4$, $C_5$, $C_6$, $C_7$, and $C_8$ alkoxy groups. Examples of alkoxy include, but are not limited to, methoxy, ethoxy, n-propoxy, i-propoxy, n-butoxy, s-butoxy, t-butoxy, n-pentoxy, s-pentoxy, n-heptoxy, and n-octoxy.

As used herein, "keto" refers to any alkyl, alkenyl, alkynyl, cycloalkyl, cycloalkenyl, heterocyclyl, heteroaryl, or aryl group as defined herein attached through a carbonyl bridge. Examples of keto groups include, but are not limited to, alkanoyl (e.g., acetyl, propionyl, butanoyl, pentanoyl, hexanoyl), alkenoyl (e.g., acryloyl) alkynoyl (e.g., ethynoyl, propynoyl, butynoyl, pentynoyl, hexynoyl), aryloyl (e.g., benzoyl), heteroaryloyl (e.g., pyrroloyl, imidazoloyl, quinolinoyl, pyridinoyl).

As used herein, "alkoxycarbonyl" refers to any alkoxy group as defined above attached through a carbonyl bridge (i.e., —C(O)O-alkyl). Examples of alkoxycarbonyl groups include, but are not limited to, methoxycarbonyl, ethoxycarbonyl, iso-propoxycarbonyl, n-propoxycarbonyl, t-butoxycarbonyl, benzyloxycarbonyl or n-pentoxycarbonyl.

As used herein, "aryloxycarbonyl" refers to any aryl group as defined herein attached through an oxycarbonyl bridge (i.e., —C(O)O-aryl). Examples of aryloxycarbonyl groups include, but are not limited to, phenoxycarbonyl and naphthyloxycarbonyl.

As used herein, "heteroaryloxycarbonyl" refers to any heteroaryl group as defined herein attached through an oxycarbonyl bridge (i.e., —C(O)O-heteroaryl). Examples of heteroaryloxycarbonyl groups include, but are not limited to, 2-pyridyloxycarbonyl, 2-oxazolyloxycarbonyl, 4-thiazolyloxycarbonyl, or pyrimidinyloxycarbonyl.

As used herein, "aryl" or "aromatic" means any stable monocyclic or polycyclic carbon ring of up to 7 atoms in each ring, wherein at least one ring is aromatic. Examples of aryl groups include, but are not limited to, phenyl, naphthyl, anthracenyl, tetrahydronaphthyl, indanyl, and biphenyl. In cases where the aryl substituent is bicyclic and one ring is non-aromatic, it is understood that attachment is via the aromatic ring. Aryl groups are optionally mono-, di-, tri-, tetra-, or penta-substituted on any position as permitted by normal valency.

As used herein, the term "heteroaryl" represents a stable monocyclic or polycyclic ring of up to 7 atoms in each ring, wherein at least one ring is aromatic and contains from 1 to 4 heteroatoms selected from the group consisting of O, N and S. Examples of heteroaryl groups include, but are not limited to, acridinyl, carbazolyl, cinnolinyl, quinoxalinyl, pyrrazolyl, indolyl, benzotriazolyl, furanyl, thienyl, benzothienyl, benzofuranyl, benzimidazolonyl, benzoxazolonyl, quinolinyl, isoquinolinyl, dihydroisoindolonyl, imidazopyridinyl, isoindolonyl, indazolyl, oxazolyl, oxadiazolyl, isoxazolyl, indolyl, pyrazinyl, pyridazinyl, pyridinyl, pyrimidinyl, pyrrolyl, tetrahydroquinoline. "Heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring. Heteroaryl groups are optionally mono-, di-, tri-, tetra-, or penta-substituted on any position as permitted by normal valency.

As used herein, the term "heterocycle," "heterocyclic," or "heterocyclyl" means a 3- to 14-membered aromatic or nonaromatic heterocycle containing from 1 to 4 heteroatoms selected from the group consisting of O, N and S, including polycyclic groups. As used herein, the term "heterocyclic" is also considered to be synonymous with the terms "heterocycle" and "heterocyclyl" and is understood as also having the same definitions set forth herein. "Heterocyclyl" includes the above mentioned heteroaryls, as well as dihydro and tetrahydro analogs thereof. Examples of heterocyclyl groups include, but are not limited to, azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxooxazolidinyl, oxazolyl, oxazoline, oxopiperazinyl, oxopyrrolidinyl, oxomorpholinyl, isoxazoline, oxetanyl, pyranyl, pyrazinyl, pyrazolyl, pyridazinyl, pyridopyridinyl, pyridazinyl, pyridyl, pyridinonyl, pyrimidyl, pyrimidinonyl, pyrrolyl, quinazolinyl, quinolyl, quinoxalinyl, tetrahydropyranyl, tetrahydrofuranyl, tetrahydrothiopyranyl, tetrahydroisoquinolinyl, tetrazolyl, tetrazolopyridyl, thiadiazolyl, thiazolyl, thienyl, triazolyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dioxidothiomorpholinyl, methylenedioxybenzoyl, tetrahydrofuranyl, and tetrahydrothienyl, and N-oxides thereof. Attachment of a heterocyclyl substituent can occur via a carbon atom or via a heteroatom. Heterocyclyl groups are optionally mono-, di-, tri-, tetra-, or penta-substituted on any position as permitted by normal valency.

The person of ordinary skill in the art would readily understand and appreciate that the compounds and compositions disclosed herein may have certain atoms (e.g., N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the pH of the environment, as would be readily understood by the person of ordinary skill in the art.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

Unless otherwise defined, all technical and scientific terms used herein have the same meaning as commonly understood by one of ordinary skill in the art to which this FIG. 20 is a formula (Formula A) that represents the general structure of targeting ligands disclosed herein.

DETAILED DESCRIPTION

Described herein are novel targeting ligands that are linked to compounds, such as therapeutic or diagnostic expression-inhibiting oligomeric compounds. In some embodiments, the compounds that are linked to the targeting ligands described herein include or consist of therapeutic compounds that are RNAi agents. The targeting ligands can be used to target therapeutic compounds to a desired location of a target nucleic acid or target gene. Also described herein are compositions including targeting ligands and therapeutic compounds, such as compositions including or consisting of targeting ligands and expression-inhibiting oligomeric compounds.

The new targeting ligands disclosed herein provide efficient targeting or bio-distribution, sufficient stability in vivo and in vitro, and are suitable for synthesis as phosphoramidites, which reduces the cost and burden of manufacture, and can increase efficacy over previously considered targeting ligands linked to an expression-inhibiting oligomeric compound, such as an RNAi agent.

Targeting Ligands

Targeting ligands are comprised of one or more targeting group(s) or targeting moiety(ies), which can serve to enhance the pharmacokinetic or bio-distribution properties of the compound to which they are linked, and improve cell- or tissue-specific distribution and cell-specific uptake of the conjugated composition. In general, a targeting ligand aids in directing the delivery of the therapeutic compound to which it is linked to the desired target site. In some instances, the targeting moiety may bind to a cell or cell receptor, and initiate endocytosis to facilitate entry of the therapeutic compound into the cell. Targeting moieties can include compounds with affinity to cell receptors or cell surface molecules or antibodies. A variety of targeting ligands that contain targeting moieties can be linked to therapeutic agents and other compounds to target the agents to cells and specific cellular receptors. Types of targeting moieties include carbohydrates, cholesterol and cholesteryl groups, and steroids. Targeting moieties that can bind to cell receptors include saccharides, such as galactose, galactose derivatives (such as N-acetyl-galactosamine), mannose, and mannose derivatives; other carbohydrates; glycans; haptens; vitamins; folate; biotin; aptamers; and peptides, such as RGD-containing peptides, insulin, EGF, and transferrin.

Targeting moieties that are known to bind to the asialoglycoprotein receptor (ASGPR) are particularly useful in directing the delivery of oligomeric compounds to the liver. Asialoglycoprotein receptors are abundantly expressed on liver cells, including hepatocytes. Cell receptor targeting moieties that target ASGPR include galactose and galactose derivatives. In particular, clusters of galactose derivatives, including clusters comprised of two, three, or four N-acetylgalactosamines (GalNAc or NAG), can facilitate uptake of certain compounds in liver cells. GalNAc clusters conjugated to oligomeric compounds serve to direct the composition to the liver, where the N-acetyl-galactosamine sugars are able to bind to the asialoglycoprotein receptors on the surface of the liver cell. The binding to an asialoglycoprotein receptor is believed to initiate receptor-mediated endocytosis, thereby facilitating entry of the compound into the interior of the cell.

The targeting ligands disclosed herein may include one, two, three, four, or more than four targeting moieties. In invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

some embodiments, the targeting ligands disclosed herein can include one, two, three, four, or more than four targeting moieties linked to a branch point group. In some embodiments, the targeting ligands disclosed herein can include one, two, three, four, or more than four targeting moieties linked to a branch point group wherein each targeting moiety is linked to the branch point group via a tether.

In some embodiments, the targeting ligands disclosed herein can include one, two, three, four, or more than four asialoglycoprotein receptor (ASGPR) targeting moieties linked to a branch point group. In some embodiments, the targeting ligands disclosed herein can include one, two, three, four, or more than four ASGPR targeting moieties linked to a branch point group wherein each ASGPR targeting moiety is linked to the branch point group via a tether.

Figure 20:
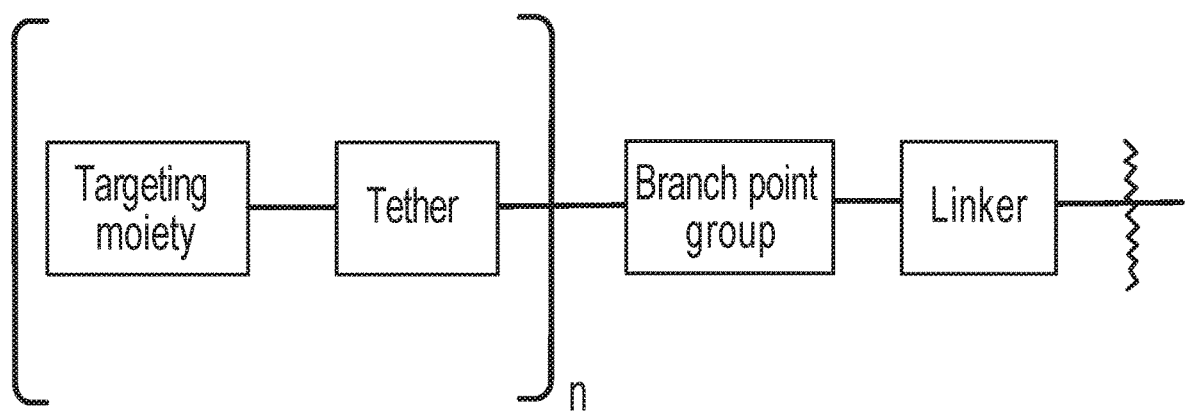

The targeting ligands described herein are represented by the following Formula A of FIG. 20, wherein n is an integer from 1 to 4 (e.g., 1, 2, 3 or 4) (Formula A). In some embodiments, n in Formula A is an integer from 1-3, 1-2, 2-4, 2-3, or 3-4.

The targeting ligands disclosed herein can be linked to therapeutic compounds, such as oligomeric compounds. In some embodiments, the targeting ligand is linked to the therapeutic compound via an additional linker and/or a cleavable moiety, which is then linked to the therapeutic compound. In some embodiments, targeting ligands are ligated to the therapeutic compound itself.

In some embodiments, the therapeutic compound is an expression-inhibiting oligomeric compound. In some embodiments, the expression-inhibiting oligomeric compound is an RNAi agent. In some embodiments, the expression-inhibiting oligomeric compound is a double-stranded RNAi agent.

In some embodiments, a targeting ligand is linked directly or indirectly to the 5' end of the sense strand of a double-stranded RNAi agent. In some embodiments, the targeting ligand is linked directly or indirectly to the 3' end of the sense strand of a double-stranded RNAi agent. In some embodiments, the targeting ligand is linked directly or indirectly to the 5' end or the 3' end of the antisense strand of a double-stranded RNAi agent. In some embodiments, the targeting ligand is linked directly or indirectly to the 5' end or the 3' end of a single-stranded RNAi agent.

In some embodiments, a targeting ligand is linked to a double-stranded RNAi agent via a phosphate, phosphonate, phosphorothioate, or other internucleoside linking group, at the 5' end of the terminal nucleoside of the sense strand of the double-stranded RNAi agent.

In some embodiments, a targeting ligand disclosed herein includes a cleavable moiety. In some embodiments, a cleavable moiety includes or consists of a phosphate or other internucleoside linking group that may be cleaved. In some embodiments, the targeting ligand is linked to a therapeutic compound via a cleavable moiety.

In some embodiments, a targeting ligand disclosed herein is linked to an additional group or groups that includes a cleavable moiety. In some embodiments, the targeting ligand is linked to a cleavable moiety, which is then linked to an expression-inhibiting oligomeric compound.

In some embodiments, the targeting ligand is a phosphoramidite compound (also referred to herein as a "phosphoramidite-containing compound"). A phosphoramidite compound including a targeting ligand described herein may be useful to readily attach the targeting ligand to the therapeutic compound or to other groups, using methods generally known in the art for phosphoramidite synthesis. In some embodiments, the phosphoramidite compound including the targeting ligand is linked to an expression-inhibiting oligomeric compound using methods generally known in the art. In some embodiments, the targeting ligand-containing phosphoramidite is linked to the 5' end of the sense strand of a double-stranded RNAi agent.

In some embodiments, an expression-inhibiting oligomeric compound linked to a targeting ligand includes a single-stranded oligonucleotide. In some embodiments, the single-stranded oligonucleotide is a single-stranded antisense oligonucleotide. In some embodiments, the targeting ligand is linked directly to a single-stranded antisense oligonucleotide. In some embodiments, additional groups are inserted between a targeting ligand and a single-stranded oligonucleotide.

In some embodiments, the targeting ligand linked to an RNAi agent includes one or more N-acetyl-galactosamine sugars as a targeting moiety or targeting moieties.

In some embodiments, the targeting ligand linked to an expression-inhibiting oligomeric compound includes a tether that includes polyethylene glycol (PEG). In some embodiments, a tether consists of PEG. In some embodiments a tether includes a PEG having 1 to 10 ethylene glycol units. In some embodiments a tether includes a PEG having 1, 2, 3, 4, 5, 6, 7, 8, 9, or 10 ethylene glycol units.

In some embodiments, the targeting ligand linked to the RNAi agent comprises polyethylene glycol (PEG) as the linker. In some embodiments, the linker comprises PEG. In some embodiments, the linker consists of PEG. In some embodiments a linker comprises a PEG having 1 to 20 ethylene glycol units. In some embodiments a tether comprises a PEG having 1, 2, 3, 4, 5, 6, 7, 8, 9, 10, 11, 12, 13, 14, 15, 16, 17, 18, 19, or 20 ethylene glycol units.

In some embodiments, an expression-inhibiting oligomeric compound linked to any of the targeting ligands disclosed herein includes an RNAi agent. In some embodiments, a targeting ligand disclosed herein is linked, either directly or indirectly, to an RNAi agent.

In some embodiments, a targeting ligand disclosed herein is linked directly to an RNAi agent. In some embodiments, a targeting ligand disclosed herein is linked indirectly to an RNAi agent, as additional group(s) are inserted between the RNAi agent and the linker of the targeting ligand. In some embodiments, a second linker is included between the linker and the therapeutic compound.

Targeting Ligand Structures, And Phosphoramidite Compounds Including Targeting Ligands.

The targeting ligands disclosed herein may be comprised of one or more targeting moieties, tethers, branch point groups, and linkers. The targeting ligands disclosed herein may contain one, two, three, four, or more than four targeting moieties.

In some embodiments, the targeting ligands disclosed herein are synthesized to be in the form of a phosphoramidite compound. Phosphoramidites are widely used in the chemical synthesis of RNA and DNA. In some embodiments, the phosphoramidite-containing targeting ligands disclosed herein are added to the 5' end of the sense strand of a double-stranded RNAi agent. It can be especially advantageous to prepare the targeting ligand as a phosphoramidite when the targeting ligand is to be linked to the 5' terminal end of an expression-inhibiting oligomeric compound. Not wishing to be bound by theory, it is understood that preparing the targeting ligand as a phosphoramidite when the targeting ligand is linked to the 5' terminal end of an expression-inhibiting oligomeric compound not only allows for the linkage of the targeting ligand as the last component (thus reducing manufacturing costs), as well as potentially permits the targeting ligand to block the loading of the sense strand into RISC when the targeting ligand is attached to the 5' terminal end of the sense strand of a double-stranded RNAi agent. When an expression-inhibiting oligomeric compound is a double-stranded RNAi agent, the targeting ligand can be prepared as a phosphoramidite compound when the targeting ligand is to be linked to the 5' terminal end of the sense strand of the RNAi agent.

In some embodiments, the targeting ligand is represented by the following Formula B:

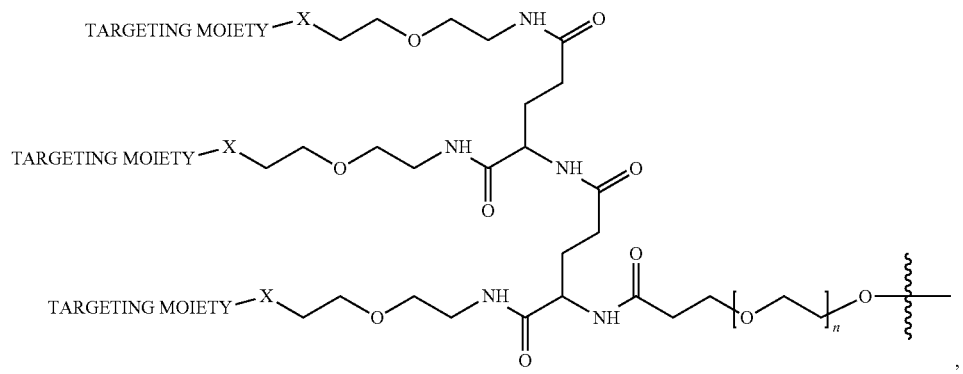

wherein n is an integer from 1 to 20; X is O, S, or NH; and Targeting Moiety is selected from the group consisting of galactose, galactosamine, N-formyl-galactosamine, N-acetyl-galactosamine, N-propionyl-galactosamine, N-n-butanoylgalactosamine, or N-iso-butanoylgalactosamine. (Formula B). In some embodiments, n equals 6. In some embodiments, n equals 8. In some embodiments, n equals 4.

In some embodiments, the targeting ligand has the structure represented by the following:

In some embodiments, the targeting ligand has the structure represented by Structure 1, wherein n=6. In some embodiments, the targeting ligand has the structure represented by Structure 1, wherein n=8. In some embodiments, the targeting ligand has the structure represented by Structure 1, wherein n=4.

In some embodiments, the targeting ligand is linked to an expression-inhibiting oligomeric compound, and has the structure represented by the following:

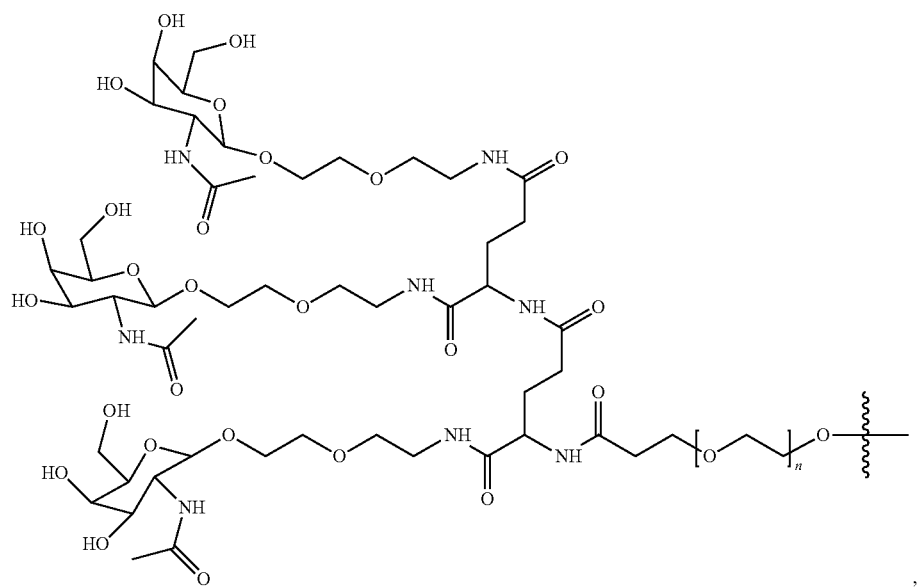

wherein n is an integer from 1 to 20 (e.g., 1, 2, 3, 4, 5, 6, 7, 8, 9, 10, 11, 12, 13, 14, 15, 16, 17, 18, 19, or 20) (Structure 1).

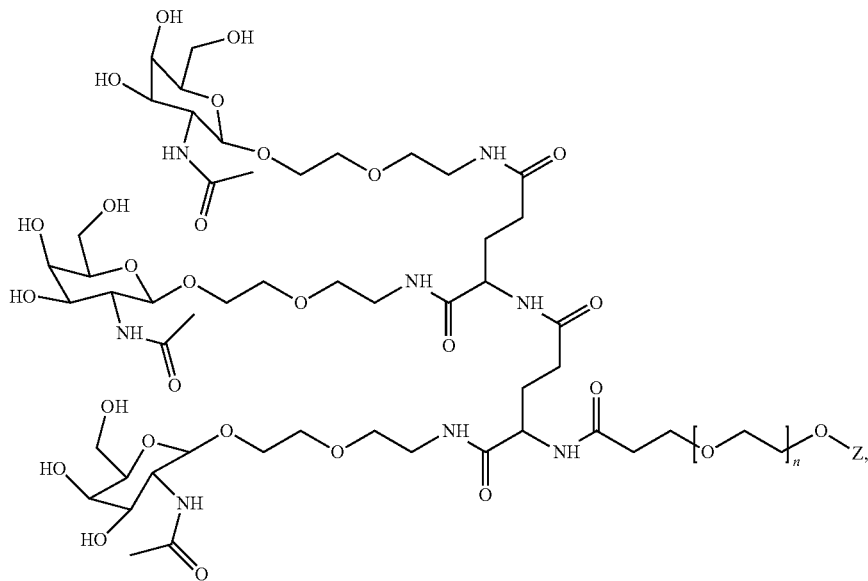

wherein Z includes or consists of an expression-inhibiting oligomeric compound (Structure 1a).

In some embodiments, the targeting ligand is linked to an expression-inhibiting oligomeric compound, and has the structure represented by the following:

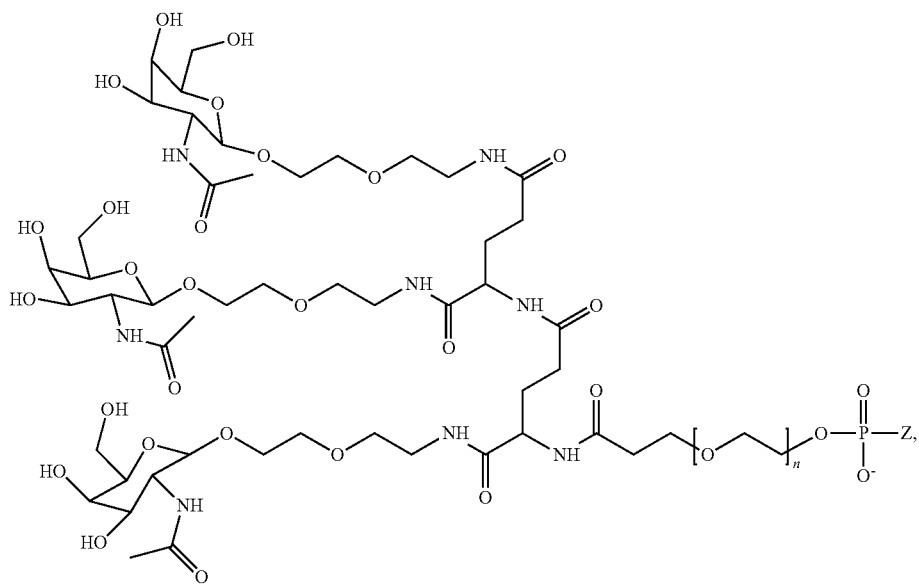

wherein Z consists of or includes an expression-inhibiting oligomeric compound (Structure 1b).

In some embodiments, the targeting ligand is linked to an expression-inhibiting oligomeric compound, and has the structure represented by the following:

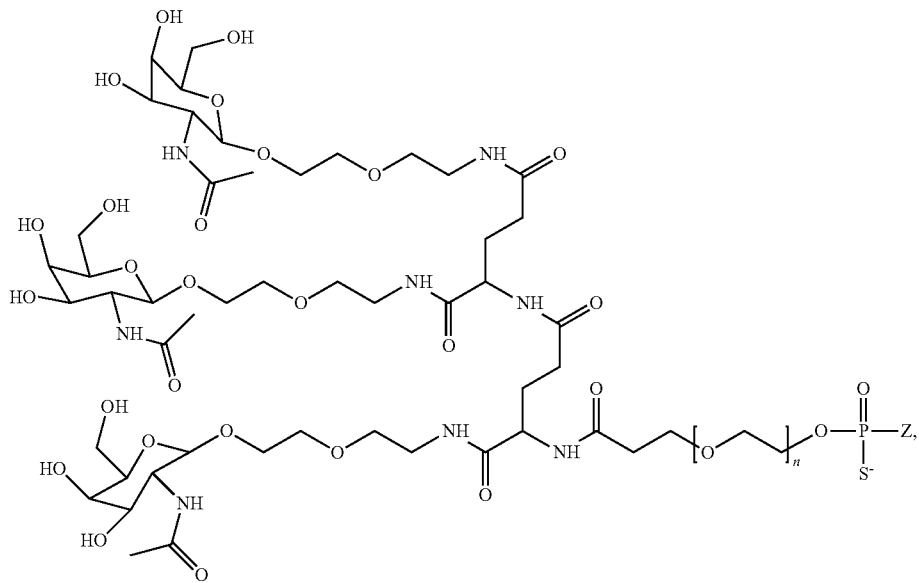

wherein Z consists of or includes an expression-inhibiting oligomeric compound (Structure 1c).

In some embodiments, the targeting ligand is a phosphoramidite-containing compound having the structure represented by the following:

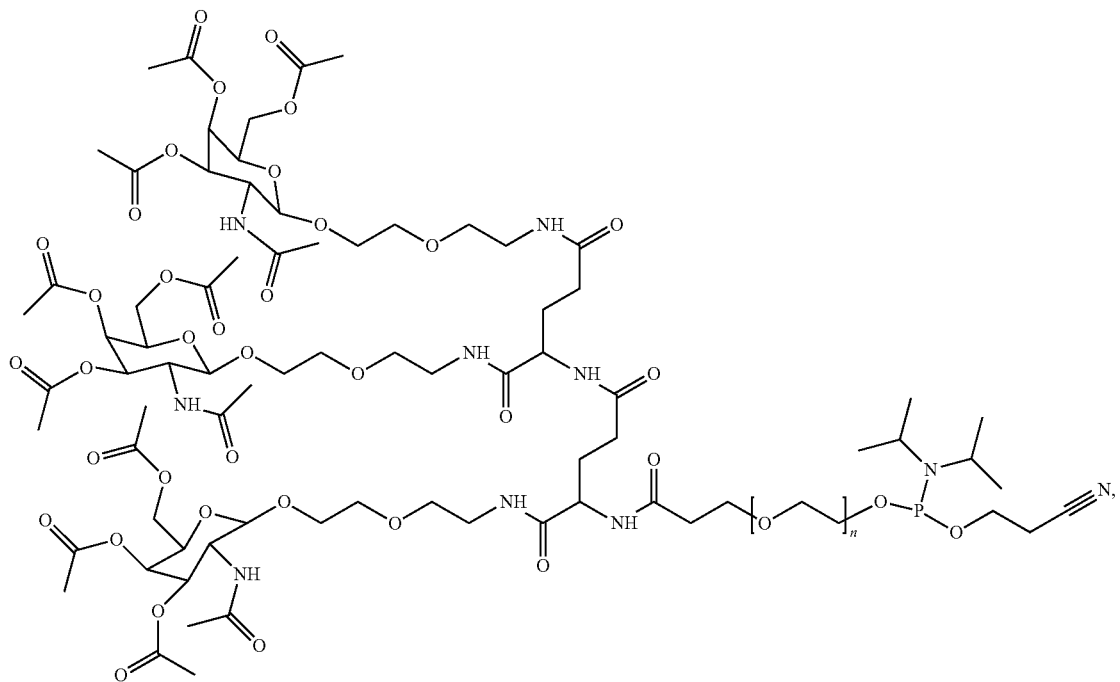

wherein n is an integer from 1 to 20 (e.g., 1, 2, 3, 4, 5, 6, 7, 8, 9, 10, 11, 12, 13, 14, 15, 16, 17, 18, 19, or 20) (Structure 1d).

In some embodiments, the targeting ligand comprises or consists of the structure represented by the following:

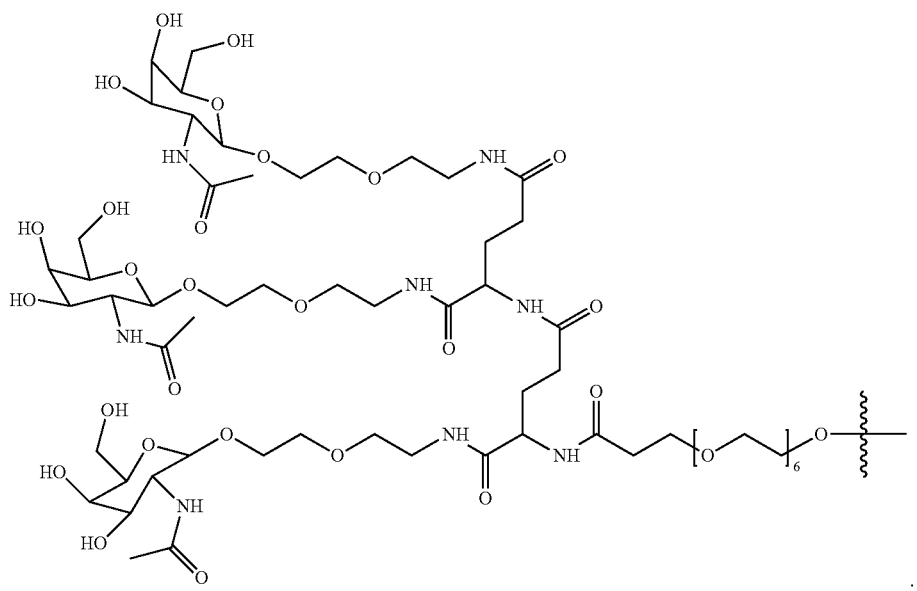

(Structure 101)

In some embodiments, the targeting ligand is linked to an expression-inhibiting oligomeric compound, and has the structure represented by the following:

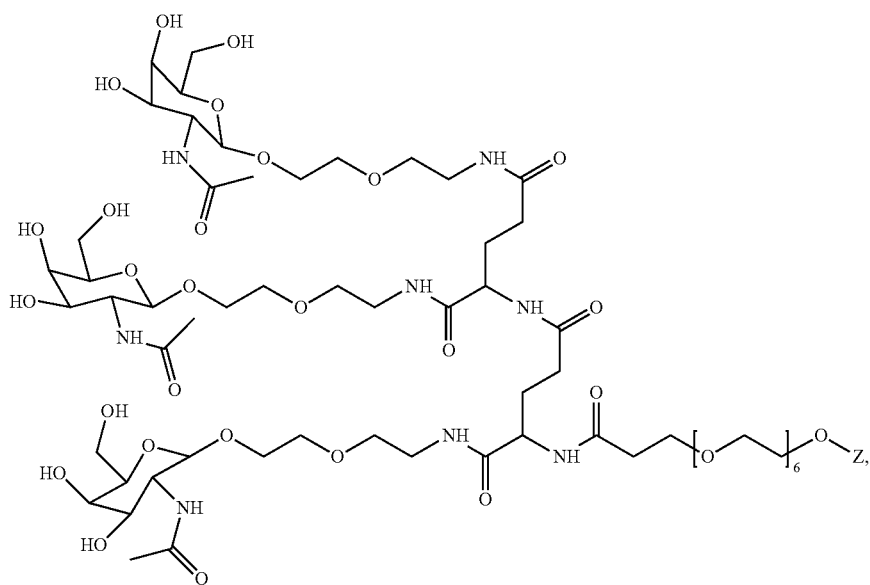

wherein Z includes or consists of an expression-inhibiting oligomeric compound (Structure 101a).

In some embodiments, the targeting ligand is linked to an expression-inhibiting oligomeric compound, and has the structure represented by the following:

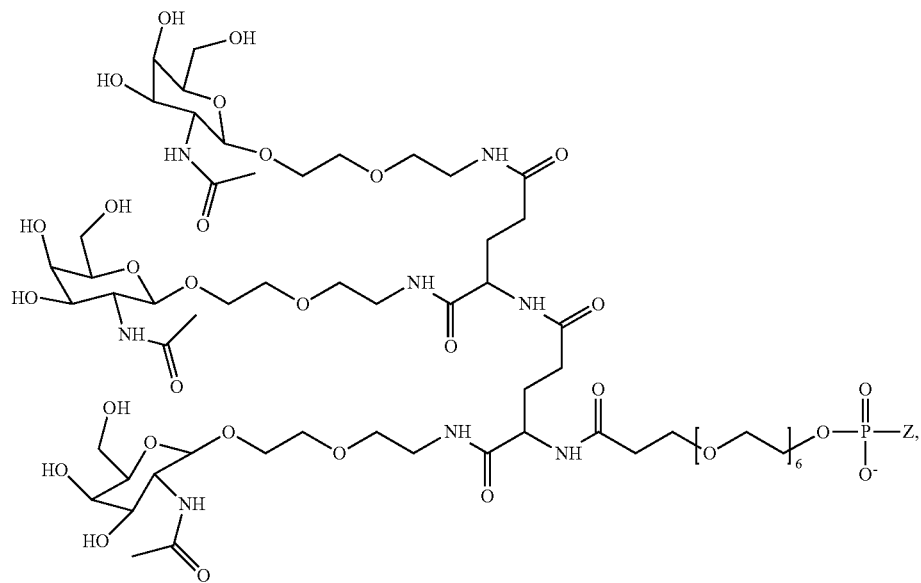

wherein Z consists of or includes an expression-inhibiting oligomeric compound (Structure 101b).

In some embodiments, the targeting ligand is linked to an expression-inhibiting oligomeric compound, and has the structure represented by the following:

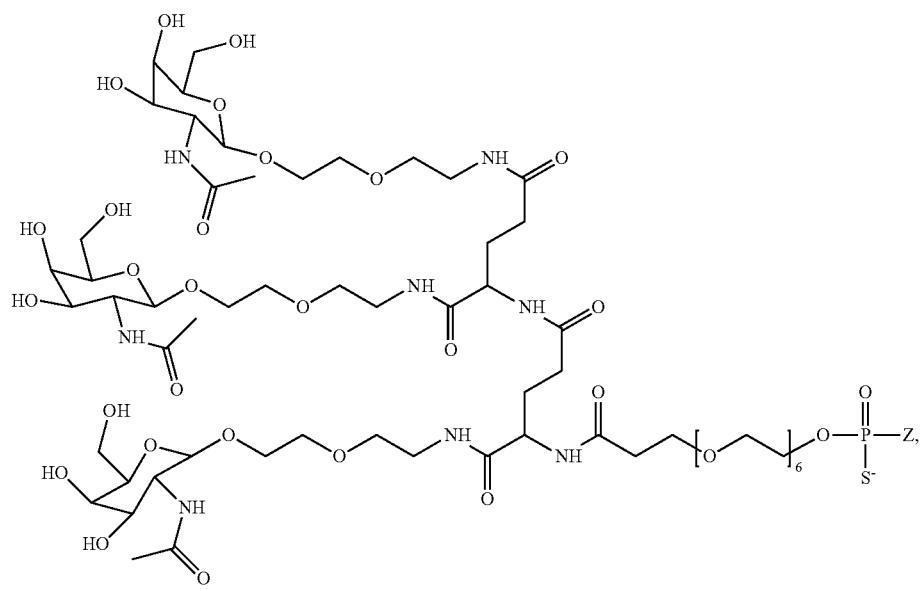

wherein Z consists of or includes an expression-inhibiting oligomeric compound (Structure 101c).

In some embodiments, the targeting ligand is a phosphoramidite-containing compound having the structure represented by the following:

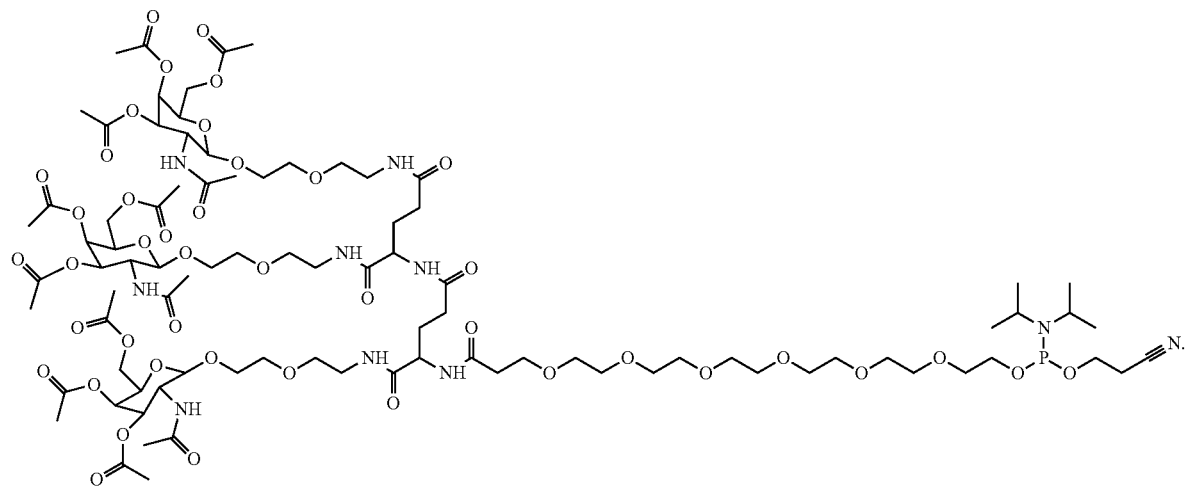
(Structure 101d)
In some embodiments, the targeting ligand comprises or consists of the structure represented by the following:
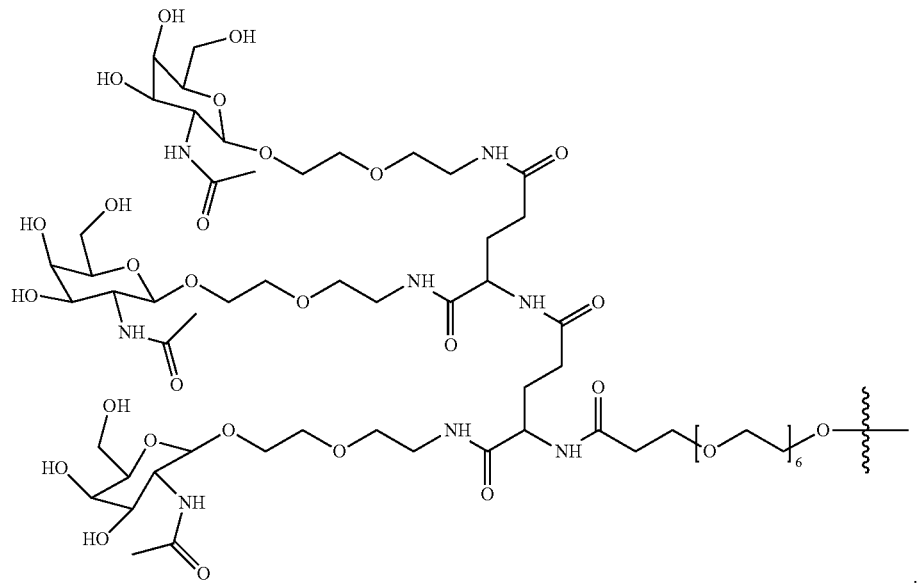
(Structure 102)
In some embodiments, the targeting ligand is linked to an expression-inhibiting oligomeric compound, and has the structure represented by the following:

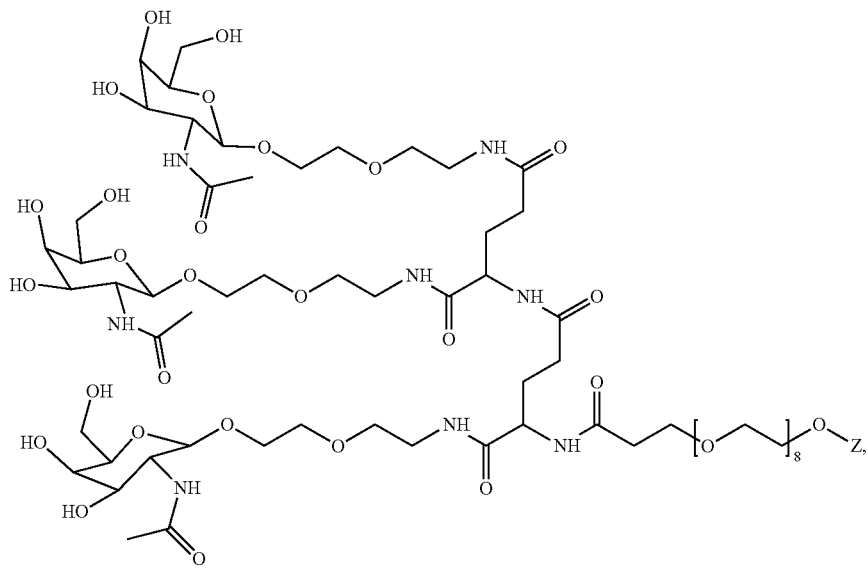

wherein Z includes or consists of an expression-inhibiting oligomeric compound (Structure 102a).

In some embodiments, the targeting ligand is linked to an expression-inhibiting oligomeric compound, and has the structure represented by the following:

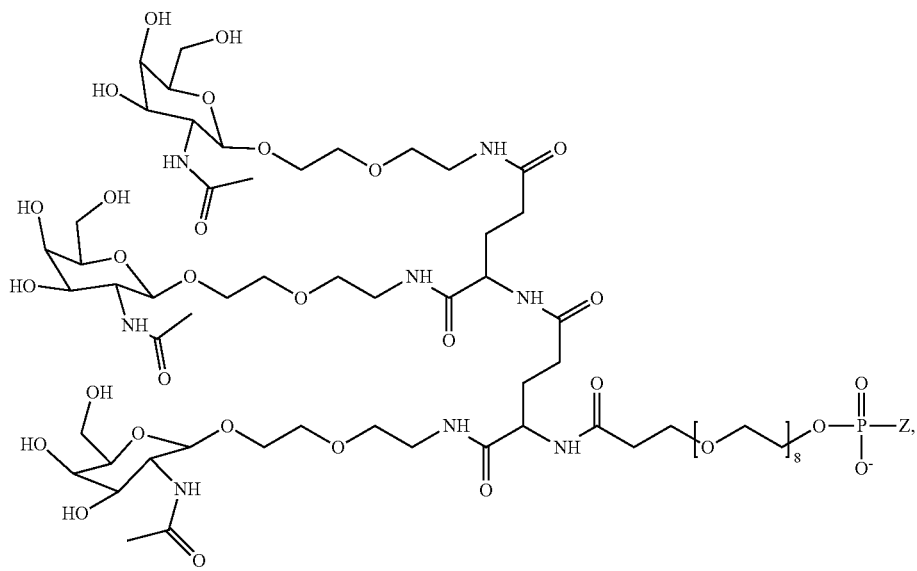

wherein Z consists of or includes an expression-inhibiting oligomeric compound (Structure 102b).

In some embodiments, the targeting ligand is linked to an expression-inhibiting oligomeric compound, and has the structure represented by the following:

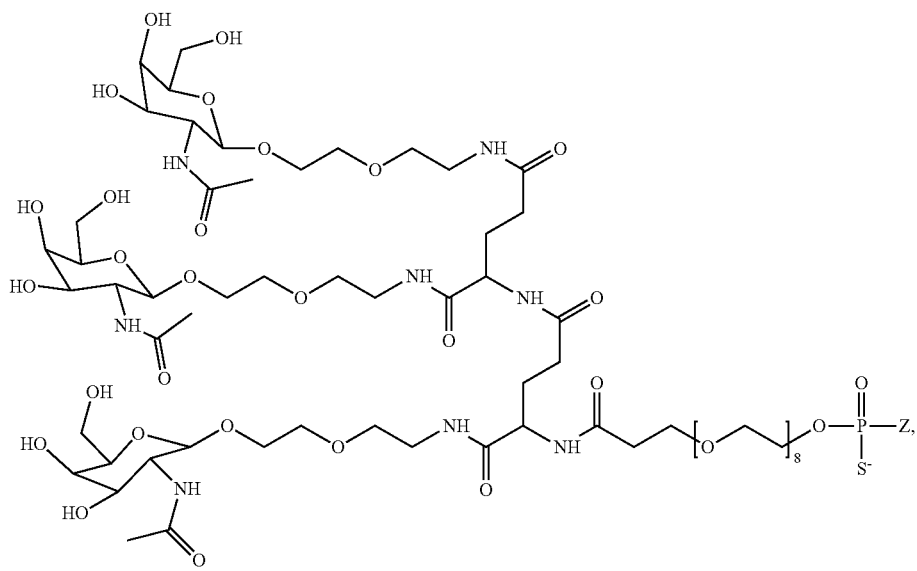
wherein Z consists of or includes an expression-inhibiting oligomeric compound (Structure 102c).
In some embodiments, the targeting ligand is a phosphoramidite-containing compound having the structure represented by the following:

(Structure 102d)
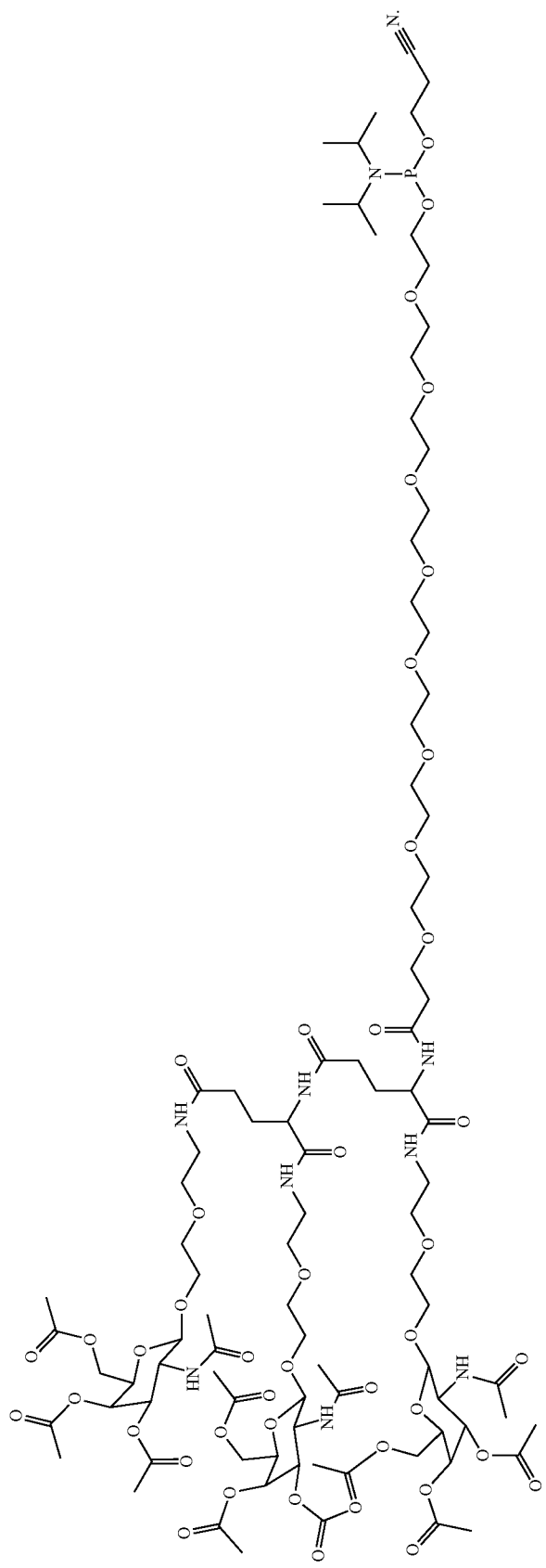

In some embodiments, the targeting ligand comprises or consists of the structure represented by the following:

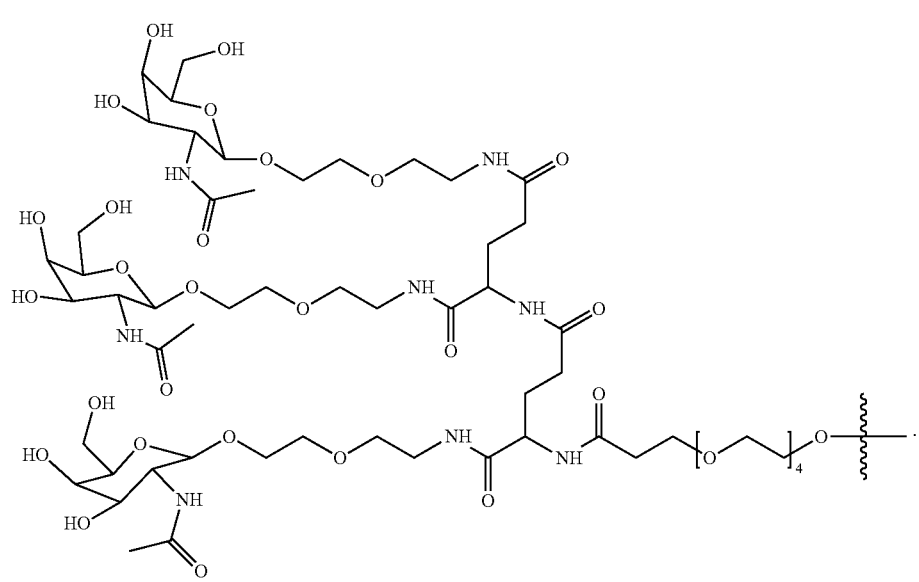

(Structure 103)

In some embodiments, the targeting ligand is linked to an expression-inhibiting oligomeric compound, and has the structure represented by the following:

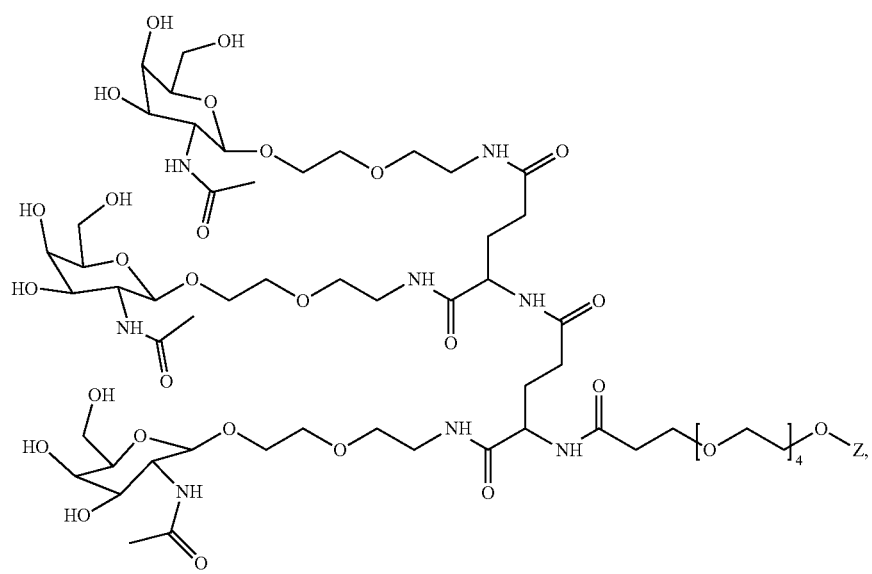

wherein Z includes or consists of an expression-inhibiting oligomeric compound (Structure 103a).

In some embodiments, the targeting ligand is linked to an expression-inhibiting oligomeric compound, and has the structure represented by the following:

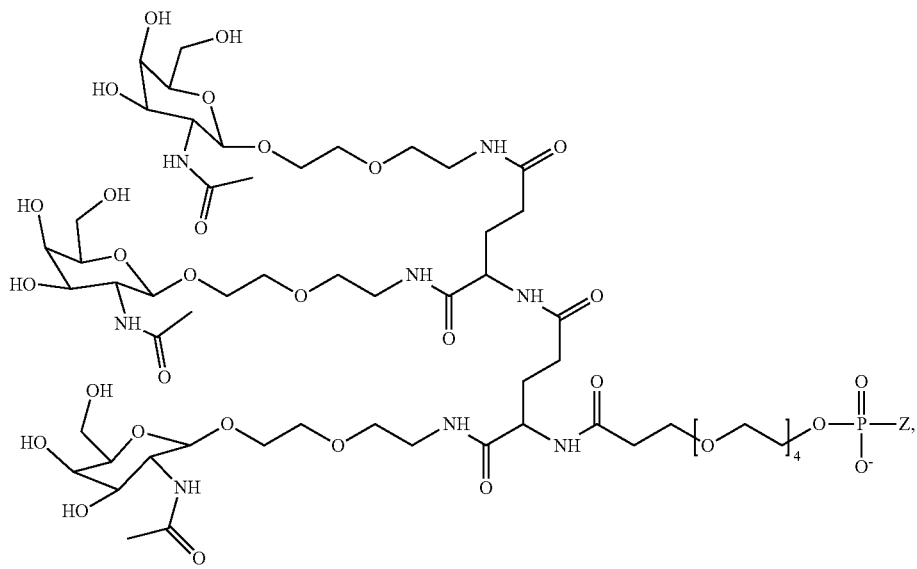

wherein Z consists of or includes an expression-inhibiting oligomeric compound (Structure 103b).

In some embodiments, the targeting ligand is linked to an expression-inhibiting oligomeric compound, and has the structure represented by the following:

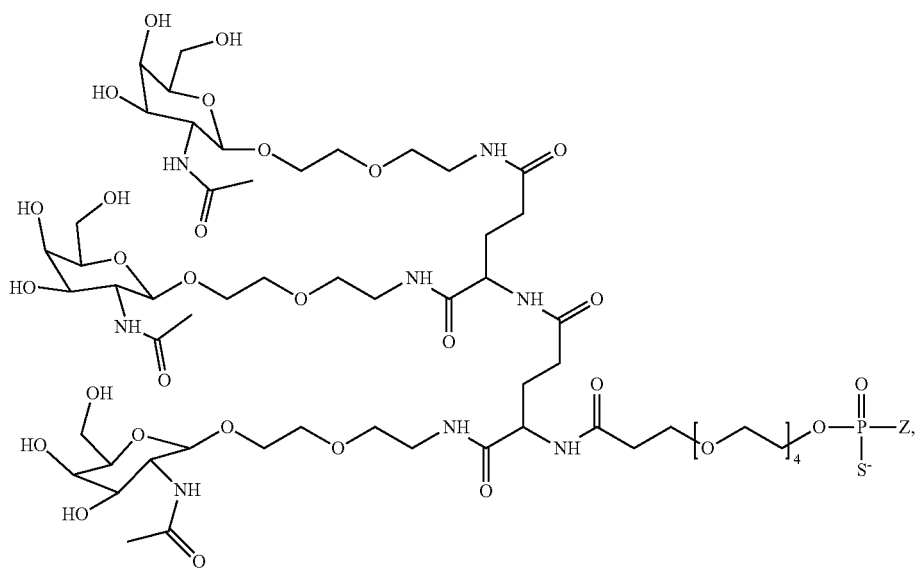

wherein Z consists of or includes an expression-inhibiting oligomeric compound (Structure 103c).

In some embodiments, the targeting ligand is a phosphoramidite-containing compound having the structure represented by the following:

(Structure 103d)
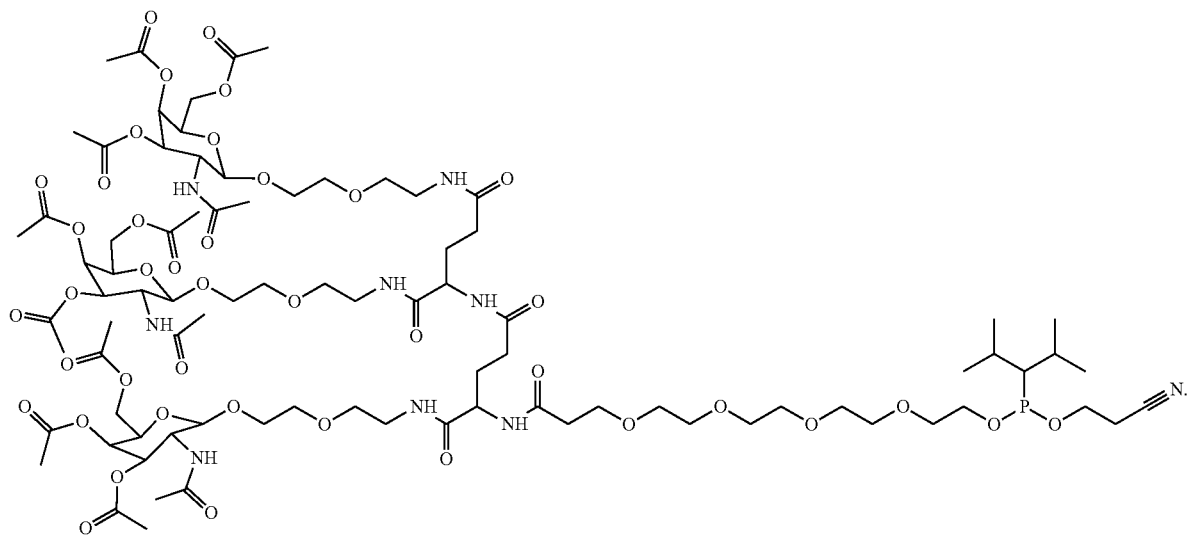
In some embodiments, the targeting ligand has the structure represented by the following:
(Structure 2)
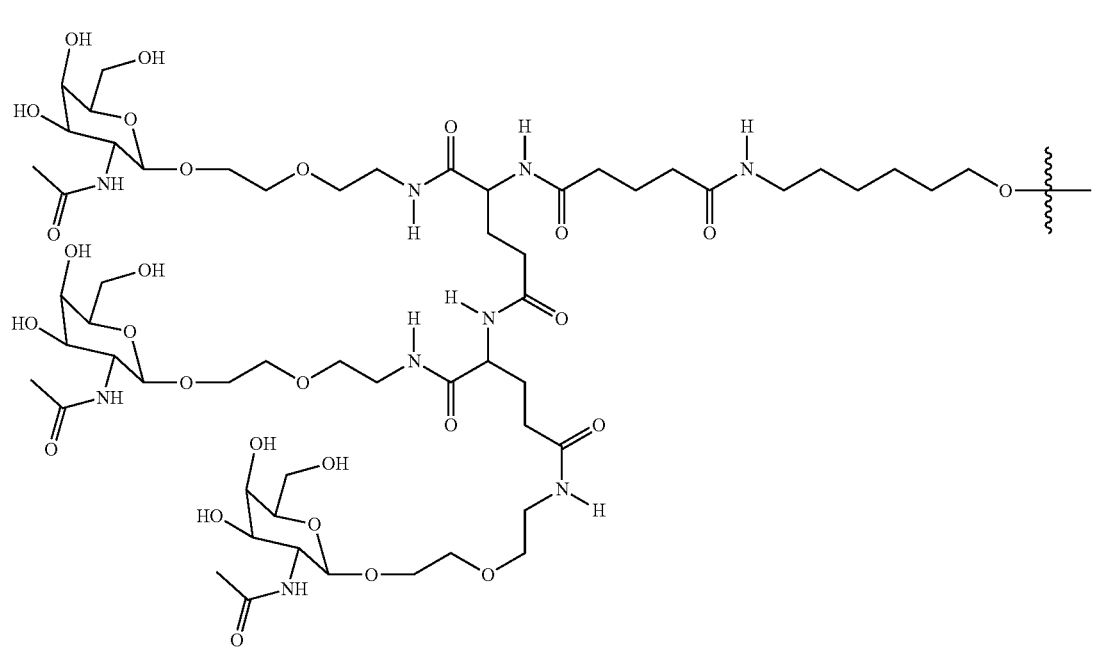
In some embodiments, an expression-inhibiting oligomeric compound is linked to the targeting ligand and has the structure represented by the following:

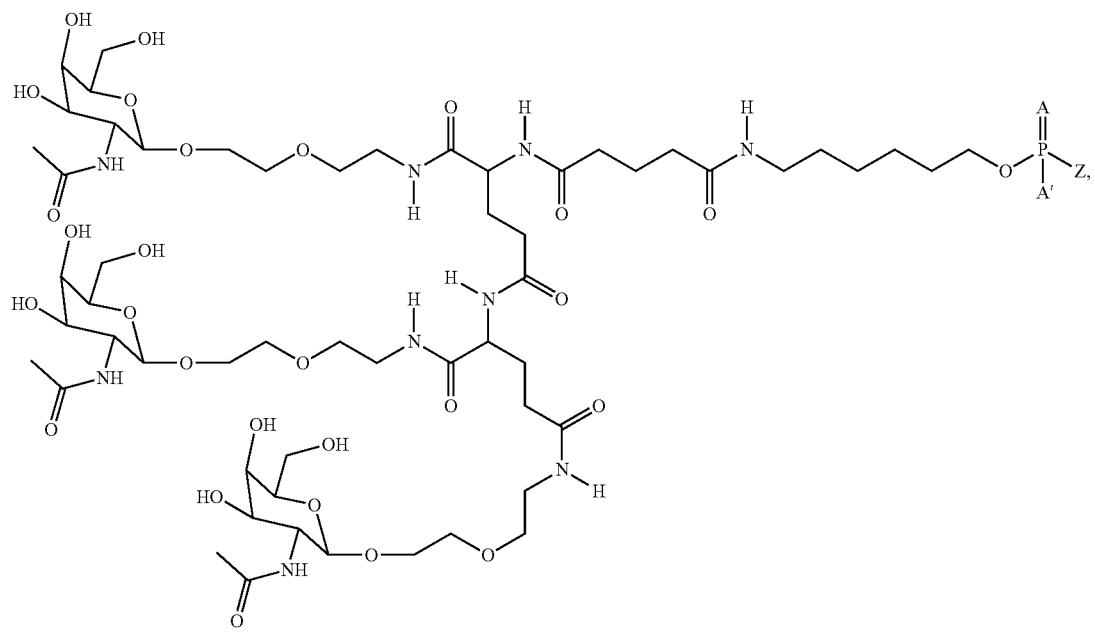
wherein Z consists of or includes an expression-inhibiting oligomeric compound; A is O or S; and A' is O⁻, S⁻, or NH⁻ (Structure 2b).
In some embodiments, the targeting ligand is a phosphoramidite-containing compound having the structure represented by the following:
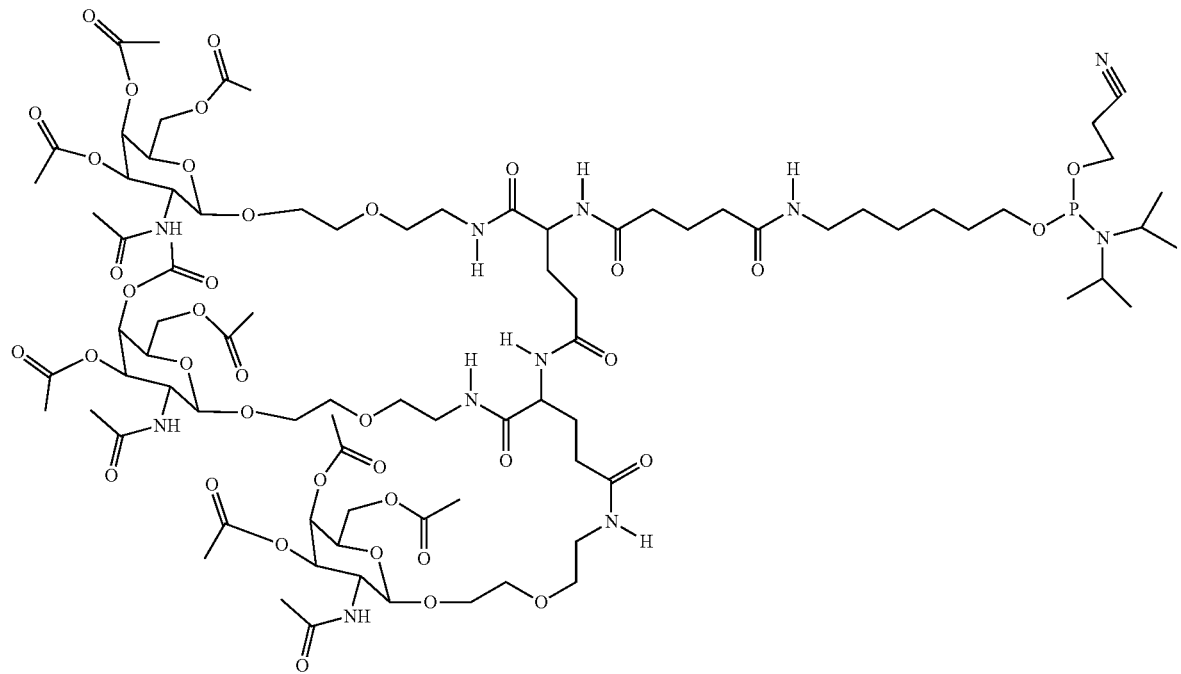
(Structure 2d)

In some embodiments, the targeting ligand has the structure represented by the following:

(Structure 3)

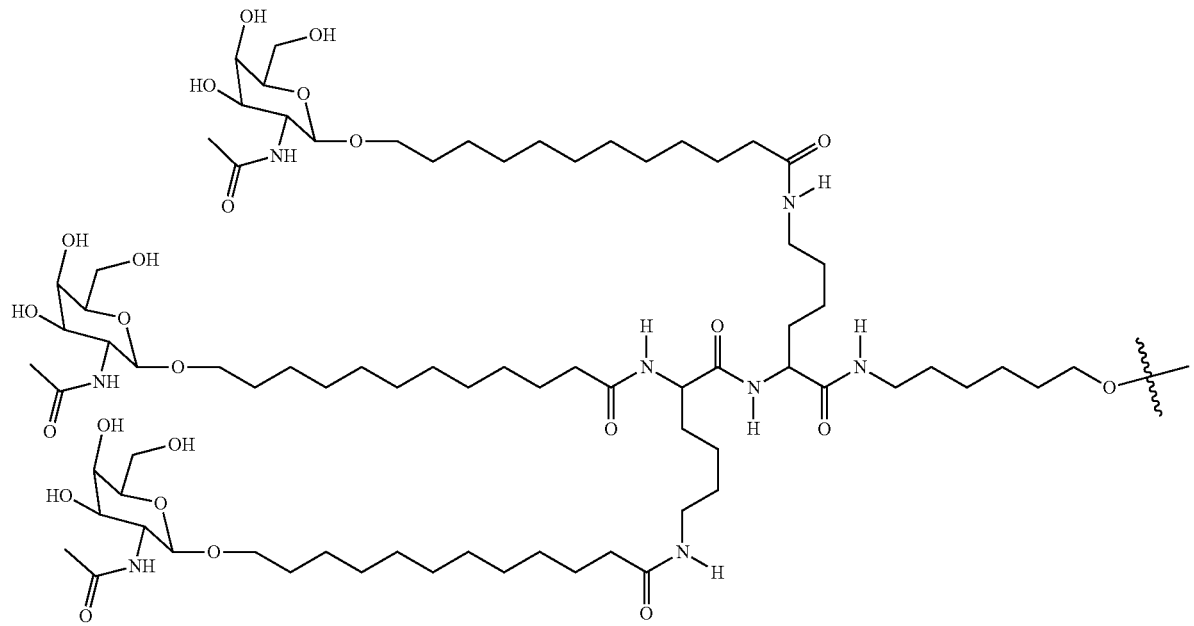

In some embodiments, an expression-inhibiting oligomeric compound is linked to the targeting ligand and has the structure represented by the following:

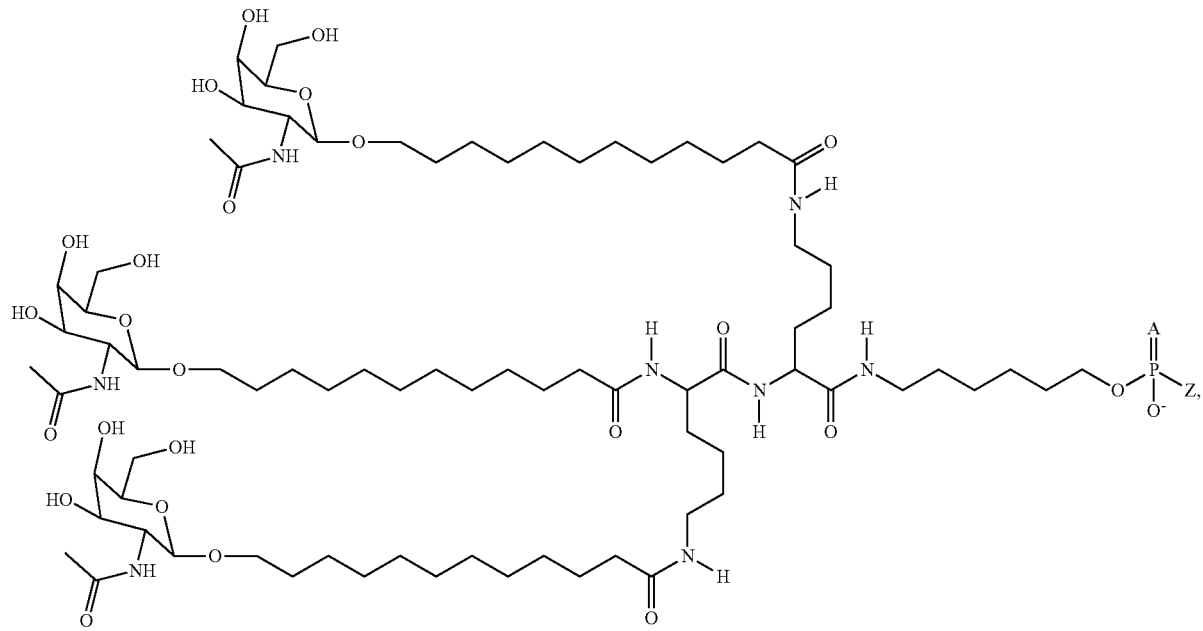

wherein Z consists of or includes an expression-inhibiting oligomeric compound; A is O or S; and A' is O⁻, S⁻, or NH⁻ (Structure 3b).

In some embodiments, the targeting ligand is a phosphoramidite-containing compound having the structure represented by the following:

(Structure 3d)
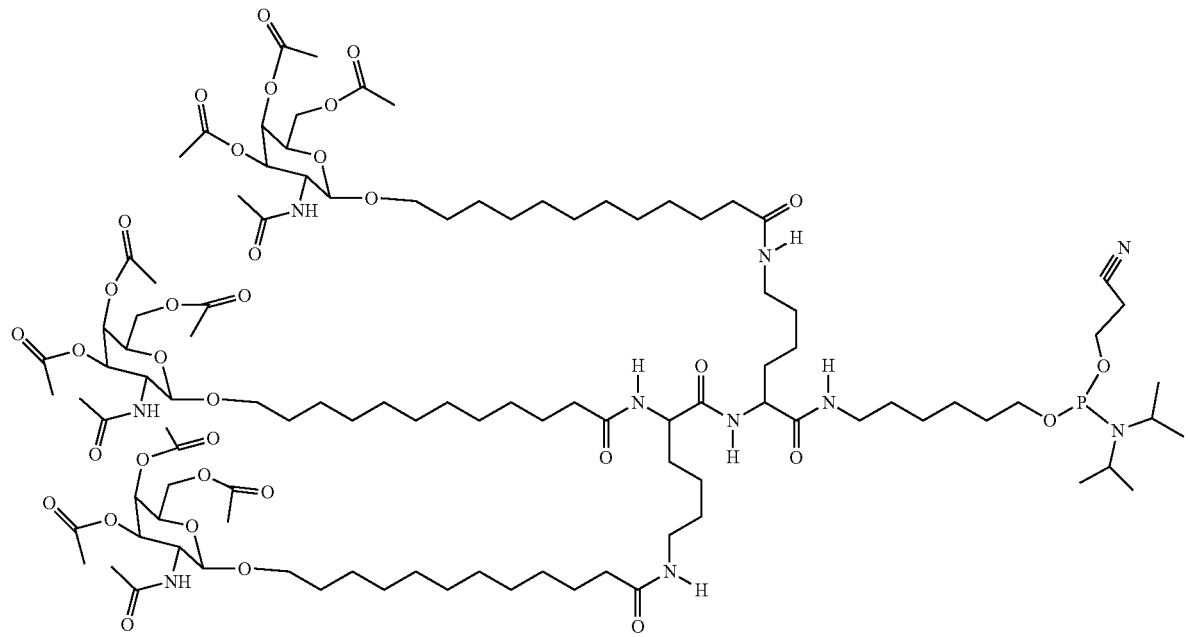
In some embodiments, the targeting ligand has the structure represented by the following:
(Structure 4)
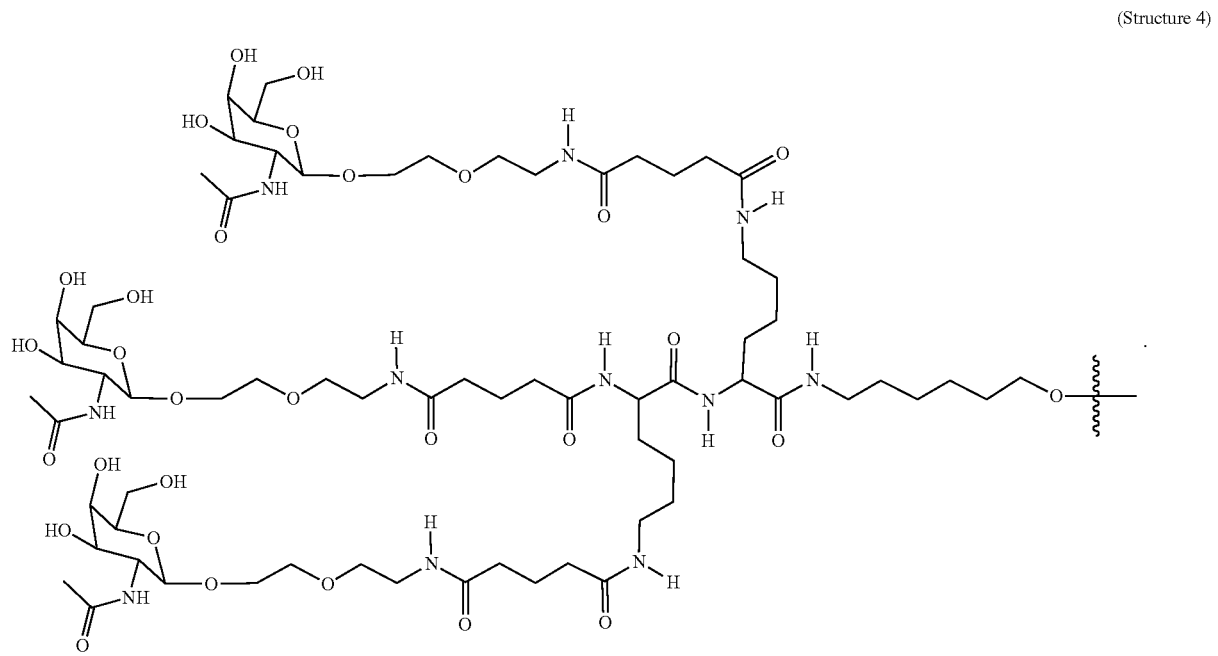 [SMILES: *OCCCCCCNC(=O)C(CCCCNC(=O)CCCC(=O)NCCOCCOC1OC(CO)C(O)C(O)C1NC(C)=O)NC(=O)C(CCCCNC(=O)CCCC(=O)NCCOCCOC1OC(CO)C(O)C(O)C1NC(C)=O)NC(=O)CCCC(=O)NCCOCCOC1OC(CO)C(O)C(O)C1NC(C)=O]
In some embodiments, an expression-inhibiting oligomeric compound is linked to the targeting ligand and has the structure represented by the following:

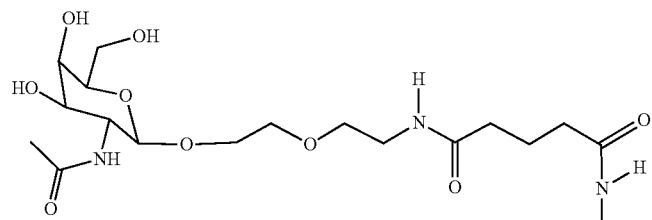
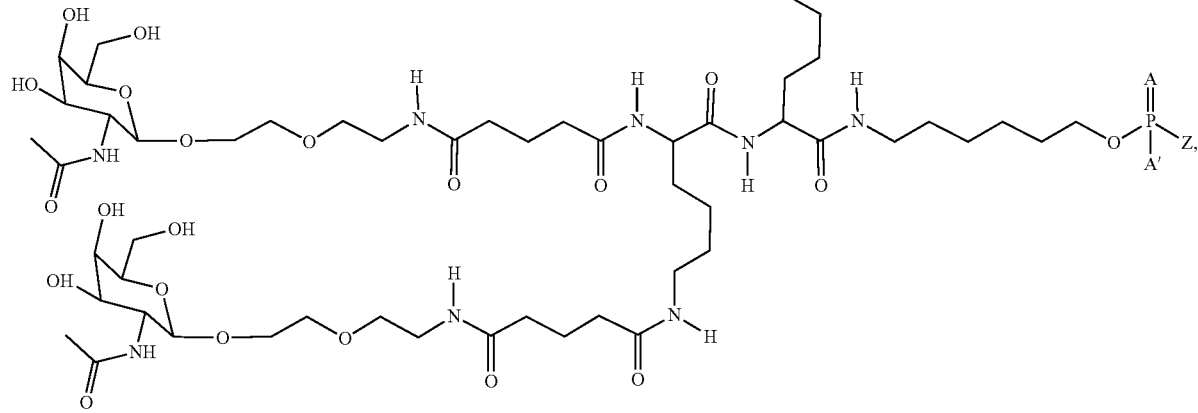

wherein Z consists of or includes an expression-inhibiting oligomeric compound; A is O or S; and A' is O⁻, S⁻, or NH⁻ (Structure 4b).

In some embodiments, the targeting ligand is a phosphoramidite-containing compound having the structure represented by the following:

(Structure 4d)

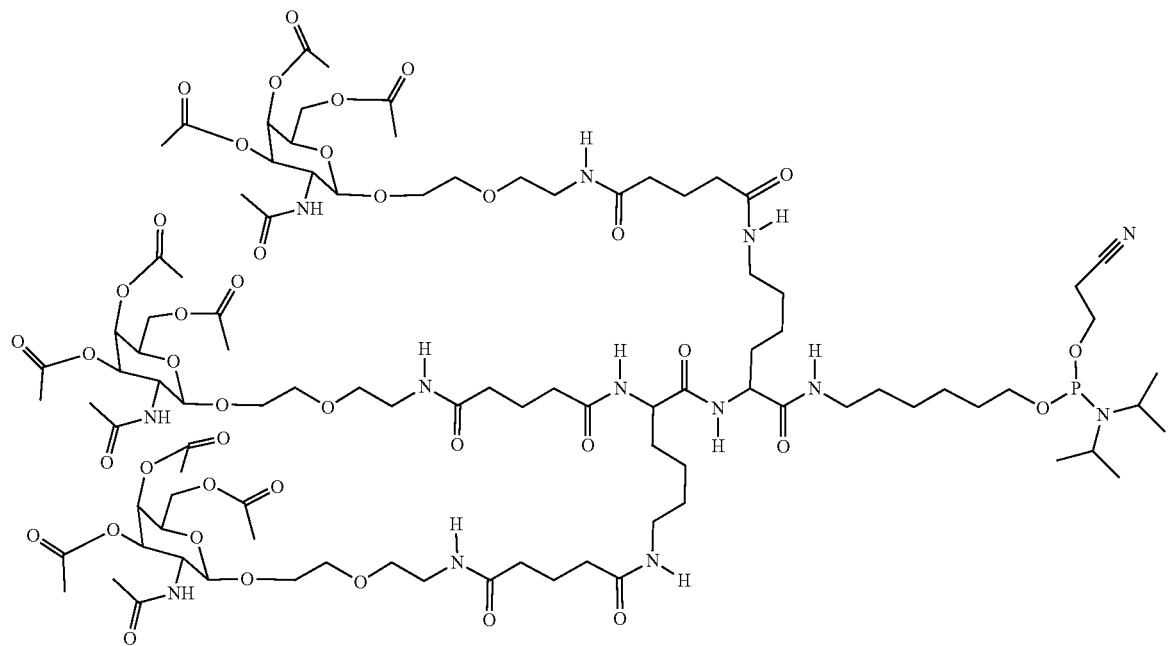

In some embodiments, the targeting ligand has the structure represented by the following:

(Structure 5)

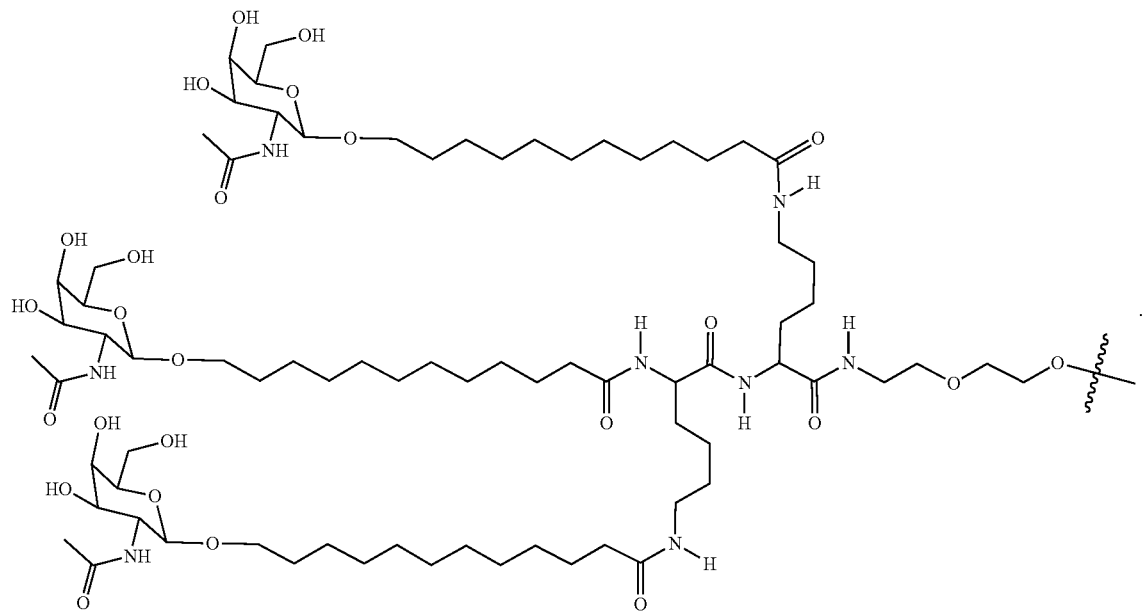

In some embodiments, an expression-inhibiting oligomeric compound is linked to the targeting ligand and has the structure represented by the following:

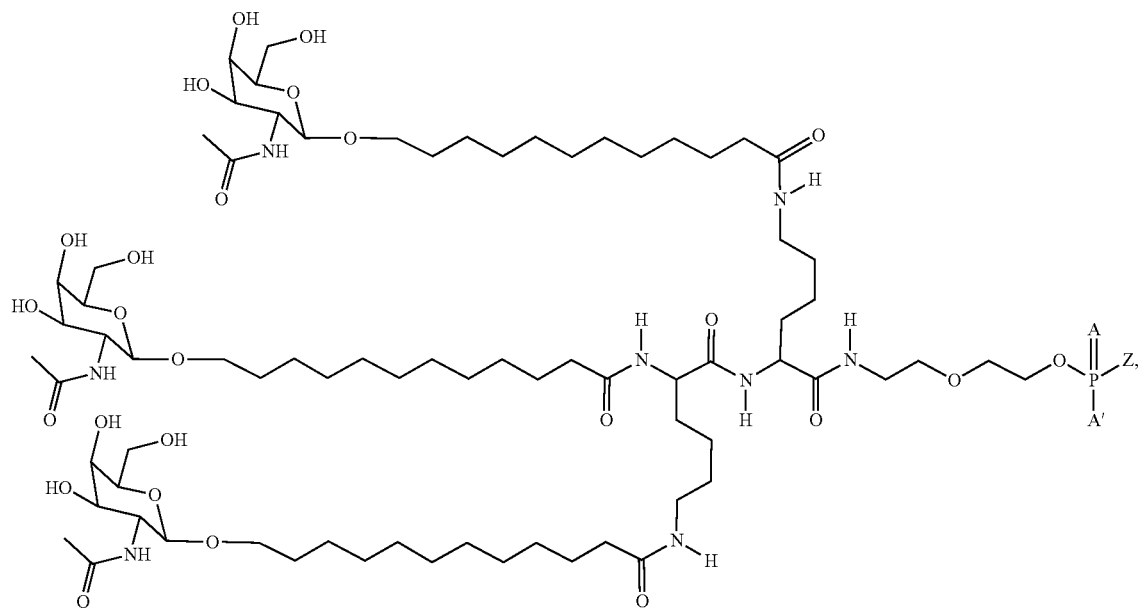

wherein Z consists of or includes an expression-inhibiting oligomeric compound; A is O or S; and A' is O⁻, S⁻, or NH⁻ (Structure 5b).

In some embodiments, the targeting ligand is a phosphoramidite-containing compound having the structure represented by the following:

(Structure 5d)
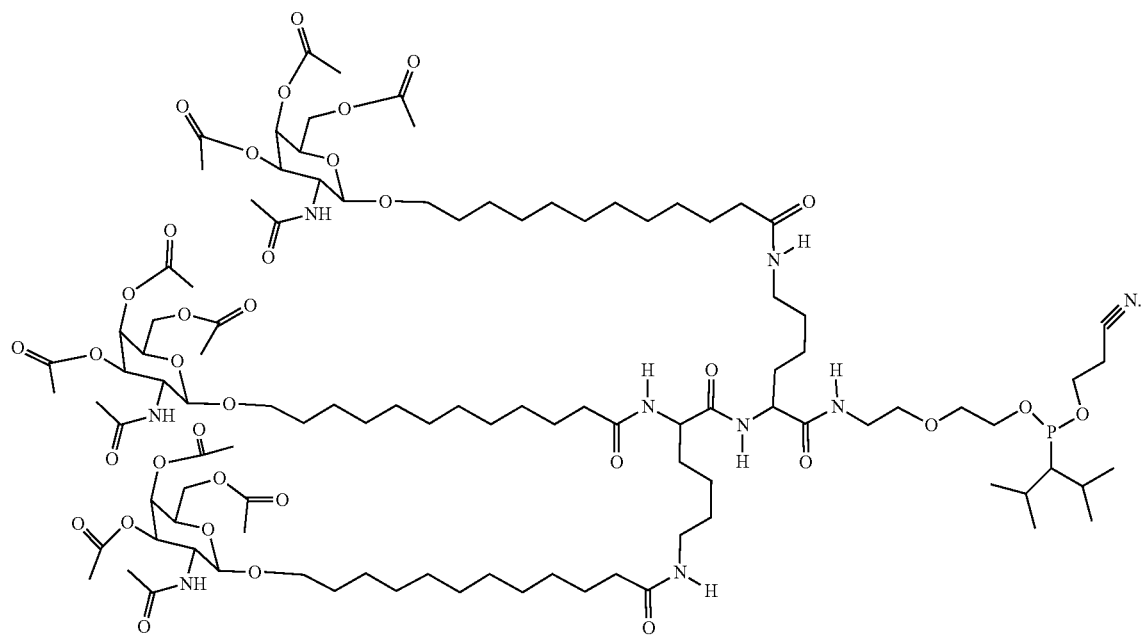
In some embodiments, the targeting ligand has the structure represented by the following:
(Structure 6)
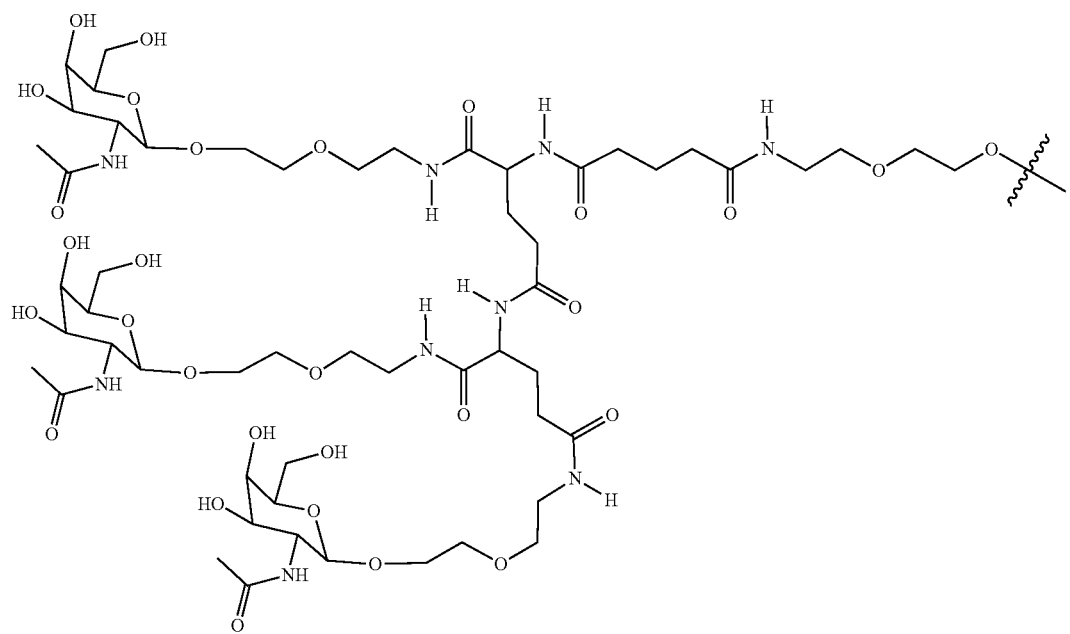
In some embodiments, an expression-inhibiting oligomeric compound is linked to the targeting ligand and has the structure represented by the following:

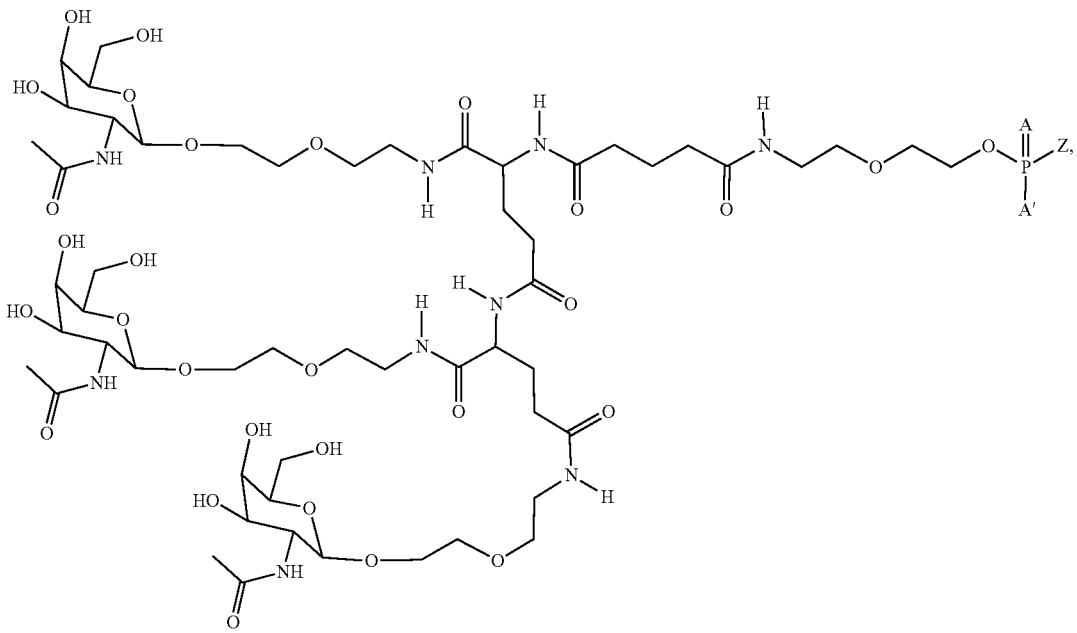

wherein Z consists of or includes an expression-inhibiting oligomeric compound; A is O or S; and A' is O⁻, S⁻, or NH⁻ (Structure 6b).

In some embodiments, the targeting ligand is a phosphoramidite-containing compound having the structure represented by the following:

In some embodiments, the targeting ligand is in the form of a galactose cluster. As used herein, a galactose cluster includes a targeting ligand having two to four terminal galactose derivatives.

As used herein, the term galactose derivative includes both galactose and derivatives of galactose having affinity (Structure 6d)

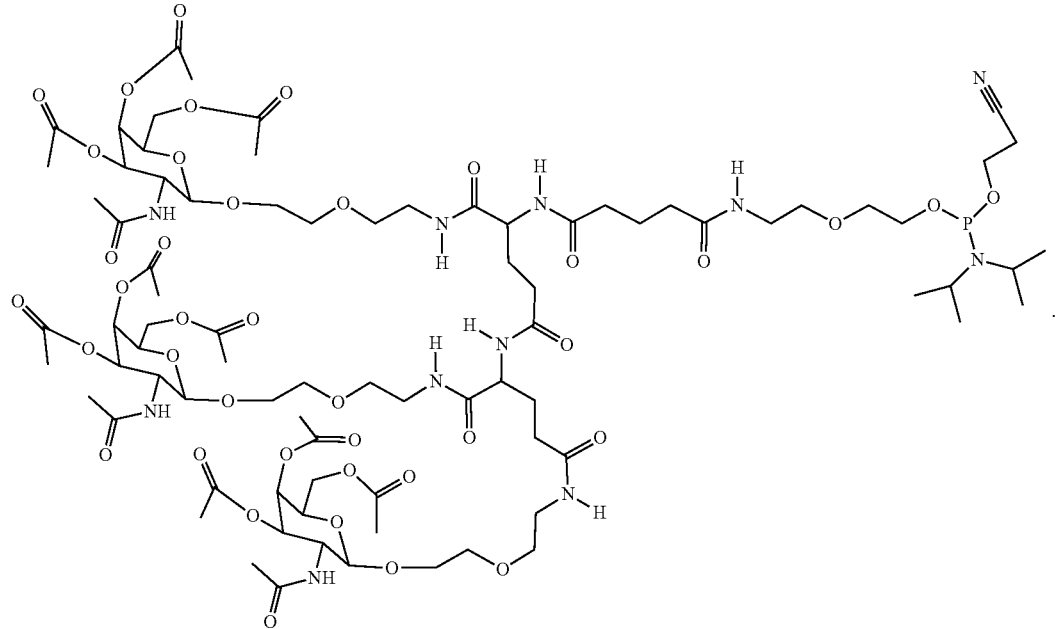

for the asialoglycoprotein receptor equal to or greater than that of galactose. A galactose derivative is a saccharide sugar that is a type of targeting moiety. A terminal galactose derivative may be linked to a tether through the C-1 carbon of the saccharide.

In some embodiments, the targeting ligand is comprised of three terminal galactosamines or galactosamine derivatives (such as N-acetyl-galactosamine) each having affinity for the asialoglycoprotein receptor. In some embodiments, the targeting ligand includes three terminal N-acetyl-galactosamines (GalNAc or NAG) as the targeting moieties.

In some embodiments, the targeting ligand is comprised of four terminal galactosamines or galactosamine derivatives (such as N-acetyl-galactosamine) each having affinity for the asialoglycoprotein receptor. In some embodiments, the targeting ligand includes four terminal N-acetyl-galactosamines (GalNAc or NAG) as the targeting moieties.

In some embodiments, each targeting moiety includes a galactosamine derivative that is N-acetyl-galactosamine. Other saccharides having affinity for the asialoglycoprotein receptor that may be used as targeting moieties may be selected from the list including: galactose, galactosamine, N-formyl-galactosamine, N-acetyl-galactosamine, N-propionyl-galactosamine, N-n-butanoylgalactosamine, and N-iso-butanoylgalactosamine. The affinities of numerous galactose derivatives for the asialoglycoprotein receptor have been studied (see for example: Iobst, S. T. and Drickamer, K. *J. B. C.* 1996, 271, 6686) or are readily determined using methods well known and commonly used in the art.

Terms commonly used in the art when referring to three terminal N-acetyl-galactosamines include tri-antennary, tri-valent, and trimer.

Linkers

The targeting ligands disclosed herein comprise a linker.

The linker is a group of atoms linked to a branch point group on one end, and linked to a therapeutic compound (or to the phosphorus atom of a phosphoramidite through a phosphitylation reaction with a phosphoramidite forming reagent, when the targeting ligand is synthesized as a phosphoramidite compound) on the other end. In some embodiments, the linker is linked to a branch point group on one end, and is ligated on the other end to a group or groups that are then ligated to an expression-inhibiting oligomeric compound. In some embodiments, the linker is directly linked to an oligomeric compound. In some embodiments, the linker is linked to a cleavable moiety, which is then linked to an oligomeric compound. Examples of cleavable moieties include, for example, phosphate groups, groups including a disulfide moiety, and/or other internucleoside linkages that may be cleaved. In some embodiments, the linker is not linked to a cleavable moiety. In some embodiments, the linker is linked to a phosphorothioate or phosphonate group.

In some embodiments, the linker consists of or includes a polyethylene glycol ("PEG") moiety. Incorporating a PEG moiety into the linker confers certain beneficial properties over certain other linkers, such as linkers that consist of or include substituted or unsubstituted alkyl chains.

For example, incorporating a PEG moiety into the linker increases the solubility of the targeting ligand-containing phosphoramidite compound in solvents commonly used in nucleotide synthesis as compared to compounds that contain alkyl chain linkers, which can lead to simplified manufacturing processes.

In some embodiments, a targeting ligand comprises a linker having the following structure:

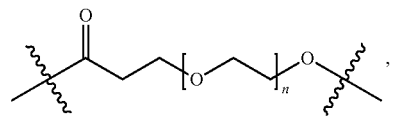

wherein n is an integer from 1 to 20 (e.g., 1, 2, 3, 4, 5, 6, 7, 8, 9, 10, 11, 12, 13, 14, 15, 16, 17, 18, 19, or 20) (Structure 1001).

In some embodiments, a targeting ligand comprises a linker linked to a phosphate group having the following structure:

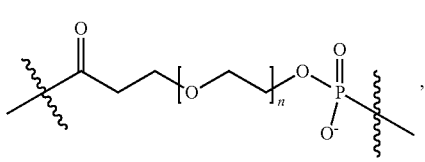

wherein n is an integer selected from 1 to 20. (Structure 1002).

In some embodiments, a targeting ligand comprises a linker linked to a phosphorothioate group having the following structure:

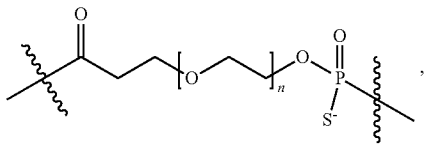

wherein n is an integer selected from 1 to 20 (e.g., 1, 2, 3, 4, 5, 6, 7, 8, 9, 10, 11, 12, 13, 14, 15, 16, 17, 18, 19, or 20) (Structure 1003).

In some embodiments, a targeting ligand comprises a linker having the following structure:

(Structure 1004)

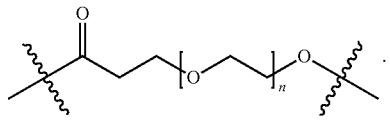

In some embodiments, a targeting ligand comprises a linker linked to a phosphate group having the following structure:

(Structure 1005)

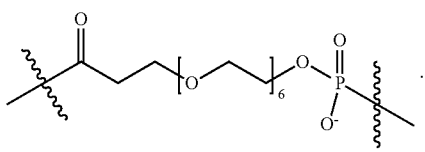

In some embodiments, a targeting ligand comprises a linker linked to a phosphorothioate group having the following structure:

(Structure 1006)

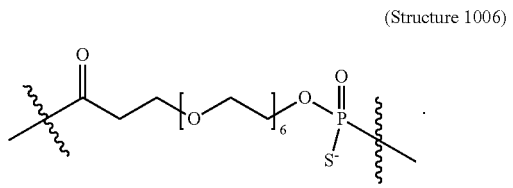

In some embodiments, the linker is linked to an expression-inhibiting oligomeric compound that is a double-stranded RNAi agent. In some embodiments, the linker is linked to the 5' end of the sense strand of a double-stranded RNAi agent. In some embodiments, the linker is linked to the 3' end of the sense strand of a double-stranded RNAi agent. In some embodiments the linker is linked to the 3' end of the antisense strand of a double-stranded RNAi agent. In some embodiments, the linker is linked to the 5' end of the antisense strand of a double-stranded RNAi agent.

In some embodiments, the linker is linked to a cleavable moiety. In some embodiments, a terminal phosphate group of an expression-inhibiting oligomeric compound can serve as a cleavable moiety. In some embodiments, an independently selected cleavable moiety is linked to a linker. As used herein, a cleavable moiety is a group that is stable outside of the cell, but upon entry into the target cell is cleaved. Cleavable moieties are susceptible to cleavage under certain conditions, such as pH, or certain cleavage agents, such as molecules that promote degradation or redox agents.

In some embodiments, the cleavable moiety may be susceptible to pH. For example, endosomes and lysosomes are known to generally have a more acidic pH (pH of approximately 4.5 to 6.5) than human blood (pH of approximately 7.35 to 7.45), and as such may promote the cleavage of a cleavable moiety.

In some embodiments, a cleavable moiety is a phosphate group. Phosphate groups may be cleaved by agents that are known to degrade or hydrolyze phosphate groups.

Branch Point Groups

The targeting ligands disclosed herein comprise at least one branch point group. The branch point group of the targeting ligands disclosed herein is attached to a linker. In some embodiments, the branch point group of the targeting ligands disclosed herein is linked to a linker on one end, and the branch point group is linked to one or more tethers on the other end(s). In some embodiments, the branch point group is attached to a linker and one or more tethers. In some embodiments, the branch point group is attached indirectly (e.g., via the linker) to an expression-inhibiting oligomeric compound. In some embodiments, the branch point group is linked to an expression-inhibiting oligomeric compound via an additional group or groups.

The branch point groups disclosed herein can be of any group which permits attachment of one or more targeting moieties and further permits attachment to a linker.

The branch point groups disclosed herein can be of any group which permits attachment of two, three, or four galactose derivatives and further permits attachment of the branch point to a linker.

In some embodiments, the targeting ligand comprises a branch point having the following structures:

(Structure 2001)

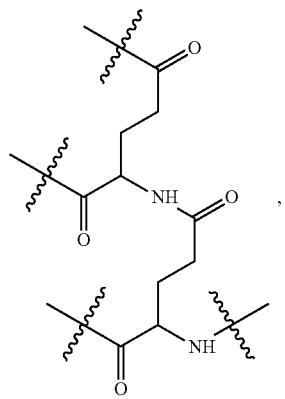

(Structure 2002)

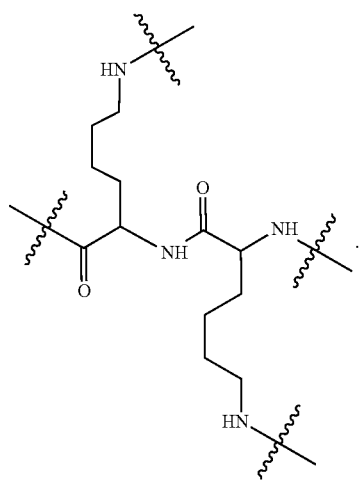

Tethers

The targeting ligands disclosed herein comprise one or more tethers. A tether is linked between the branch point group and each targeting moiety. In some embodiments, the tether is linked directly to the targeting ligand on one end and directly to the branch point group on the other end. In some embodiments, the tether is linked directly to the targeting ligand on one end, and indirectly to the branch point group on the other end. In some embodiments, the tether is linked indirectly to the targeting ligand on one end and indirectly to the branch point group on the other end. In some embodiments, a targeting ligand described herein includes three tethers and three targeting moieties. In some embodiments, a targeting ligand described herein includes four tethers and four targeting moieties. In some embodiments, a targeting ligand described herein includes one tether and one targeting moiety. In some embodiments, a targeting ligand described herein includes multiple tethers and multiple targeting moieties.

In some embodiments, additional tethers or other groups are inserted between the tether and the targeting moiety. In some embodiments, a second tether is inserted between a tether and a targeting moiety. In some embodiments, a second tether and a third tether is inserted between a tether and a targeting moiety. In some embodiments, a second, third, and fourth tether is inserted between a tether and a targeting moiety. As disclosed herein, there is at least one tether present for every targeting moiety. In some embodiments, there is more than one tether present for each targeting moiety. The targeting ligands disclosed herein are intended to cover such compositions.

In some embodiments, additional groups can be inserted between the tether and the branch point group.

As disclosed herein, the tether serves as a spacer that may further add flexibility and/or length to the linkage between the targeting moiety and the branch point group, linker, and therapeutic compound. In some embodiments, the tether includes alkyl groups (including cycloalkyl groups), alkenyl groups (including cycloalkenyl groups), alkynyl groups, aryl groups, aralkyl groups, aralkenyl groups, or aralkynyl groups. In some embodiments, the tether includes one or more heteroatoms, heterocycles, heteroaryls, amino acids, nucleotides, or saccharides.

In some embodiments, the targeting ligand includes a tether having the following structure:

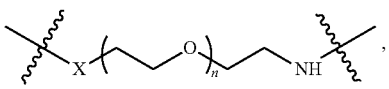

wherein n is an integer from 1 to 20 (e.g., 1, 2, 3, 4, 5, 6, 7, 8, 9, 10, 11, 12, 13, 14, 15, 16, 17, 18, 19 or 20), and X is O, S, or NH (Structure 301).

In some embodiments, the targeting ligand includes a tether having the following structure:

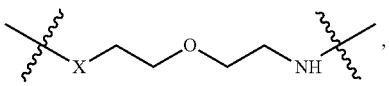

wherein X is O, S, or NH (Structure 302).

In some embodiments, the targeting ligand includes a tether having the following structure:

(Structure 302a)

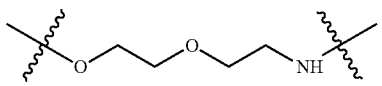

In some embodiments, the targeting ligand includes a tether having the following structure:

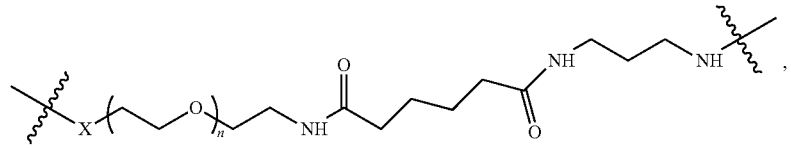

wherein n is an integer from 1 to 20 (e.g., 1, 2, 3, 4, 5, 6, 7, 8, 9, 10, 11, 12, 13, 14, 15, 16, 17, 18, 19 or 20), and X is O, S, or NH. (Structure 303).

In some embodiments, the targeting ligand includes a tether having the following structure:

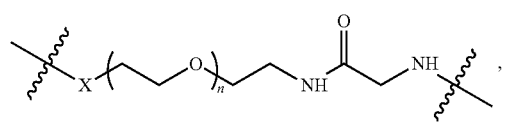

wherein n is an integer from 1 to 20 (e.g., 1, 2, 3, 4, 5, 6, 7, 8, 9, 10, 11, 12, 13, 14, 15, 16, 17, 18, 19 or 20), and X is O, S, or NH. (Structure 304).

In some embodiments, the targeting ligand includes a tether having the following structure:

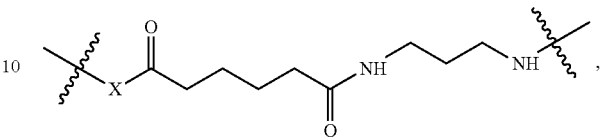

wherein X is O, S, or NH (Structure 305).

In some embodiments, the targeting ligand includes a tether having the following structure:

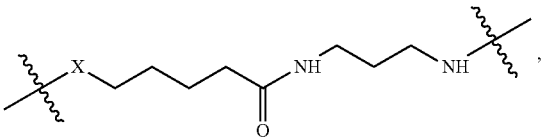

wherein X is O, S, or NH (Structure 306).

In some embodiments, the targeting ligand includes more than one type of tether. In some embodiments, the tether acts as a flexible hydrophilic spacer (See, for example, U.S. Pat. No. 5,885,968; and Biessen et al. *J. Med. Chem.* 1995, 39, 1538-1546, both of which are incorporated herein by reference in their entirety), and includes a PEG spacer. In other embodiments, the PEG spacer has 1 to 20 ethylene units (PEG$_1$ to PEG$_{20}$). For example, the PEG spacer has 1, 2, 3, 4, 5, 6, 7, 8, 9, 10, 11, 12, 13, 14, 15, 16, 17, 18, 19, or 20 ethylene units.

Targeting Moieties:

The targeting ligands disclosed herein can include one to four, or more than four, targeting moieties.

In some embodiments, the targeting ligands may be a galactose cluster. As used herein, a galactose cluster includes a targeting ligand having two to four terminal galactose derivatives. As used herein, the term galactose derivative includes both galactose and derivatives of galactose having affinity for the asialoglycoprotein receptor equal to or greater than that of galactose. A galactose derivative is a saccharide sugar that is a type of targeting moiety. A terminal galactose derivative is linked to a tether through the C-1 carbon of the saccharide.

In some embodiments, the targeting ligand is comprised of three terminal galactosamines or galactosamine derivatives (such as N-acetyl-galactosamine) each having affinity for the asialoglycoprotein receptor. In some embodiments, the targeting ligand includes three terminal N-acetyl-galactosamines (GalNAc or NAG) as the targeting moieties. For example, each of Structures 1, 101, 102, and 103 are targeting ligands having three terminal N-acetyl-galactosamines as the targeting moieties.

In some embodiments, each targeting moiety includes a galactosamine derivative that is N-acetyl-galactosamine. Other saccharides having affinity for the asialoglycoprotein receptor that may be used as targeting moieties may be selected from the list including: galactose, galactosamine, N-formyl-galactosamine, N-propionyl-galactosamine, N-n-butanoylgalactosamine, and N-iso-butanoylgalactosamine. The affinities of numerous galactose derivatives for the asialoglycoprotein receptor have been studied (see, for example, Iobst, S. T. and Drickamer, K. *J. B. C.* 1996, 271, 6686, which is incorporated by reference herein in its entirety) or are readily determined using methods well known and commonly used in the art.

In some embodiments, the targeting moiety is a cell-targeting moiety.

In some embodiments, the targeting moiety includes an N-acetyl-galactosamine:

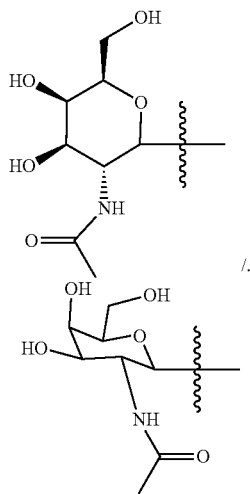

In some embodiments, the targeting ligand includes three targeting moieties. In some embodiments, the targeting ligand includes four targeting moieties. In some embodiments, the targeting ligand includes one targeting moiety. In some embodiments, the targeting ligand includes two targeting moieties. In some embodiments, the targeting ligand includes four or more targeting moieties.

In some embodiments, the targeting moiety includes one or more of galactose, galactosamine, N-formyl-galactosamine, N-acetyl-galactosamine, N-propionyl-galactosamine, N-n-butanoylgalactosamine, or N-iso-butanoylgalactosamine.

For example, in some embodiments, the N-acetyl-galactosamine targeting moieties in any of Structures 1 through 6 can be replaced with alternative targeting moieties. In some embodiments, the N-acetyl-galactosamine targeting moieties in any of Structures 101, 102 or 103 can be replaced with alternative targeting moieties. Such alternative targeting moieties include, for example, galactose, galactosamine, N-formyl-galactosamine, N-acetyl-galactosamine, N-propionyl-galactosamine, N-n-butanoylgalactosamine, or N-iso-butanoylgalactosamine.

Additionally, in some embodiments, the targeting moieties of Structures 1 through 6 may be replaced with, for example, other carbohydrates; glycans; haptens; vitamins; folate; biotin; aptamers; and/or peptides, such as RGD-containing peptides, insulin, EGF, and/or transferrin. In some embodiments, the targeting moieties of Structures 101, 102, or 103 may be replaced with, for example, other carbohydrates; glycans; haptens; vitamins; folate; biotin; aptamers; and/or peptides, such as RGD-containing peptides, insulin, EGF, and/or transferrin.

In some embodiments, the targeting ligand is in the form of an N-acetyl-galactosamine trimer. In some embodiments, the targeting ligand is in the form of an N-acetyl-galactosamine tetramer.

Oligomeric Compounds

The targeting ligands disclosed herein can be linked to an oligomeric compound. In some embodiments, the oligomeric compound is an expression-inhibiting oligomeric compound. In some embodiments, the expression-inhibiting oligomeric compound is an RNAi agent. In some embodiments, the expression-inhibiting oligomeric compound is a double-stranded RNAi agent. In some embodiments the expression-inhibiting oligomeric compound is a single-stranded oligonucleotide. The expression-inhibiting oligomeric compounds may be synthesized using methods commonly used in the art.

The expression-inhibiting oligomeric compounds may include one or more modified nucleotides. A nucleotide base (or nucleobase) is a heterocyclic pyrimidine or purine compound which is a constituent of all nucleic acids and includes adenine (A), guanine (G), cytosine (C), thymine (T), and uracil (U). As used herein, the term "nucleotide" may include a modified nucleotide or nucleotide mimic, abasic site, or a surrogate replacement moiety. As used herein, a "modified nucleotide" is a nucleotide, nucleotide mimic, abasic site, or a surrogate replacement moiety other than a ribonucleotide (2'-hydroxyl nucleotide). In some embodiments a modified nucleotide includes a 2'-modified nucleotide (i.e. a nucleotide with a group other than a hydroxyl group at the 2' position of the five-membered sugar ring). Modified nucleotides include, but are not limited to: 2'-modified nucleotides, 2'-O-methyl nucleotides (represented herein as a lower case letter 'n' in a nucleotide sequence), 2'-deoxy-2'-fluoro nucleotides (represented herein as Nf, also represented herein as 2'-fluoro nucleotide), 2'-deoxy nucleotides (represented herein as dN), 2'-methoxyethyl (2'-O-2-methoxylethyl) nucleotides, (represented herein as NM or 2'-MOE), 2'-amino nucleotides, 2'-alkyl nucleotides, 3' to 3' linkages (inverted) nucleotides (represented herein as invdN, invN, invn, invX), non-natural base including nucleotides, locked nucleotides, bridged nucleotides, peptide nucleic acids, 2',3'-seco nucleotide mimics (unlocked nucleobase analogues, represented herein as $N_{UNA \; or}$ NUNA), locked nucleotide (represented herein as $N_{LNA}$ or NLNA), 3'-O-methoxy (2' internucleotide linked) nucleotide (represented herein as 3'-OMen), 2'-F-arabino nucleotides (represented herein as NfANA or $Nf_{ANA}$), morpholino nucleotides, vinyl phosphonate deoxyribonucleotide (represented herein as vpdN), vinyl phosphonate nucleotides, and abasic nucleotides (represented herein as X or Ab). It is not necessary for all positions in a given compound to be uniformly modified. Conversely, more than one modification may be incorporated in a single expression-inhibiting oligomeric compound or even in a single nucleotide thereof. The expression-inhibiting oligomeric compounds may be synthesized and/or modified by methods known in the art. Modification at each nucleotide is independent of modification of the other nucleotides.

Modified nucleobases include synthetic and natural nucleobases, such as 5-substituted pyrimidines, 6-azapyrimidines, N-2-, N-6-, and O-6-substituted purines (e.g., 2-aminopropyladenine), 5-propynyluracil, 5-propynylcytosine, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine, 2-thiocytosine, 5-halouracil, 5-halocytosine, 5-propynyl uracil, 5-propynyl cytosine, 6-azo-uracil, 6-azo-cytosine, 6-azo-thymine, 5-uracil (pseudouracil), 4-thiouracil, 8-halo, 8-amino, 8-thiol, 8-thioalkyl, 8-hydroxyl and other 8-substituted adenines and guanines, 5-substituted uracils and cytosines (e.g., 5-halo uracils and cytosines (e.g., 5-bromouracil and 5-bromocytosine), 5-trifluoromethyl uracil, 5-trifluoromethyl cytosine), 7-methylguanine, 7-methyladenine, 8-azaguanine, 8-azaadenine, 7-deazaguanine, 7-deazaadenine, 3-deazaguanine, and 3-deazaadenine.

For the expression-inhibiting oligomeric compounds described herein, any modified nucleotides may be linked by phosphate-containing or non-phosphate-containing covalent internucleoside linkages. Modified internucleoside linkages or backbones include, but are not limited to, 5'-phosphorothioate group (represented herein as a lower case 's' before a nucleotide, as in sN, sn, sNf, or sdN), chiral phosphorothioates, thiophosphate, phosphorodithioates, phosphotriesters, aminoalkyl-phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, morpholino linkages, boranophosphates having normal 3'-5' linkages, 2'-5' linked analogs of boranophosphates, and boranophosphates having inverted polarity wherein the adjacent pairs of nucleoside units are linked 3'-5' to 5'-3' or 2'-5' to 5'-2'. In some embodiments, a modified internucleoside linkage or backbone lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified internucleoside backbones include, but are not limited to, siloxane backbones, sulfide backbones, sulfoxide backbones, sulfone backbones, formacetyl and thioformacetyl backbones, methylene formacetyl and thioformacetyl backbones, alkene-containing backbones, sulfamate backbones, methyleneimino and methylenehydrazino backbones, sulfonate and sulfonamide backbones, amide backbones, and other backbones having mixed N, O, S, and $CH_2$ components.

In some embodiments, an expression-inhibiting oligomeric compound is a double-stranded RNAi agent, and includes a sense strand and an antisense strand that are at least partially complementary (at least 70% complementary) to each other. The antisense strand contains a region having a sequence that is perfectly complementary (100% complementary) or at least substantially complementary (at least 85% complementary) to a sequence in a target mRNA. The length of a double-stranded RNAi agent sense strand and antisense strand each can be 16 to 30 nucleotides in length. The sense and antisense strands can be either the same length or they can be different lengths. In some embodiments, the sense strand is about 19 nucleotides in length while the antisense strand is about 21 nucleotides in length. In some embodiments, the sense strand is about 21 nucleotides in length while the antisense strand is about 23 nucleotides in length. In other embodiments, the sense and antisense strands are each independently 17-21 nucleotides in length. In some embodiments, both the sense and antisense strands are each 21-26 nucleotides in length. In some embodiments, both the sense and antisense strands are each 26 nucleotides in length. In some embodiments, the sense and antisense strands are each independently 17 to 26 nucleotides in length. In some embodiments, a double-stranded RNAi agent has a duplex length of about 16, 17, 18, 19, 20, 21, 22, 23 or 24 nucleotides. This region of perfect or substantial complementarity between the sense strand and the antisense strand is typically 15-25 (e.g., 15, 16, 17, 18, 19, 20, 21, 22, 23, 24, or 25 nucleotides in length) nucleotides in length and occurs at or near the 5' end of the antisense strand.

The expression-inhibiting oligomeric compounds that are conjugated to the ligands disclosed herein optionally and independently include an additional 1, 2, 3, 4, 5, or 6 nucleotides (as an extension) at the 3' end, the 5' end, or both the 3' and 5' ends of the core sequences. These additional nucleotides, if present, may or may not be complementary to the corresponding sequence in the targeted mRNA.

In some embodiments, when a double-stranded RNAi agent is conjugated to the targeting ligands disclosed herein, the additional sense strand additional nucleotides, if present, may or may not be identical to the corresponding sequence in the targeted mRNA. The additional antisense strand additional nucleotides, if present, may or may not be complementary to the corresponding additional nucleotides of the sense strand, if present.

Double-stranded RNAi agents can be formed by annealing an antisense strand with a sense strand.

In some embodiments, the targeting ligand is linked to an RNAi agent at the 3' or 5' end of either the sense strand or the antisense strand of the RNAi agent. In some embodiments, the targeting ligand is linked to 5' end of the sense strand. In some embodiments, the targeting ligand is linked to the 3' end of the sense strand. In some embodiments, the targeting ligand is linked to the RNAi agent via a labile, cleavable, or reversible bond. In some embodiments, the labile, cleavable, or reversible bond is included in a cleavable moiety added between the RNAi agent and the targeting ligand.

In some embodiments, the expression-inhibiting oligomeric compound is a single-stranded oligonucleotide. In some embodiments, the single-stranded oligonucleotide is utilizes the RNA interference mechanism to inhibit expression of the target mRNA. In some embodiments, the single-stranded oligonucleotides are active in reducing expression of the target nucleic acid through a mechanism other than RNA interference.

In some embodiments, the gene expression level and/or mRNA level of a target in a subject to whom a described targeting ligand conjugated to an expression-inhibiting oligomeric compound is administered is reduced by at least about 5%, for example, by at least about 10%, 15%, 20%, 25%, 30%, 35%, 40%, 45%, 50%, 55%, 60%, 65%, 70%, 75%, 80%, 85%, 90%, 95%, or 98% relative to the subject prior to administration or to a subject not receiving the targeting ligand conjugate. The gene expression level and/or mRNA level in the subject may be reduced in a cell, group of cells, and/or tissue of the subject. In some embodiments, the protein level in a subject to whom a described targeting ligand conjugated to an expression-inhibiting oligomeric compound has been administered is reduced by at least about 5%, for example, by at least about 10%, 15%, 20%, 25%, 30%, 35%, 40%, 45%, 50%, 55%, 60%, 65%, 70%, 75%, 80%, 85%, 90%, 95%, or 98% relative to the subject prior to being administered the targeting ligand conjugate or to a subject not receiving the targeting ligand conjugate. The protein level in the subject may be reduced in a cell, group of cells, tissue, blood, and/or other fluid of the subject. A reduction in gene expression, mRNA, or protein levels can be assessed by any methods known in the art. Reduction or decrease in mRNA level and/or protein level are collectively referred to herein as inhibiting, decreasing, or reducing the expression of the targeted gene.

Specific expression-inhibiting oligomeric compounds that can be used with the targeting ligands disclosed are known in the art. In particular, numerous references disclose expression-inhibiting oligomeric compounds that may be conjugated to the targeting ligands disclosed herein for delivery of the composition to the liver. Non-limiting examples include U.S. patent application Ser. No. 15/281,309, entitled Compositions and Methods for Inhibiting Gene Expression of LPA, which is incorporated herein by reference in its entirety, discloses various double-stranded expression-inhibiting oligomeric compounds targeting the human apolipoprotein(a) gene [LPA] (to inhibit expression of the apo(a) protein which is part of the lipoprotein(a) particle, and thereby the lipoprotein(a) particle (Lp(a))), that are suitable for use with the targeting ligands disclosed herein. The apo(a) gene [LPA] is expressed predominantly in the liver in humans and non-human primates. Similarly, for example, U.S. patent application Ser. No. 15/229,314, entitled RNAi Therapy for Hepatitis B Virus Infection, which is also incorporated herein by reference in its entirety, discloses various double-stranded expression-inhibiting oligomeric compounds targeting the hepatitis B virus, that are suitable for use with the targeting ligands disclosed herein. The Hepatitis B Virus is a strict hepatotrophic, double-stranded DNA containing virus and is classified as one member of the Hepadnaviruses, belonging to the family of Hepadnaviridae. Further, as another example, U.S. patent application Ser. No. 15/229,314, entitled Compositions and Methods for Inhibiting Gene Expression of Factor XII, which is incorporated herein by reference in its entirety, discloses various double-stranded expression-inhibiting oligomeric compounds targeting the Factor XII (or Factor 12, F12) gene, that are suitable for use with the targeting ligands disclosed herein. Factor XII is a serine protease expressed predominantly in the liver and found in blood. Additionally, as another example U.S. patent application Ser. No. 14/740,307, entitled Compositions and Methods for Inhibiting Gene Expression of Alpha-1 AntiTrypsin, which is incorporated herein by reference in its entirety, discloses various double-stranded expression-inhibiting oligomeric compounds targeting the alpha-1 antitrypsin (or AAT) gene, that are suitable for use with the targeting ligands disclosed herein. AAT is a protease inhibitor belonging to the serpin superfamily, and normal AAT protein is primarily synthesized in the liver by hepatocytes and secreted into blood. Further, WO 2016/01123, entitled Organic Compositions to Treat APOC3-Related Diseases, which is incorporated herein by reference in its entirety, discloses various double-stranded expression-inhibiting oligomeric compounds targeting human apolipoprotein III (APOC3), that are suitable for use with the targeting ligands disclosed herein. Apolipoprotein C-III is a constituent of lipoproteins that is believed to inhibit hepatic uptake of triglyceride-rich particles. Additional references disclosing various therapeutic compounds, including expression-inhibiting oligomeric compounds, that may be suitable for use with the targeting ligands disclosed herein, can also be found in the art. These include, but are not limited to, compositions where targeting to the liver would be desirable.

Pharmaceutical Compositions and Formulations

The targeting ligands disclosed herein, when linked to an oligomeric compound, can be used to treat a subject (e.g., a human or mammal) having a disease or disorder that would benefit from administration of the compound. In some embodiments, the targeting ligands disclosed herein, when linked to an expression-inhibiting oligomeric compound, can be used to treat a subject (e.g., a human) having a disease or disorder that would benefit from reduction or inhibition in expression of the target mRNA. The subject is administered a therapeutically effective amount of any one or more expression-inhibiting oligomeric compounds, such as an RNAi agent, that is linked to a targeting ligand disclosed herein. The subject can be a human, patient, or human patient. The subject may be an adult, adolescent, child, or infant. The described pharmaceutical compositions including a targeting ligand linked to an expression-inhibiting oligomeric compound can be used to provide methods for the therapeutic treatment of diseases. Such methods include administration of a pharmaceutical composition described herein to a human being or animal.

The pharmaceutical compositions and methods disclosed herein may decrease the level of the target mRNA in a cell, group of cells, group of cells, tissue, or subject, including: administering to the subject a therapeutically effective amount of a herein described expression-inhibiting oligomeric compound that is linked to a targeting ligand, thereby inhibiting the expression of a target mRNA in the subject. In some embodiments, the subject has been previously identified as having a pathogenic upregulation of the target gene in the targeted cell or tissue.

In some embodiments, pharmaceutical compositions include at least one expression-inhibiting oligomeric compound linked to a targeting ligand. These pharmaceutical compositions are particularly useful in the inhibition of the expression of the target mRNA in a target cell, a group of cells, a tissue, or an organism. The pharmaceutical compositions can be used to treat a subject having a disease or disorder that would benefit from reduction in the level of the target mRNA, or inhibition in expression of the target gene. The pharmaceutical compositions can be used to treat a subject at risk of developing a disease or disorder that would benefit from reduction of the level of the target mRNA or an inhibition in expression the target gene. In one embodiment, the method includes administering a composition including a targeting ligand as described herein linked to an expression-inhibiting oligomeric compound, such as an RNAi agent, to a subject to be treated. In some embodiments, one or more pharmaceutically acceptable excipients (including vehicles, carriers, diluents, and/or delivery polymers) are added to the pharmaceutical compositions including a targeting ligand linked to an expression-inhibiting oligomeric compound, thereby forming a pharmaceutical formulation suitable for in vivo delivery to a human.

In some embodiments, the described pharmaceutical compositions including a targeting ligand linked to an expression-inhibiting oligomeric compound are used for treating or managing clinical presentations associated with expression of a target mRNA. In some embodiments, a therapeutically or prophylactically effective amount of one or more of pharmaceutical compositions is administered to a subject in need of such treatment, prevention or management. In some embodiments, administration of any of the conjugated ligands covalently linked to an oligomeric compound can be used to decrease the number, severity, and/or frequency of symptoms of a disease in a subject.

The described pharmaceutical compositions including a targeting ligand linked to an expression-inhibiting oligomeric compound, can be used to treat at least one symptom in a subject having a disease or disorder that would benefit from reduction or inhibition in expression of a target mRNA. In some embodiments, the subject is administered a therapeutically effective amount of one or more pharmaceutical compositions including an expression-inhibiting oligomeric compound, such as an RNAi agent, linked to a targeting ligand described herein, thereby treating the symptom. In other embodiments, the subject is administered a prophylactically effective amount of one or more of expression-inhibiting oligomeric compounds thereby preventing the at least one symptom.

In some embodiments, the expression or level of a target mRNA in a subject to whom an expression-inhibiting oligomeric compound linked to a targeting ligand disclosed herein is administered is reduced by at least about 5%, for example, but at least about 10%, 15%, 20%, 25%, 30%, 35%, 40%, 45%, 50%, 55%, 60%, 65%, 70%, 75%, 80%, 85%, 90%, 95%, or 98% relative to the subject not receiving the pharmaceutical composition. The gene expression level in the subject may be reduced in a cell, group of cells, and/or tissue of the subject. In some embodiments, the level of mRNA is reduced. In other embodiments, the expressed protein level is reduced. In some embodiments, the level of protein in a subject to whom an expression-inhibiting oligomeric compound linked to a targeting ligand disclosed herein is administered is reduced by at least about 5%, for example, but at least about 10%, 15%, 20%, 25%, 30%, 35%, 40%, 45%, 50%, 55%, 60%, 65%, 70%, 75%, 80%, 85%, 90%, 95%, or 98% relative to the subject not receiving the pharmaceutical composition. Reduction in expression, mRNA levels, or protein levels can be assessed by any methods known in the art. Reduction or decrease in mRNA level and/or protein level are collectively referred to herein as a reduction or decrease in target RNA or inhibiting or reducing the expression of target mRNA.

The route of administration is the path by which an expression-inhibiting oligomeric compound is brought into contact with the body. In general, methods of administering drugs and nucleic acids for treatment of a mammal are well known in the art and can be applied to administration of the compositions described herein. The expression-inhibiting oligomeric compound linked to the herein described targeting ligands can be administered via any suitable route in a preparation appropriately tailored to the particular route. Thus, herein described pharmaceutical compositions can be administered by injection, for example, intravenously, intramuscularly, intracutaneously, subcutaneously, intraarticularly, or intraperitoneally. In some embodiments, there herein described pharmaceutical compositions and be administered via inhalation.

The pharmaceutical compositions including an expression-inhibiting oligomeric compound linked to a targeting ligand described herein can be delivered to a cell, group of cells, tumor, tissue, or subject using oligonucleotide delivery technologies known in the art. In general, any suitable method recognized in the art for delivering a nucleic acid molecule (in vitro or in vivo) can be adapted for use with a herein described compositions. For example, delivery can be by local administration, (e.g., direct injection, implantation, or topical administering), systemic administration, or subcutaneous, intravenous, intraperitoneal, or parenteral routes, including intracranial (e.g., intraventricular, intraparenchymal and intrathecal), intramuscular, transdermal, airway (aerosol), nasal, oral, rectal, or topical (including buccal and sublingual) administration. In certain embodiments, the compositions are administered by subcutaneous or intravenous infusion or injection.

Accordingly, in some embodiments, the herein described pharmaceutical compositions may comprise one or more pharmaceutically acceptable excipients. In some embodiments, the pharmaceutical compositions described herein can be formulated for administration to a subject.

As used herein, a pharmaceutical composition or medicament includes a pharmacologically effective amount of at least one of the described therapeutic compounds and one or more pharmaceutically acceptable excipients. Pharmaceutically acceptable excipients (excipients) are substances other than the Active Pharmaceutical ingredient (API, therapeutic product, e.g., F12 RNAi agent) that are intentionally included in the drug delivery system. Excipients do not exert or are not intended to exert a therapeutic effect at the intended dosage. Excipients may act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops. Formulations for topical administration to the skin surface can be prepared by dispersing the drug with a dermatologically acceptable carrier such as a lotion, cream, ointment or soap. Useful are carriers capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations. In the case of self-propelling solution and spray formulations, the effect can be achieved either by choice of a valve having the desired spray characteristics (i.e., being capable of producing a spray having the desired particle size) or by incorporating the active ingredient as a suspended powder in controlled particle size. For administration by inhalation, the compounds also can be delivered in the form of an aerosol spray from pressured container or dispenser which contains a suitable propellant, e.g., a gas such as carbon dioxide, or a nebulizer.

Systemic administration also can be by transmucosal or transdermal means. For transmucosal or transdermal administration, penetrants appropriate to the barrier to be permeated are used in the formulation. Such penetrants generally are known in the art, and include, for example, for transmucosal administration, detergents and bile salts. Transmucosal administration can be accomplished through the use of nasal sprays or suppositories. For transdermal administration, the active compounds typically are formulated into ointments, salves, gels, or creams as generally known in the art.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the therapeutic effect to be achieved, and the limitations inherent in the art of compounding such an active compound for the treatment of individuals. Furthermore, administration can be by periodic injections of a bolus, or can be made more continuous by intravenous, intramuscular or intraperitoneal administration from an external reservoir (e.g., an intravenous bag).

In conjunction with the methods of the present disclosure, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a drug as well as tailoring the dosage and/or therapeutic regimen of treatment with the drug.

A pharmaceutical composition can contain other additional components commonly found in pharmaceutical compositions. Such additional components include, but are not limited to: anti-pruritics, astringents, local anesthetics, or anti-inflammatory agents (e.g., antihistamine, diphenhydramine, etc.). It is also envisioned that cells, tissues or isolated organs that express or comprise the herein defined RNAi agents may be used as "pharmaceutical compositions." As used herein, "pharmacologically effective amount," "therapeutically effective amount," or simply "effective amount" refers to that amount of an RNAi agent to produce a pharmacological, therapeutic or preventive result.

Generally, an effective amount of an active compound will be in the range of from about 0.1 to about 100 mg/kg of body weight/day, e.g., from about 1.0 to about 50 mg/kg of body weight/day. In some embodiments, an effective amount of an active compound will be in the range of from about 0.25 to about 5 mg/kg of body weight per dose. In some embodiments, an effective amount of an active ingredient will be in the range of from about 0.5 to about 3 mg/kg of body weight per dose. The amount administered will also likely depend on such variables as the overall health status of the patient, the relative biological efficacy of the compound delivered, the formulation of the drug, the presence and types of excipients in the formulation, and the route of administration. Also, it is to be understood that the initial dosage administered can be increased beyond the above upper level in order to rapidly achieve the desired blood-level or tissue level, or the initial dosage can be smaller than the optimum.

For treatment of disease or for formation of a medicament or composition for treatment of a disease, the pharmaceutical compositions described herein including an expression-inhibiting oligomeric compound, such as an RNAi agent, linked to a targeting ligand, can be combined with an excipient or with a second therapeutic agent or treatment including, but not limited to: a second or other expression-inhibiting oligomeric compound, a small molecule drug, an antibody, an antibody fragment, and/or a vaccine.

The described targeting ligands, when linked to expression-inhibiting oligomeric compounds, and when added to pharmaceutically acceptable excipients or adjuvants, can be packaged into kits, containers, packs, or dispensers. The pharmaceutical compositions described herein may be packaged in pre-filled syringes or vials.

The above provided embodiments are now illustrated with the following, non-limiting examples.

EXAMPLES

The following examples are not limiting and are intended to illustrate certain embodiments disclosed herein.

Some of the abbreviations used in the following experimental details of the synthesis of the examples are defined below: h or hr=hour(s); min=minute(s); mol=mole(s); mmol=millimole(s); M=molar; μM=micromolar; g=gram(s); μg=microgram(s); rt or RT=room temperature; L=liter(s); mL=milliliter(s); wt=weight; Et$_2$O=diethyl ether; THF=tetrahydrofuran; DMSO=dimethyl sulfoxide; EtOAc=ethyl acetate; Et$_3$N or TEa=triethylamine; i-Pr$_2$NEt or DIPEA or DIEA=diisopropylethylamine; CH$_2$Cl$_2$ or DCM=methylene chloride; CHCl$_3$=chloroform; CDCl$_3$=deuterated chloroform; CCl$_4$=carbon tetrachloride; MeOH=methanol; EtOH=ethanol; DMF=dimethylformamide; BOC=t-butoxycarbonyl; CBZ=benzyloxycarbonyl; TBS=t-butyldimethylsilyl; TBSCl=t-butyldimethylsilyl chloride; TFA=trifluoroacetic acid; DMAP=4-dimethylaminopyridine; NaN$_3$=sodium azide; Na$_2$SO$_4$=sodium sulfate; NaHCO$_3$=sodium bicarbonate; NaOH=sodium hydroxide; MgSO$_4$=magnesium sulfate; K$_2$CO$_3$=potassium carbonate; KOH=potassium hydroxide; NH$_4$OH=ammonium hydroxide; NH$_4$Cl=ammonium chloride; SiO$_2$=silica; Pd—C=palladium on carbon; HCl=hydrogen chloride or hydrochloric acid; NMM=N-methylmorpholine; H$_2$=hydrogen gas; KF=potassium fluoride; EDC-HCl=N-(3-Dimethylaminopropyl)-N'-ethylcarbodiimide hydrochloride; MTBE=methyl-tert-butyl ether; MeOH=methanol; Ar=argon; SiO$_2$=silica; R$_T$=retention time.

Additionally, exemplary expression-inhibiting oligomeric compounds suitable for use with the targeting ligands disclosed herein are set forth in various Tables in the Examples that follow. The following notations are used to indicate modified nucleotides for sequences set forth in the Tables disclosed herein:

N=2'-OH (unmodified) ribonucleotide (capital letter without f or d indication)
n=2'-OMe modified nucleotide
Nf=2'-fluoro modified nucleotide
dN=2'-deoxy nucleotides
N$_{UNA}$=2',3'-seco nucleotide mimics (unlocked nucleobase analogs)
N$_{LNA}$=locked nucleotide
Nf$_{ANA}$=2'-F-Arabino nucleotide
NM=2'-methoxyethyl nucleotide
X or Ab=abasic ribose
R=ribitol
(invdN)=inverted deoxyribonucleotide (3'-3' linked nucleotide)
(invAb)=inverted abasic nucleotide
(invX)=inverted abasic nucleotide
(invn)=inverted 2'-OMe nucleotide
s=phosphorothioate linked nucleotide
vpdN=vinyl phosphonate deoxyribonucleotide
(3'OMen)=3'-OMe nucleotide
(5Me-Nf)=5'-Me, 2'-fluoro nucleotide
cPrp=cyclopropyl phosphonate The compounds of the present disclosure can be made using synthetic chemical techniques known to those of skill in the art.

Example 1. Synthesis of Targeting Ligand Phosphoramidite Compound Structure 101b 1) Preparation of Tri-tert-butyl N—[N-(Benzyloxycarbonyl)-L-γ-glutamyl]-L-glutamate (3)

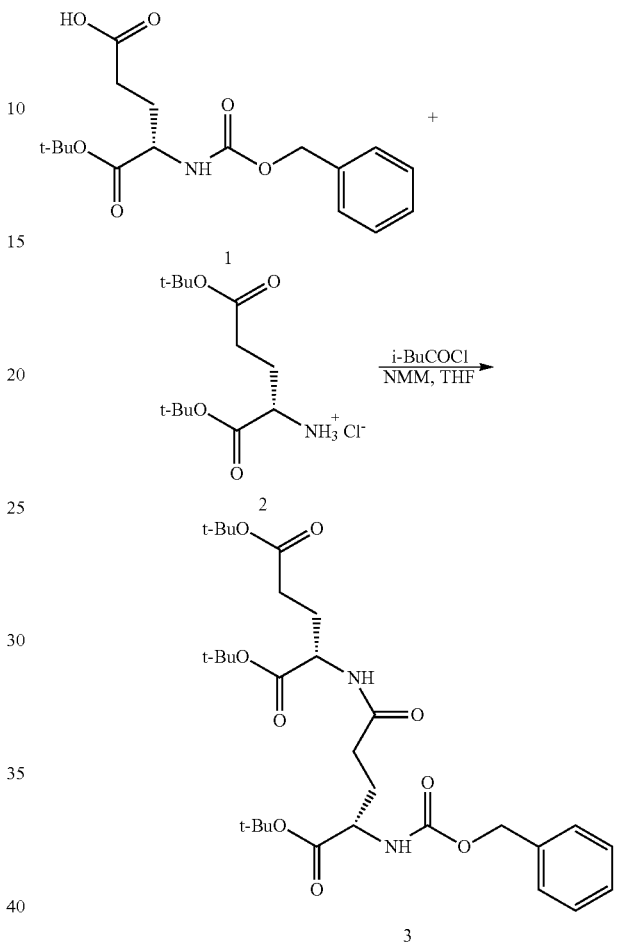

To a nitrogen-flushed, 250-mL 3-neck round-bottomed flask equipped with a thermocouple, magnetic stir bar, nitrogen inlet, and powder funnel was added 1 (10.00 g, 29.64 mmol) followed by THF (100 mL). The resulting solution was stirred, and N-methylmorpholine (7.82 mL, 71.15 mmol) was added.

The powder funnel was replaced with a rubber septum, and the mixture was cooled using an ice bath to 0° C. Isobutyl chloroformate (iBuCOCl, 3.85 mL, 29.64 mmol, 1.0 equivalents) was added to the reaction mixture dropwise over 10 minutes, maintaining a pot temperature of less than 4.0° C. Following addition, the mixture was stirred 40 minutes more, and the septum was replaced with a powder funnel. To the reaction mixture was added 2 (8.767 g, 29.64 mmol, 1.0 equivilants) portion-wise over 15 minutes, maintaining a pot temperature of less than 4.0° C. Following addition of 2, the ice bath and powder funnel were removed, and the reaction was allowed to warm to ambient temperature over the course of the remaining steps. The clear, colorless solution was aged 25 minutes following the addition of 2.

A sample of the reaction (98 μL diluted into 5.0 mL ACN in a 5-mL volumetric flask) was taken 40 minutes after the start of addition of 2 and analyzed for percent conversion by RP-HPLC. There was found to be 23% remaining of 1, so after 60 minutes of reaction, additional iBuCOCl (1.16 mL, 30 mol %) and 2 (2.63 g, 30 mol %) were added sequentially. The solution was aged for an additional 60 minutes, until a sample showed greater than 99% conversion by HPLC. Total reaction time was 2.5 hours from the start of the initial addition of 2.

The reaction solution was poured into a stirring solution of 0.5 M HCl$_{(aq)}$ chilled in an ice bath to 3° C. and stirred about 5 minutes. The quenched reaction mixture was transferred to a 500-mL reparatory funnel, and ethyl acetate (100 mL) was added. The layers were separated, and the organic phase was washed with brine (100 mL), dried over MgSO$_4$, filtered into a 500-mL round-bottomed flask, and concentrated in vacuo, affording a thick colorless oil. The oil was dissolved in MTBE (100 mL) and concentrated in vacuo, once again yielding a thick colorless oil.

To the stirring oil was added hexanes (100 mL). White haze appeared in the solution, which then disappeared upon further stirring. Seed crystals were added, and the mixture was allowed to stir for 40 minutes, during which time white crystals slowly formed.

Figure 1:
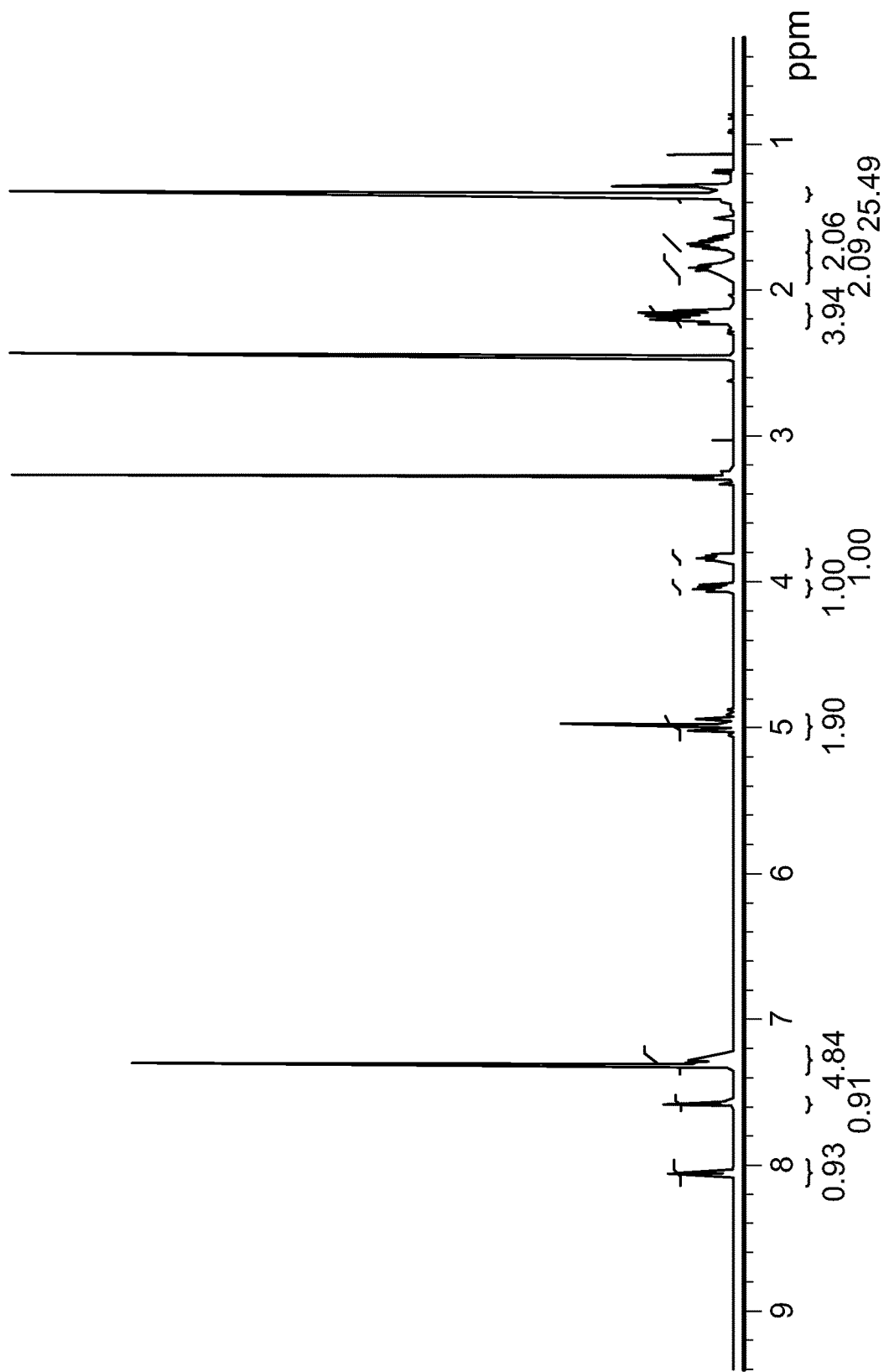
FIG. 1 is a $^1$H NMR spectra of compound 3 (which is described below in Example 1).

Within 20 minutes, the slurry was thick enough to impede stirring, and additional hexanes (50 mL) was added. After 40 minutes, the slurry was filtered over a coarse fritted funnel, washed three times with hexanes (~10 mL each), and air-dried in the funnel for 1 hour, affording 3 as a fine white powder (15.64 g, 91%). $^1$H NMR of compound 3 is shown at FIG. 1. On 75 gram scale the yield was 917% with purity 99%.

2) Preparation of N—[N-(Benzyloxycarbonyl)-L-γ-glutamyl]-L-glutamic acid (4)

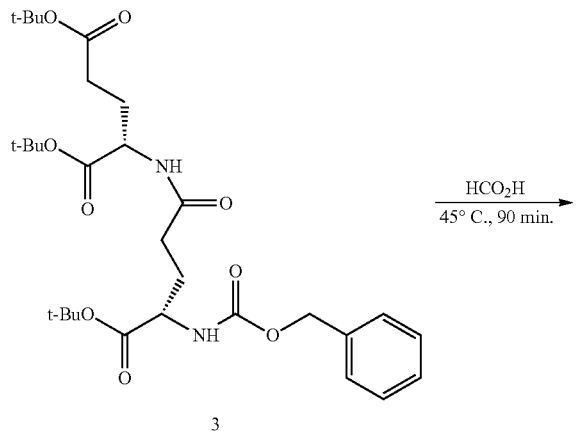

3

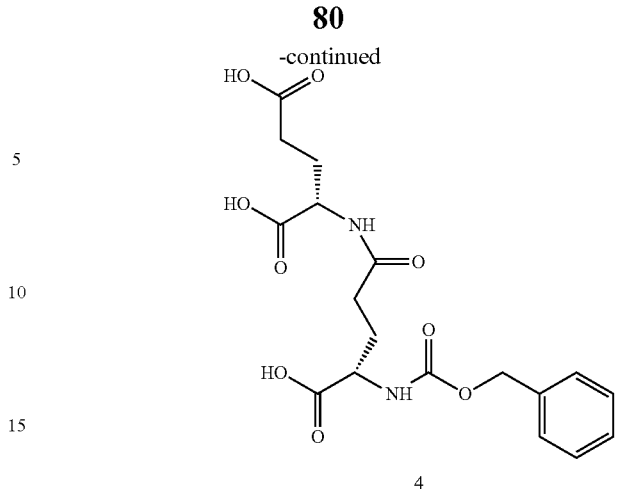

4

To a 3000-mL, 3-necked round-bottomed flask equipped with an overhead stirrer, powder funnel, thermocouple, and heating mantle was added 3 (72.57 g, 125.4 mmol) and formic acid (reagent grade, >95%, 1.45 L, 20 vol. equiv.). The powder funnel was replaced by a stopper/N$_2$, and the resulting solution was heated to 45° C. and stirred for 1 hour, with monitoring by RP-HPLC. The reaction was deemed complete when less than 2.0 area % of mono-t-butyl esters remained.

A sample of the reaction (50 μL diluted into 950 μL of H$_2$O) was taken 60 minutes after the addition of formic acid, and the sample was analyzed by RP-HPLC for the percent of mono-t-butyl esters remaining. The analysis showed that 1.8% mono-t-Bu esters remained; therefore, at 90 minutes, the heat was removed.

Figure 2:
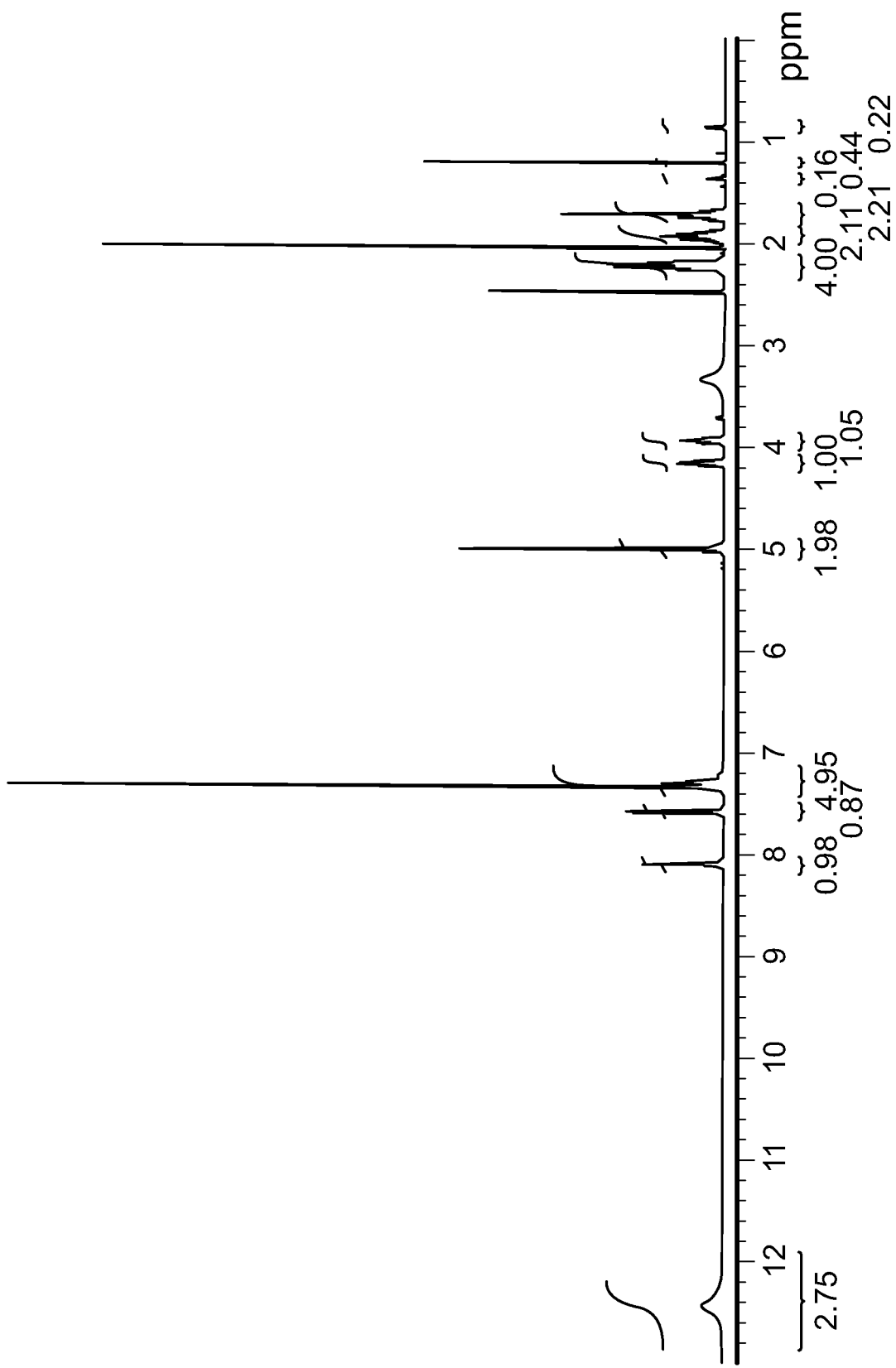
FIG. 2 is a $^1$H NMR spectra of compound 4 (which is described below in Example 1).

The reaction was diluted with toluene and acetonitrile (ACN, 1500 mL each), and the mixture was concentrated in vacuo. Formic acid was azeotropically removed with 1:1 ACN:toluene (~600 mL), and twice with ACN (~500 mL each). The material was dried on high vacuum overnight to afford a white foamy solid compound 4 (54.3 g, quantitative yield). $^1$H NMR of compound 4 (L/N 1321-063B) is shown at FIG. 2.

3) Preparation of N—[N-(Benzyloxycarbonyl)-L-γ-glutamyl]-L-glutamic acid, tri-[NAG-PEG$_2$]-amide (6)

4

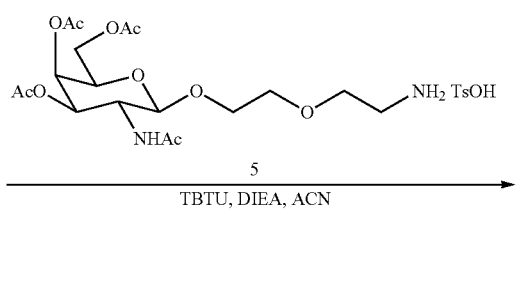

5
―――――――――――→
TBTU, DIEA, ACN

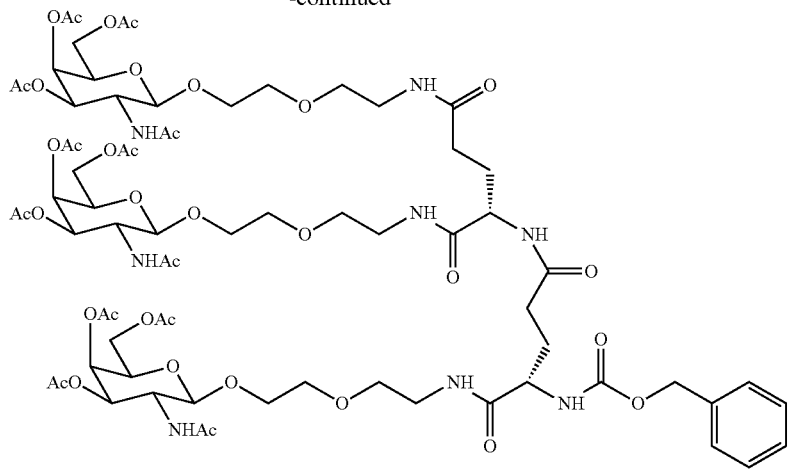

6

To a 1-liter round-bottomed flask was added NAG-amine p-tosylate salt (5, 59.19 g, 97.6 mmol, 4.13 equiv.) and Z-bis-Glu triacid (4, 10.01 g, 23.6 mmol, 1.0 equiv.). The mixture was dissolved in acetonitrile (500 mL) and concentrated in vacuo to remove water azeotropically. The residue was dissolved in fresh acetonitrile (400 mL) and transferred to a nitrogen-flushed 1-liter 3-neck round-bottomed flask containing a stir bar and equipped with a thermocouple. Water content was measured by KF (257 ppm).

To the stirring solution under nitrogen was added TBTU (28.20 g, 87.8 mmol, 3.7 equiv.) via a powder funnel. Residual TBTU on the funnel was rinsed into the reaction using additional acetonitrile (100 mL). DIPEA (34.0 mL, 25.2 g, 8.0 equiv.) was added dropwise via syringe over 20 minutes, maintaining a reaction temperature below 25° C. The mixture was stirred for 2 hours from the start of DIPEA addition, with monitoring by HPLC. Analysis at 78 minutes showed complete consumption of starting material.

After two hours, the solvent was removed in vacuo. The resulting thick oil was dissolved in dichloromethane (1000 mL) and washed with 1.0 N $HCl_{(aq)}$ (3×500 mL) and saturated $NaHCO_{3(aq)}$ (3×500 mL). The organic layer was dried over $Na_2SO_4$, filtered, and concentrated in vacuo to afford an off-white waxy solid (33.5 g).

Figure 3:
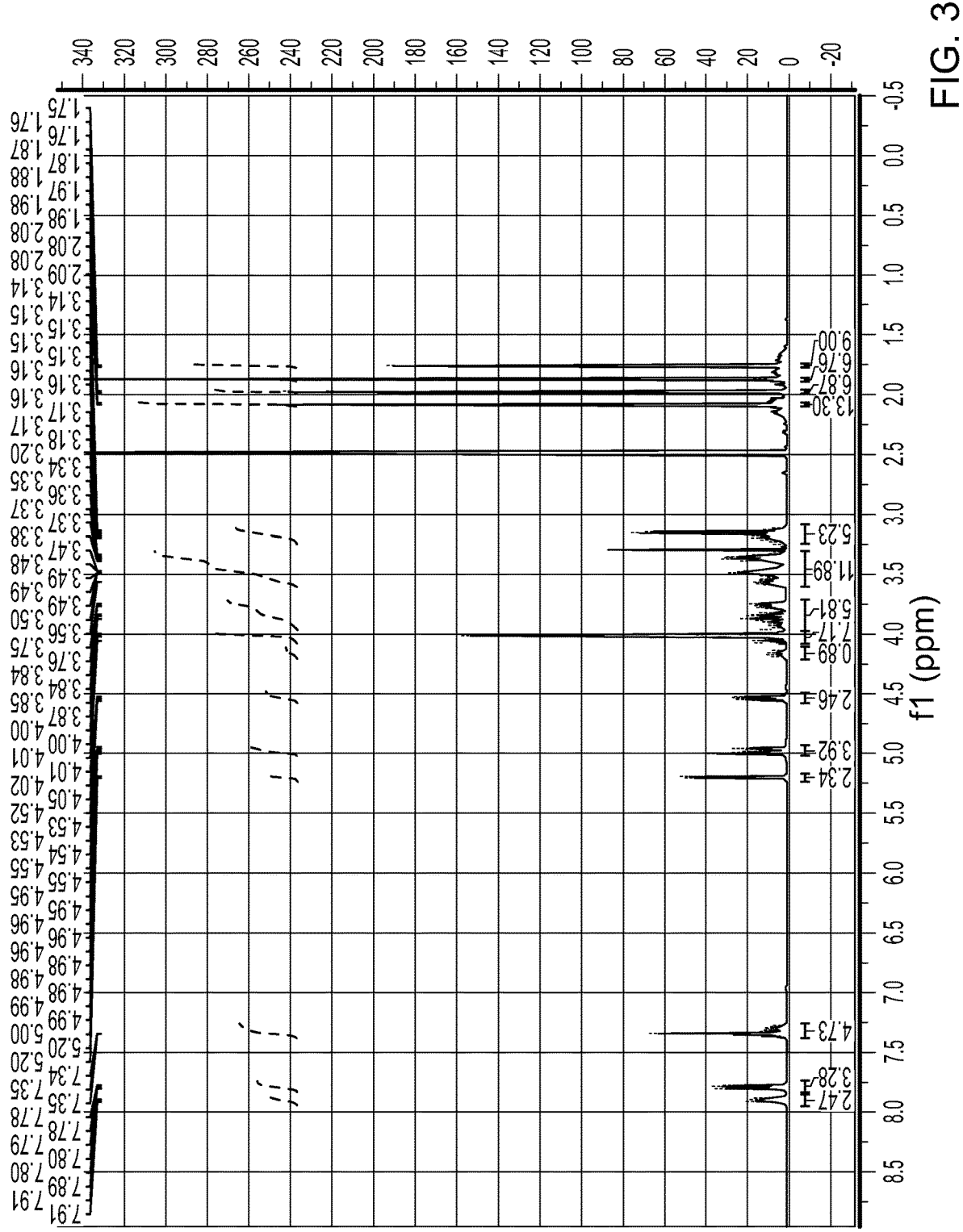
FIG. 3 is a $^1$H NMR spectra of compound 6 (which is described below in Example 1)

Flash column chromatography was performed on an ISCO CombiFlash automated purification system using chloroform and methanol as eluents. All fractions suspected to contain product based on the UV chromatogram (220 nm) were analyzed by HPLC, and all fractions containing at least 97.0% AUC of product were pooled and concentrated to afford 18.75 g (97.0% purity) of 6. Impure fractions were pooled to yield an additional 12.2 g (78.8% purity) of 6. Total yield of 6 was 70.9%. $^1$H NMR of compound 6 is shown at FIG. 3.

4) Preparation of Tri-NAG-bis-Glu-NH$_2$ tosylate salt (7)

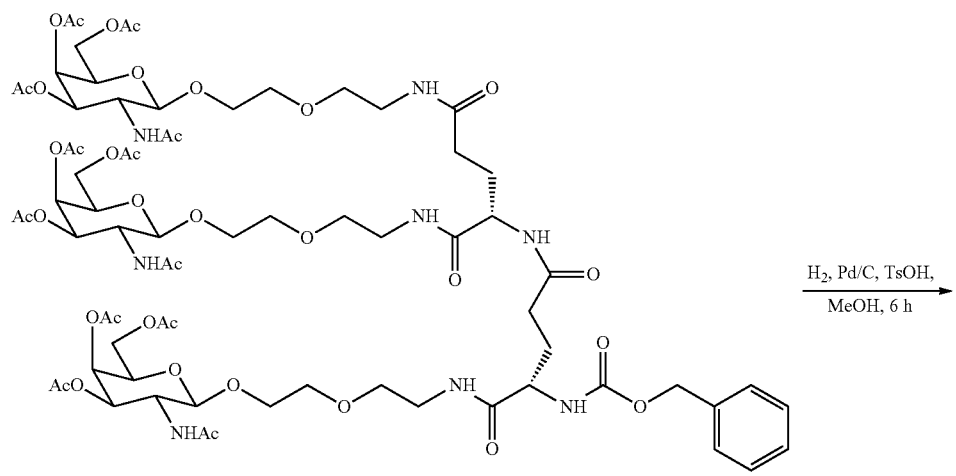

6

$H_2$, Pd/C, TsOH, MeOH, 6 h

-continued

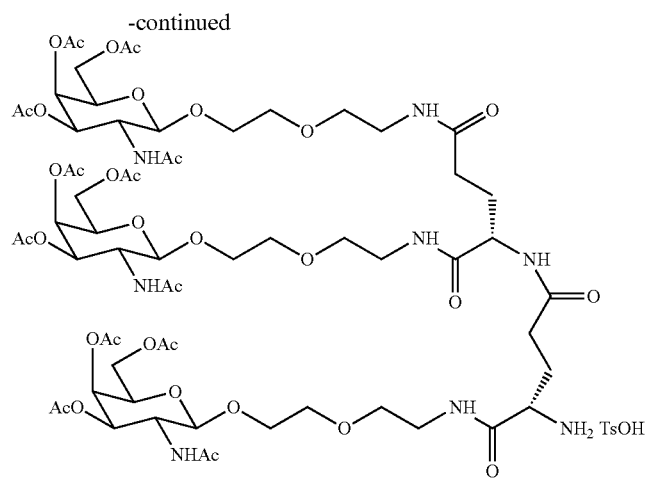

7

Compound 6 (5.737 g, 3.46 mmol) in MeOH (155 mL) with p-TsOH—H$_2$O (0.657 g, 3.46 mmol) was hydrogenated in presence of Pd/C 10% (688 mg) for 6 h. TLC (CHCl$_3$; MeOH=8.5:1.5) confirmed that the reaction was completed by that time. The reaction flask was filled with Ar, EtOH was added (200 mL) and the solution was filtered through celite cake. The product was concentrated and dried in vacuo.

Figure 4:
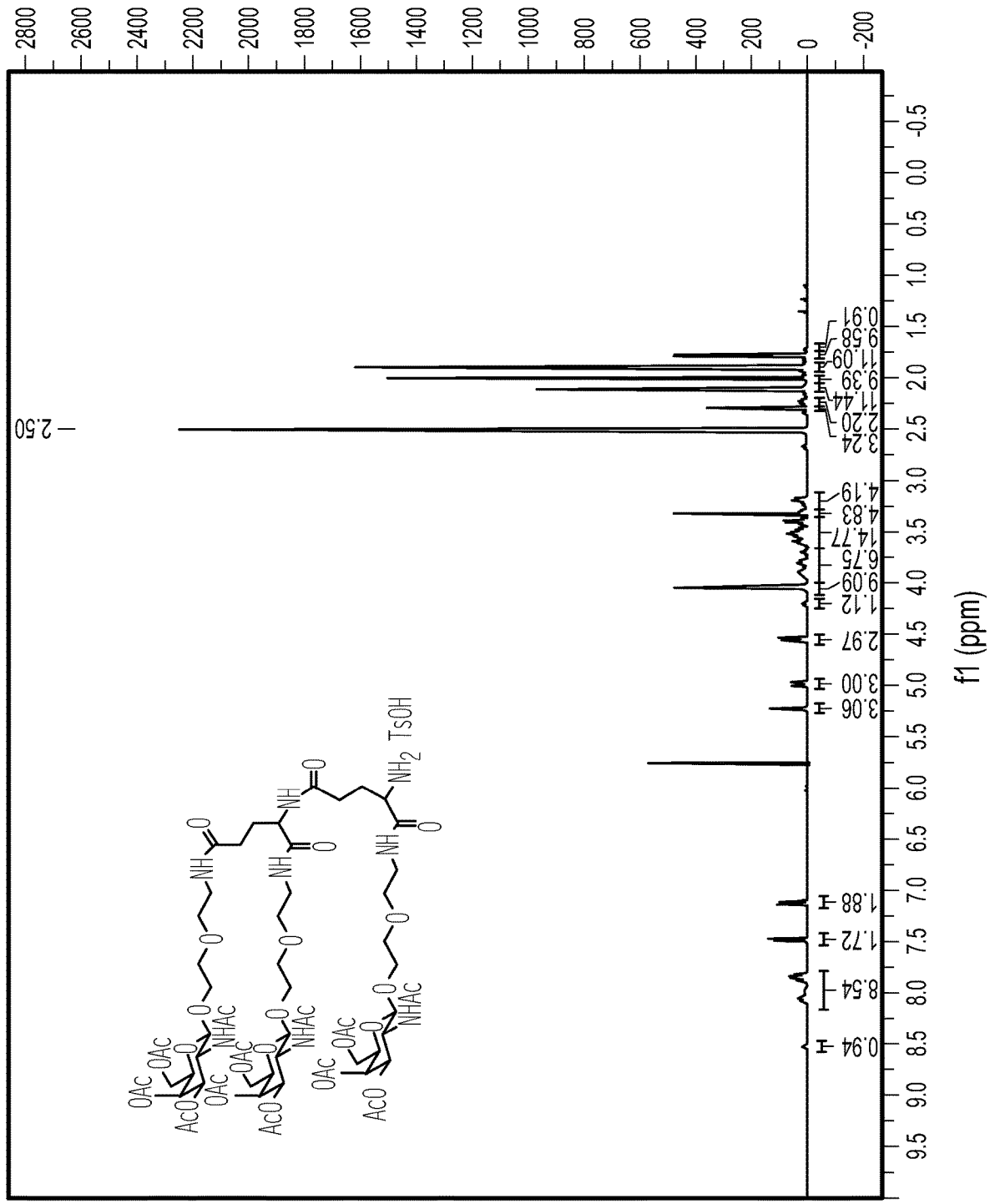
FIG. 4 is a $^1$H NMR spectra of compound 7 (which is described below in Example 1)

Yield 4.81 g product tosylate salt 7. $^1$H NMR of compound 7 is shown at FIG. 4.

5) Preparation of Tri-NAG-bis-Glu-NH-PEG$_6$-OH (9)

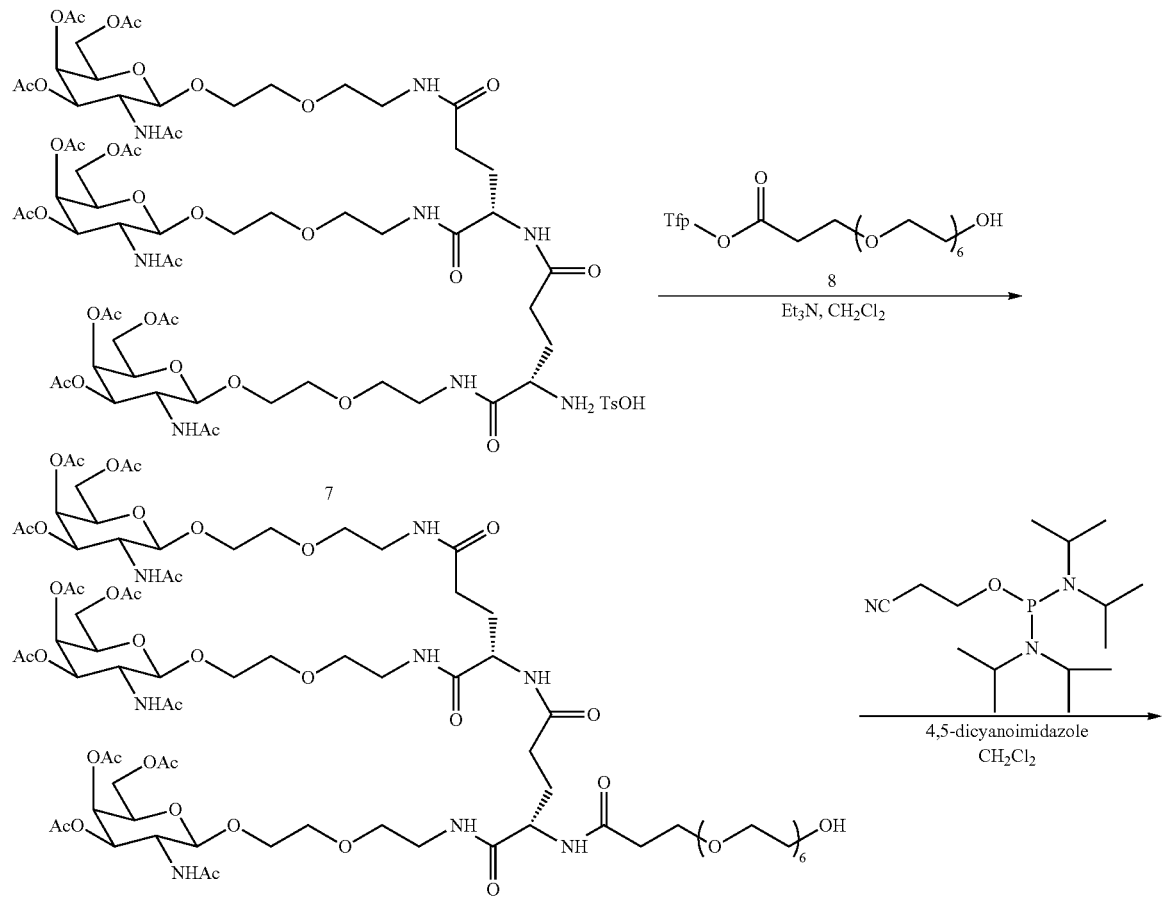

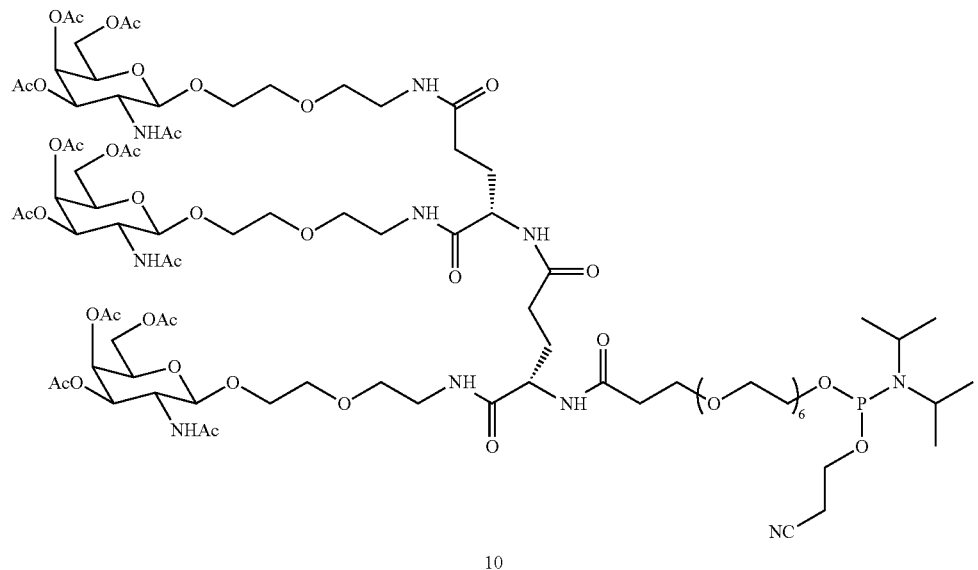

10

Figure 5:
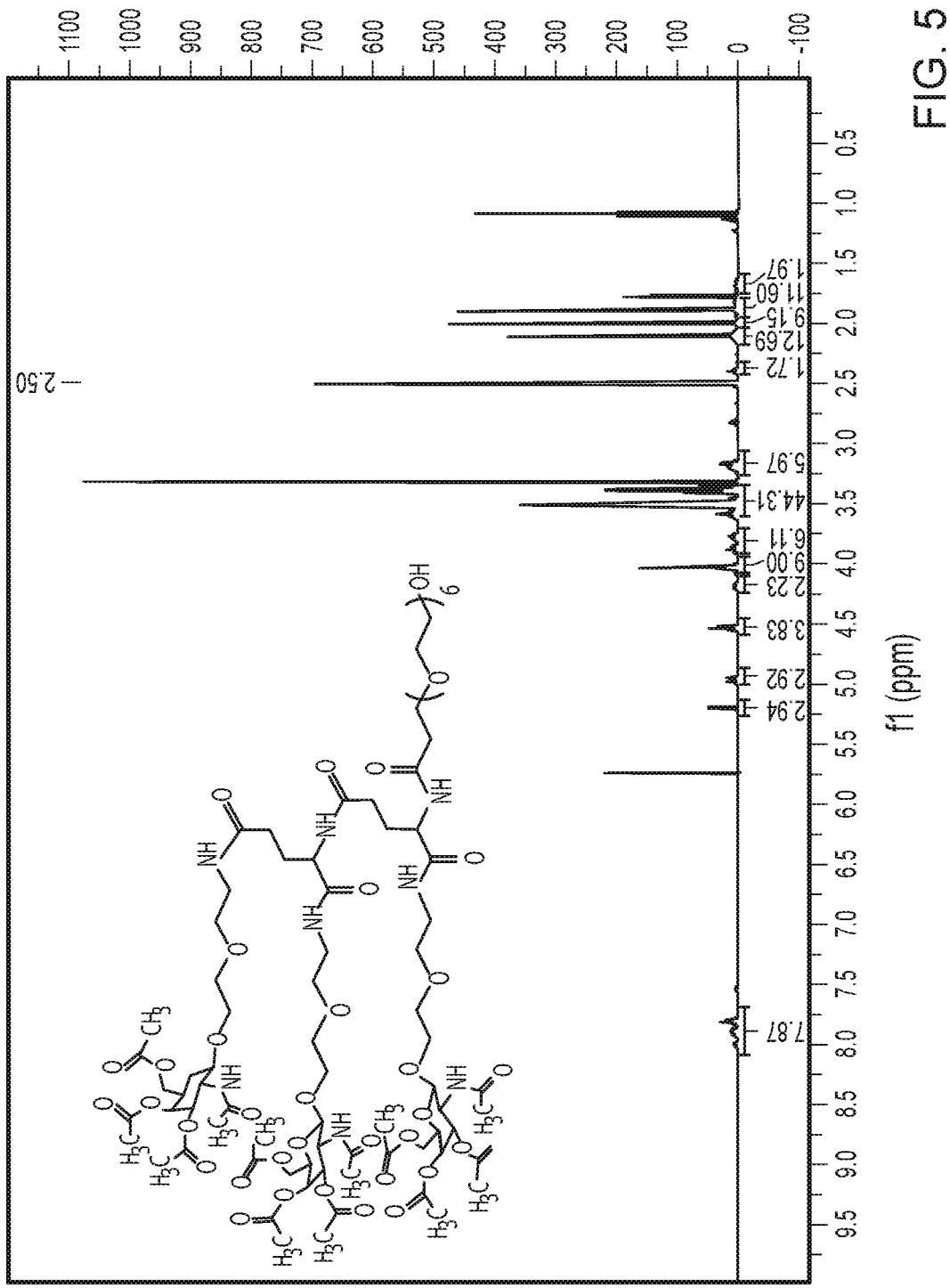
FIG. 5 is a $^1$H NMR spectra of compound 9 (which is described below in Example 1).

Procedure A (if tri-NAG amine salt 7 is less than 96% pure): NAG amine salt 7 (~90% pure, 18.50 g, 10.90 mmol) and HO-PEG$_6$-CO$_2$TFP ester 8 (6.57 g, 13.08 mmol) were dissolved in dichloromethane (185 mL) and cooled to 0° C. To this solution was added triethylamine (6.10 mL, 43.59 mmol). The solution was allowed to warm to room temperature and stirred for 18 hours with monitoring by HPLC. The reaction was quenched with saturated aqueous NaHCO$_3$ and brine (1:1, 140 mL), stirred for 30 min at RT, and the layers were separated. The organic layer was washed with saturated aqueous NaHCO$_3$ (3×140 mL) and brine (1:1) and dried with Na$_2$SO$_4$. The drying agent was filtered and the solution was concentrated and purified via flash chromatography, which gave 9 (13.56 g, 67%) as a white solid material. $^1$H NMR of compound 9 is shown at FIG. 5.

Flash column chromatography was performed on an ISCO CombiFlash automated purification system using dichloromethane and methanol as eluents. Pure fractions were pooled and concentrated to afford 13.56 g of 9 (99% purity). Impure fractions were pooled to yield 4.9 g of 9 (~95% purity).

Procedure B (if tri-NAG amine salt 7 is greater than 96% pure): Product 7 (1.94 g, 1.272 mmol) in DCM (40 mL) was stirred under Ar with HO-PEG$_6$-CO$_2$TFP ester 8 (767 mg, 1.526 mmol) and DIPEA (443 µL, 2.544 mmol) for 16 h. The reaction mixture was concentrated in vacuo, dissolved in CHCl$_3$ and added dropwise to stirring Et$_2$O (90 mL). The precipitate was separated, rinsed with Et$_2$O (3×35 mL) and dried in vacuo. Yield 2.275 g (96%).

6) Preparation of Tri-NAG-bis-Glu-NH-PEG$_6$ phosphoramidite (10)

Compound 9 (6.62 g, 3.56 mmol) and 4,5-dicyanoimidazole (0.11 g, 0.89 mmol) were dissolved in anhydrous dichloromethane (230 mL) and placed under nitrogen atmosphere. To this mixture, a solution of 2-cyanoethyl-N,N,N',N'-tetraisopropylphosphorodiamidite ("Phos reagent", 1.46 mL, 4.62 mmol) in anhydrous dichloromethane (5 mL) was added dropwise over 5 minutes. The reaction mixture was stirred at room temperature for 3 h with monitoring HPLC (<1% SM remaining).

Figure 6:
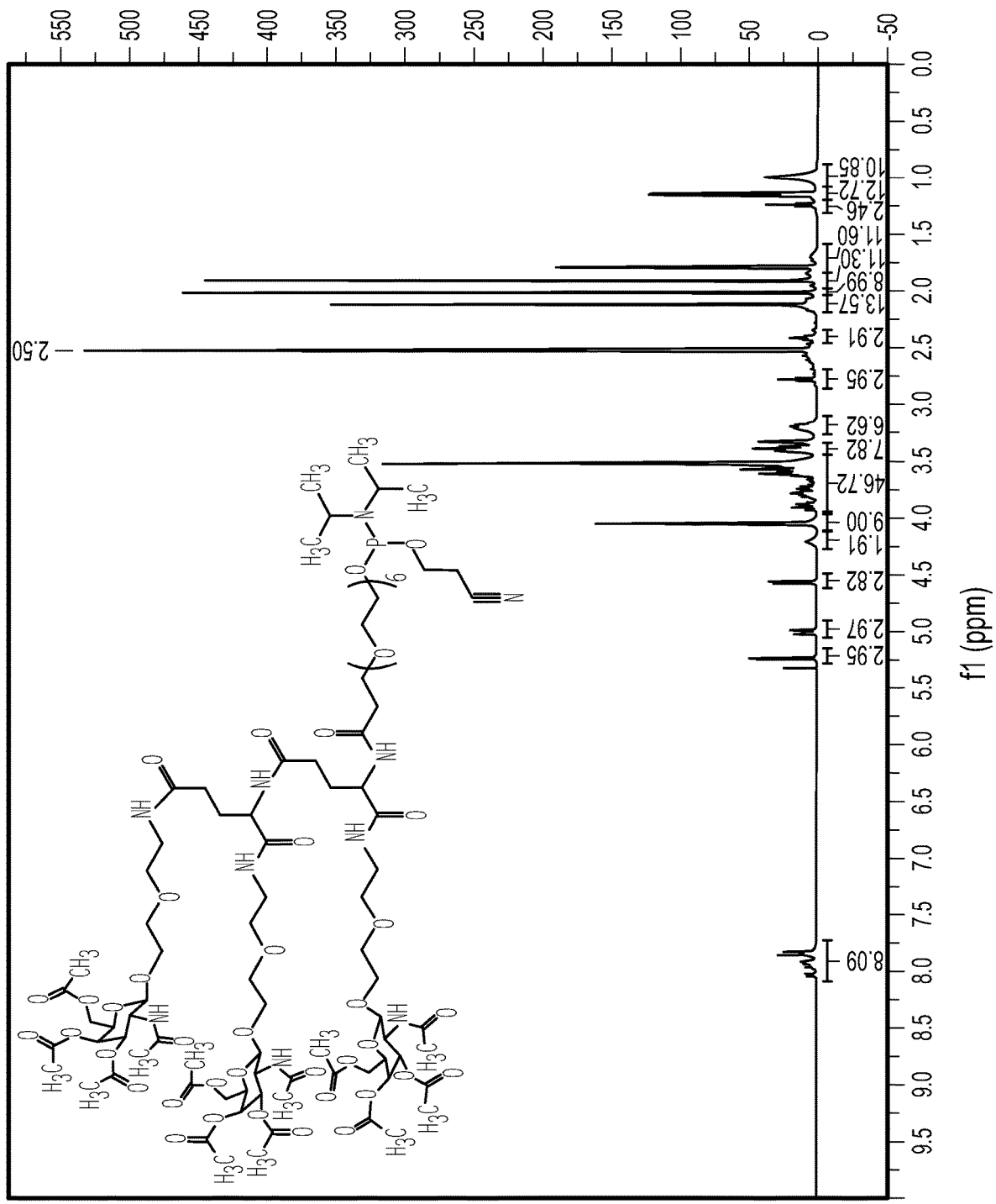
FIG. 6 is a $^1$H NMR spectra of compound 10 (which is Structure 101d herein, and is described below in Example 1).

The reaction mixture was washed with saturated aqueous NaHCO$_3$ (2×150 mL), 3% DMF in H$_2$O (v/v, 2×150 mL), H$_2$O (3×150 mL), and brine (1×150 mL), and the organic layer was dried with Na$_2$SO$_4$. The drying agent was filtered, and the solution was concentrated in vacuo to give crude product. Crude product was suspended in 5% toluene-hexane (50 mL) and stirred for 5 minutes, after which the solvent was decanted. The process was repeated with 5% toluene-hexane (1×50 mL) and hexane (2×50 mL). The solids were dried over vacuum resulting 6.69 g 10 as a white solid material (91%) (compound 10). $^1$H NMR of compound 10 (Structure 101d herein) is shown at FIG. 6.

Example 2. Synthesis of Targeting Ligand Phosphoramidite Compound Structure 103d
1) Preparation of Tri-NAG-bis-Glu-NH-PEG$_4$-OH (12)
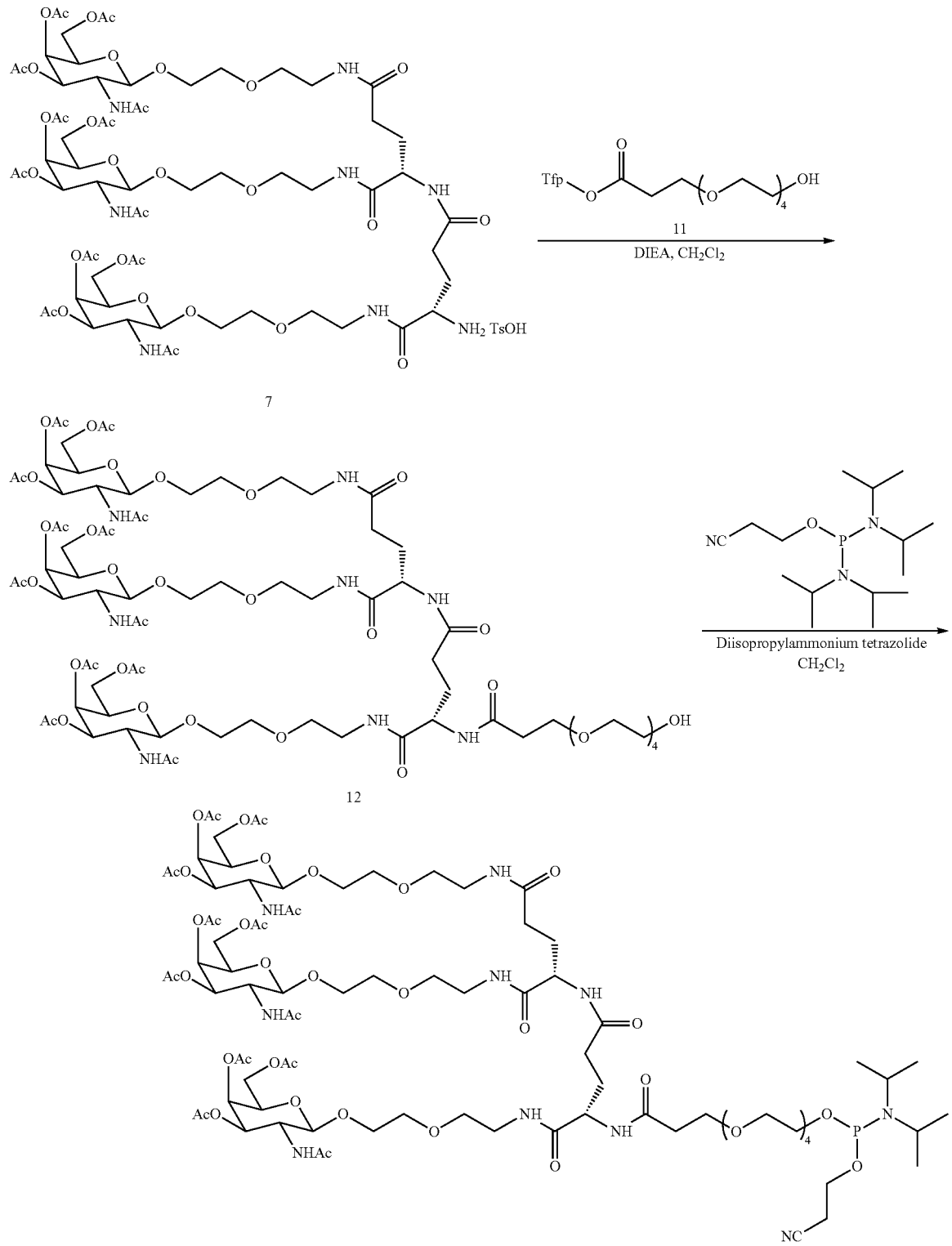

Product 7 (2.44 g, 1.44 mmol), from Example 1 above, was dissolved in DCM (30 mL) and placed under argon atmosphere. To the solution was added HO-PEG$_4$-CO$_2$TFP ester 11 (717 mg, 1.73 mmol) and DIPEA (502 μL, 2.88 mmol). The resulting mixture was stirred for 16 h. The reaction mixture was concentrated in vacuo and redissolved in CHCl$_3$. The solution was then added dropwise to stirring Et$_2$O (90 mL). The precipitate was separated, rinsed with Et$_2$O and dried in vacuo to yield 2.60 g (102%) of product 12 that was used without further purification.

2) Preparation of Tri-NAG-bis-Glu-NH-PEG$_4$ phosphoramidite (13)

Figure 7:
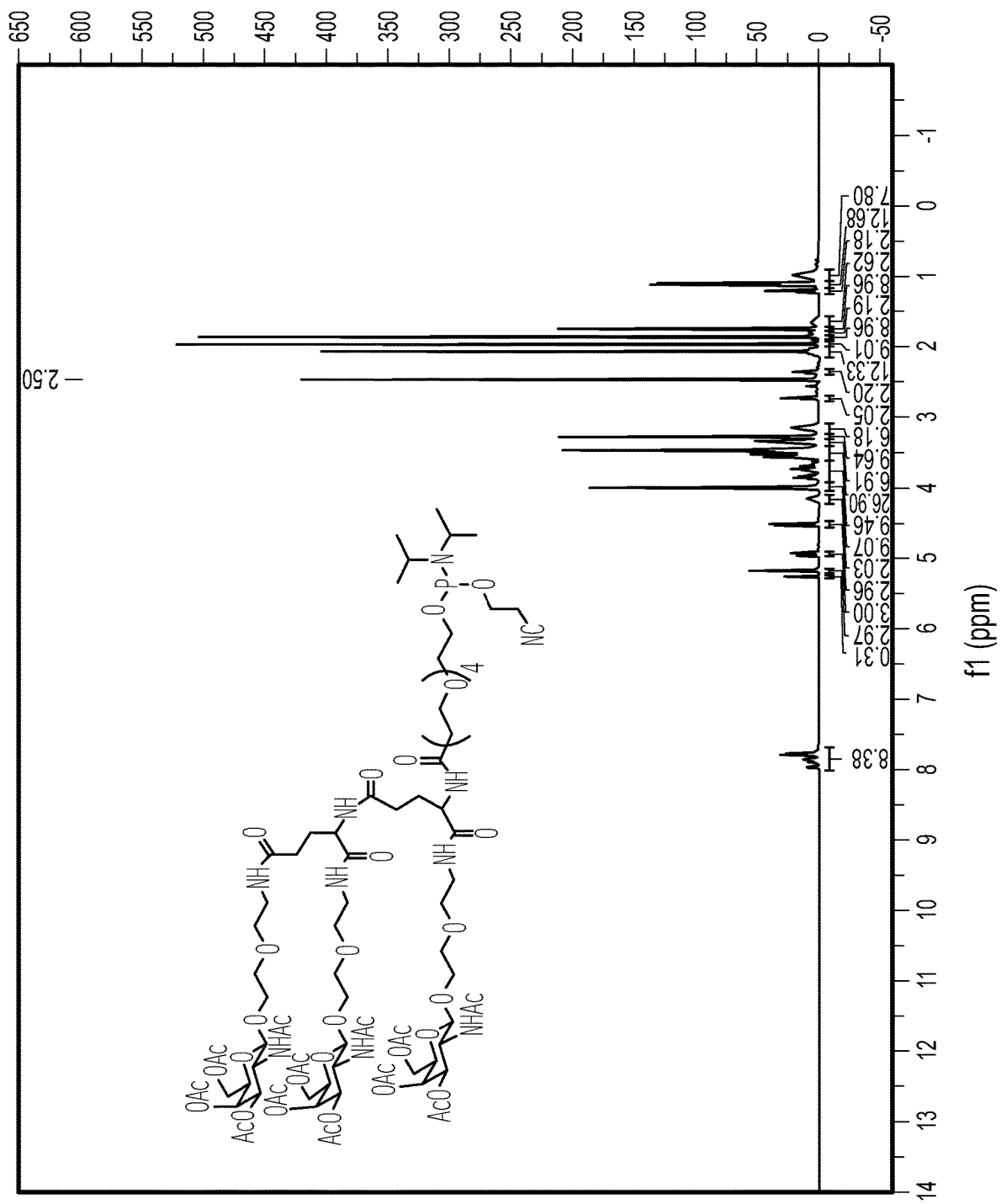
FIG. 7 is a $^1$H NMR spectra of compound 13 (which is Structure 103d herein, and is described below in Example 2).

Product 12 (1.80 g, 1.01 mmol) was coevaporated with pyridine twice before being dissolved in anhydrous dichloromethane (25 mL) and placed under argon atmosphere. To the solution was added diisopropylammonium tetrazolide (87 mg, 0.51 mmol) and 2-cyanoethyl-N,N,N',N'-tetraisopropylphosphorodiamidite (458 mg, 1.52 mmol). The reaction mixture was stirred at room temperature for 5 h with monitoring by TLC (CHCl$_3$:MeOH:Et$_3$N 95:5:2). Once all starting material had been consumed, the reaction mixture was diluted with DCM (250 mL) and washed with saturated aqueous NaHCO$_3$ (100 mL) and saturated aqueous brine (100 mL). The organic layer was dried with sodium sulfate, filtered, and concentrated. The crude was purified by column chromatography (DCM:MeOH:Et$_3$N 97:3:2) to yield 1.04 g (53%) of compound 13. $^1$H NMR of compound 13 (Structure 103d herein) is shown at FIG. 7.

Example 3. Synthesis of Targeting Ligand Phosphoramidite Compound Structure 102d 1) Preparation of Tri-NAG-bis-Glu-NH-PEG$_8$-OH (15)

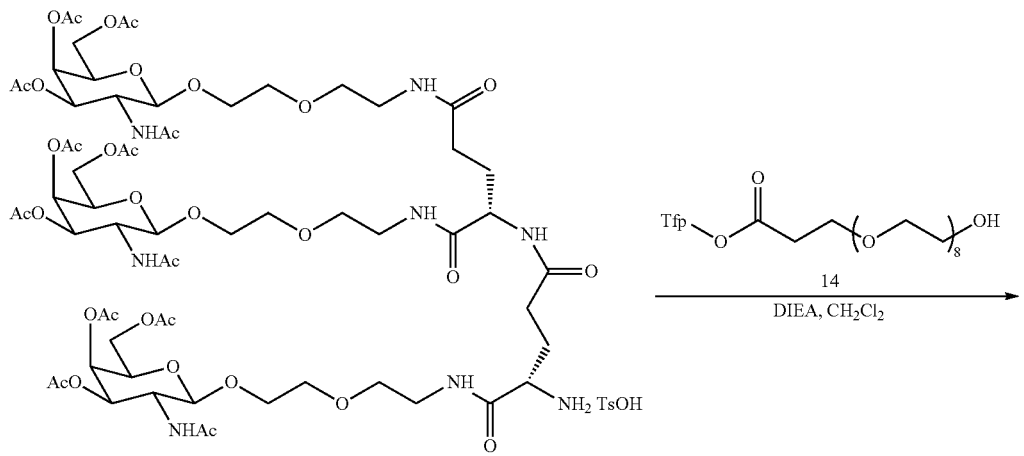

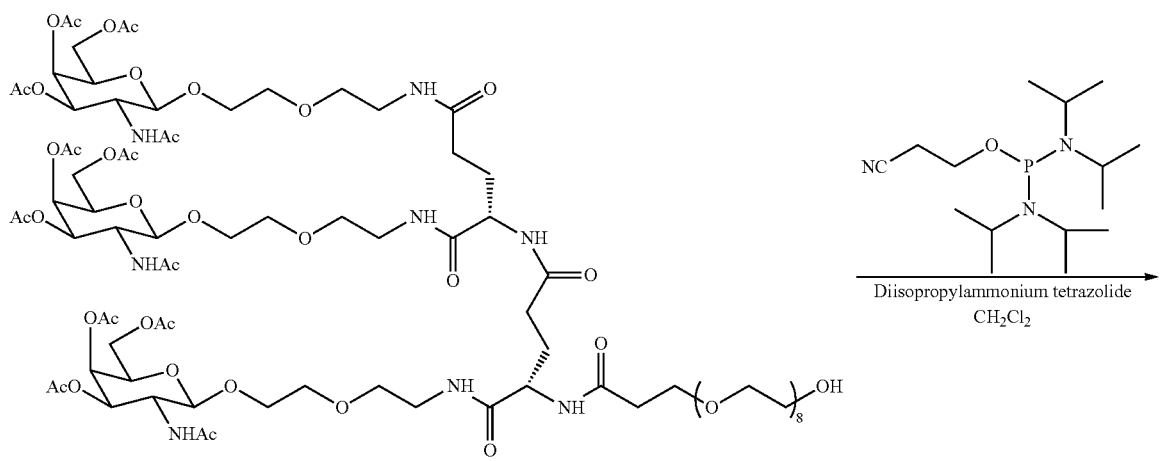

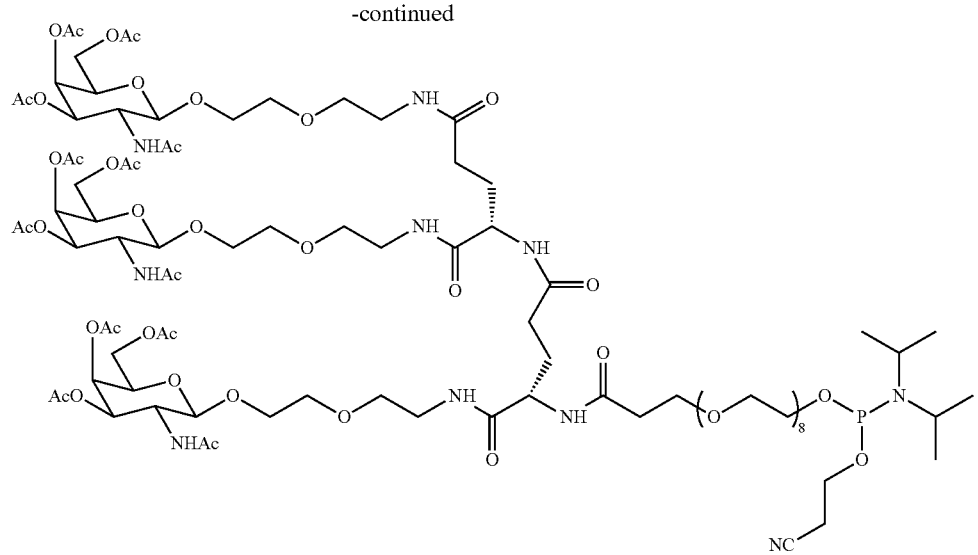

16

Product 7 (3.09 g, 1.82 mmol), from Example 1 above, was dissolved in DCM (30 mL) and placed under argon atmosphere. To the solution was added HO-PEG$_8$-CO$_2$TFP ester 14 (1.29 g, 2.18 mmol) and DIPEA (634 μL, 3.64 mmol). The resulting mixture was stirred for 16 h. The reaction mixture was concentrated in vacuo and redissolved CHCl$_3$. The solution was then added dropwise to stirring Et$_2$O (180 mL). The precipitate was separated, rinsed with Et$_2$O and dried in vacuo to yield 3.54 g (99%) of product 15 that was used without further purification.

2) Preparation of Tri-NAG-bis-Glu-NH-PEG$_8$ Phosphoramidite (16)

Figure 8:
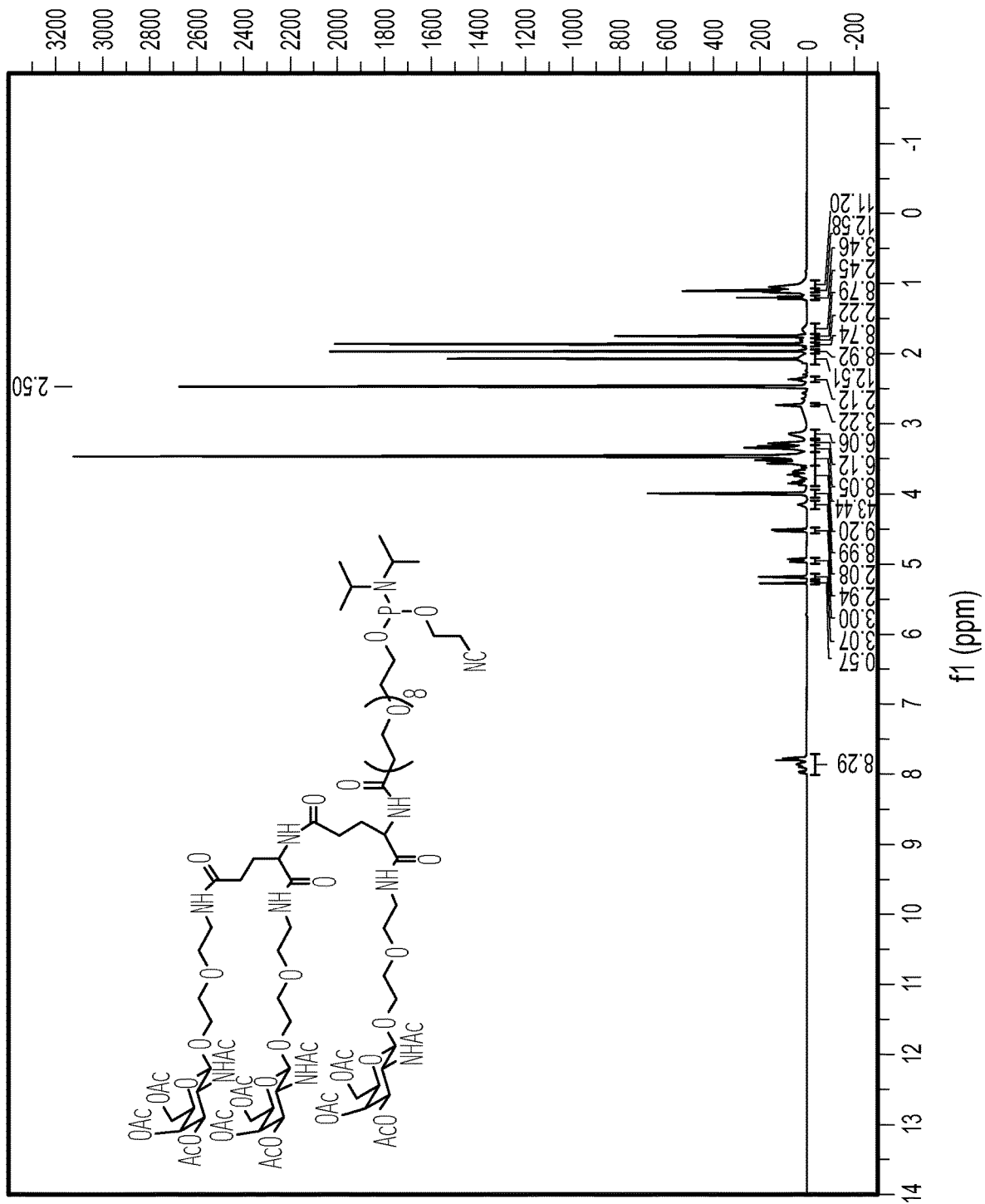
FIG. 8 is a $^1$H NMR spectra of compound 16 (which is Structure 102d herein, and is described below in Example 3).

Product 15 (1.79 g, 0.92 mmol) was coevaporated with pyridine twice before being dissolved in anhydrous dichloromethane (25 mL) and placed under argon atmosphere. To the solution was added diisopropylammonium tetrazolide (79 mg, 0.46 mmol) and 2-cyanoethyl-N,N,N',N'-tetraisopropylphosphorodiamidite (416 mg, 1.38 mmol). The reaction mixture was stirred at room temperature for 3 h with monitoring by TLC (CHCl$_3$:MeOH:Et$_3$N 95:5:2). Once all starting material had been consumed, the reaction mixture was concentrated in vacuo and redissolved in DCM. The solution was then added dropwise to stirring Et$_2$O (90 mL). The precipitate was separated, rinsed with Et$_2$O, and dried. The crude was purified by column chromatography (CHCl$_3$:MeOH:Et$_3$N 97:3:2) to yield 950 mg (48%) of compound 16. $^1$H NMR of compound 16 (Structure 102d herein) is shown at FIG. 8.

Example 4. Oligonucleotide Composition Synthesis

A. Synthesis. RNAi agents was synthesized according to phosphoramidite technology on solid phase used in oligonucleotide synthesis. Depending on the scale, either a MerMade96E® (Bioautomation) or a MerMade12® (Bioautomation) was used. Syntheses were performed on a solid support made of controlled pore glass (CPG, 500 Å or 600 Å, obtained from Prime Synthesis, Aston, PA, USA). All RNA and 2'-modified RNA phosphoramidites were purchased from Thermo Fisher Scientific (Milwaukee, WI, USA). Specifically, the following 2'-O-methyl phosphoramidites were used: (5'-O-dimethoxytrityl-N$^6$-(benzoyl)-2'-O-methyl-adenosine-3'-O-(2-cyanoethyl-N,N-diisopropylamino) phosphoramidite, 5'-O-dimethoxy-trityl-N$^4$-(acetyl)-2'-O-methyl-cytidine-3'-O-(2-cyanoethyl-N,N-diisopropyl-amino) phosphoramidite, (5'-O-dimethoxytrityl-N$^2$-(isobutyryl)-2'-O-methyl-guanosine-3'-O-(2-cyano-ethyl-N,N-diisopropylamino)phosphoramidite, and 5'-O-dimethoxy-trityl-2'-O-methyl-uridine-3'-O-(2-cyanoethyl-N,N-diisopropylamino)phosphoramidite. The 2'-deoxy-2'-fluoro-phosphoramidites carried the same protecting groups as the 2'-O-methyl RNA amidites. Targeting ligand containing phosphoramidites were dissolved in anhydrous dichloromethane or anhydrous acetonitrile (50 mM), while all other amidites were dissolved in anhydrous acetonitrile (50 mM) and molecular sieves (3 Å) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 10 min (RNA), 15 min (targeting ligand), 90 sec (2'OMe), and 60 sec (2'F). In order to introduce phosphorothioate linkages, a 100 mM solution of 3-phenyl 1,2,4-dithiazoline-5-one (POS, obtained from PolyOrg, Inc., Leominster, MA, USA) in anhydrous Acetonitrile was employed.

B. Cleavage and deprotection of support bound oligomer. After finalization of the solid phase synthesis, the dried solid support was treated with a 1:1 volume solution of 40 wt. % methylamine in water and 28% ammonium hydroxide solution (Aldrich) for two hours at 30° C. The solution was evaporated and the solid residue was reconstituted in water (see below).

C. Purification. Crude oligomers were purified by anionic exchange HPLC using a TKSgel SuperQ-5PW 13u column and Shimadzu LC-8 system. Buffer A was 20 mM Tris, 5 mM EDTA, pH 9.0 and contained 20% Acetonitrile and buffer B was the same as buffer A with the addition of 1.5 M sodium chloride. UV traces at 260 nm were recorded. Appropriate fractions were pooled then run on size exclusion HPLC using a GE Healthcare XK 16/40 column packed with Sephadex G-25 medium with a running buffer of 100 mM ammonium bicarbonate, pH 6.7 and 20% Acetonitrile.

D. Annealing. Complementary strands were mixed by combining equimolar RNA solutions (sense and antisense) in 0.2×PBS (Phosphate-Buffered Saline, 1×, Corning, Cellgro) to form the RNAi agents. This solution was placed into a thermomixer at 70° C., heated to 95° C., held at 95° C. for 5 min, and cooled to room temperature slowly. Some RNAi agents were lyophilized and stored at −15 to −25° C. Duplex concentration was determined by measuring the solution absorbance on a UV-Vis spectrometer in 0.2×PBS. The solution absorbance at 260 nm was then multiplied by a conversion factor and the dilution factor to determine the duplex concentration. Unless otherwise stated, all conversion factor was 0.037 mg/(mL·cm). For some experiments, a conversion factor was calculated from an experimentally determined extinction coefficient.

Example 5. Properties of Phosphoramidite-Containing Compounds that Include Targeting Ligands with Varying Lengths of PEG Linkers The following targeting ligand phosphoramidite compounds were synthesized according to the methods disclosed above in Examples 1-4:

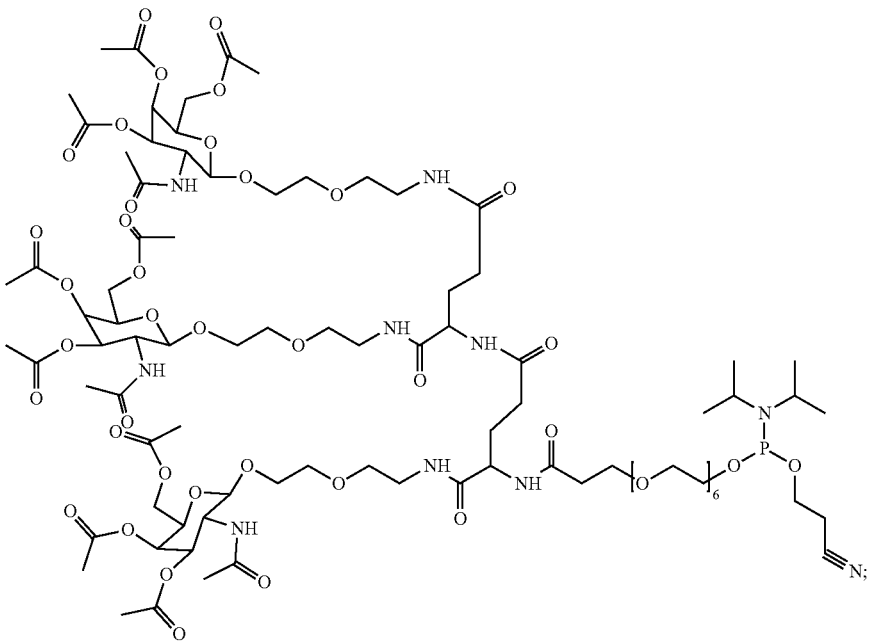

(Structure 101d)

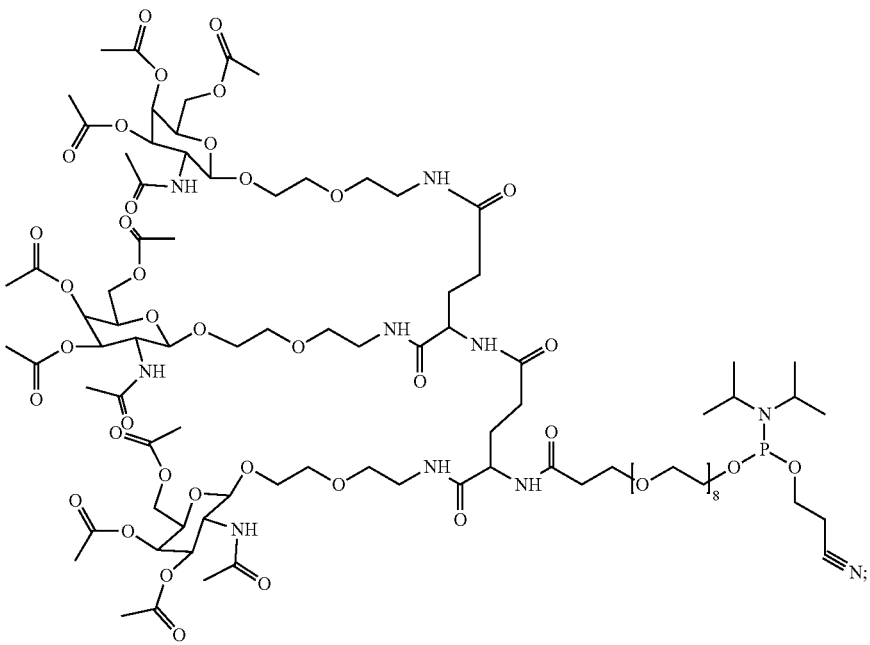

(Structure 102d)

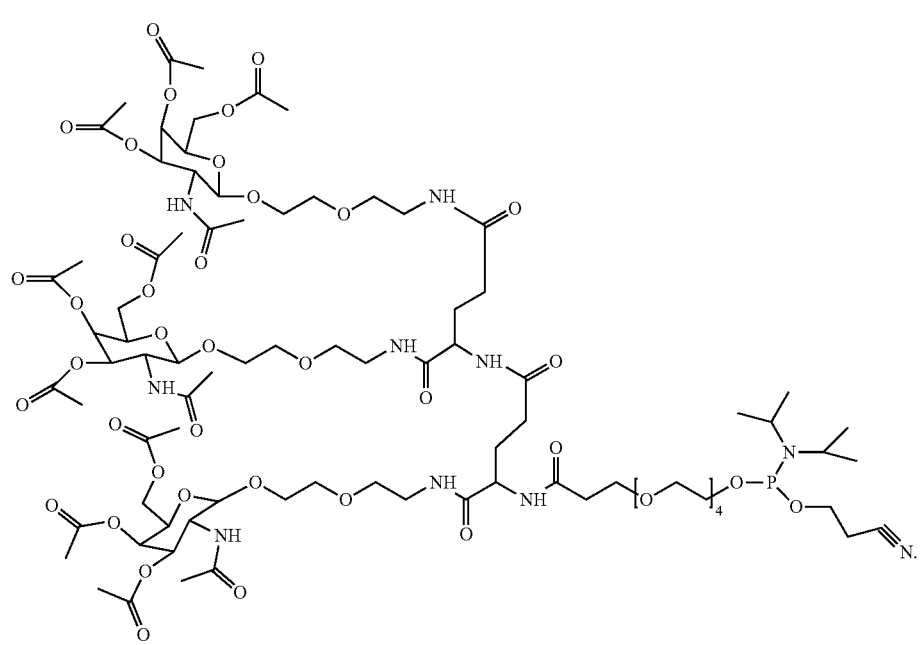
(Structure 103d)

Each of the phosphoramidite compounds of Structure 101d, 102d, and 103d, was delivered at 16 equivalents for conjugation at the 5' end of the single stranded oligonucleotide AM03704-SS, which is a sense strand that may be used in synthesizing a double-stranded RNAi agent targeting F12. AM03704 has the nucleotide sequence shown in the Table below:

TABLE 1

Sense Strand Sequence of Example 5.

| | SEQ ID NO: |
|---|---|
| Sense Strand Sequence: uauaugscsccaagaAfaGfugaaagacc(invdA) (AM03704-SS) | 1 |

Figure 9:
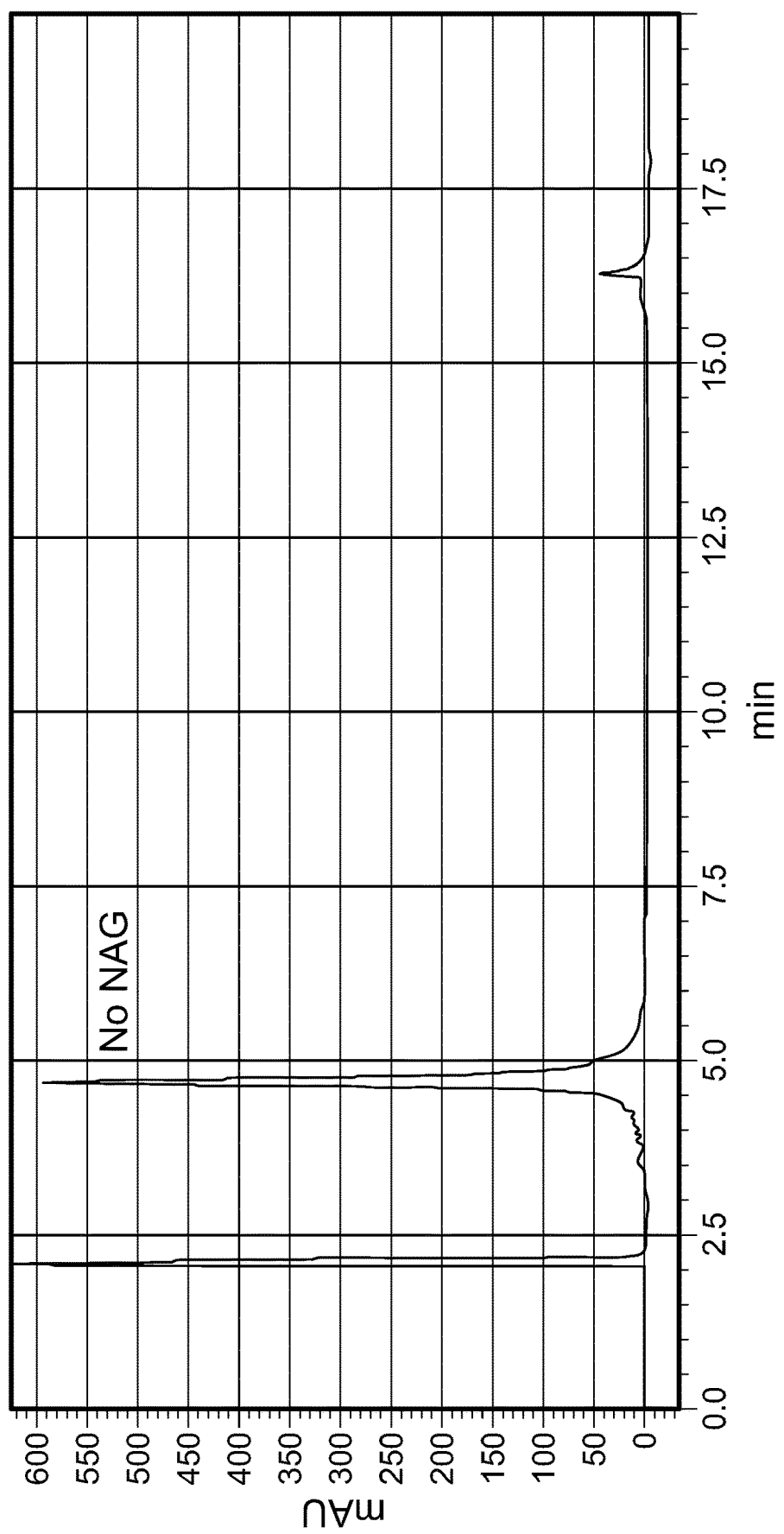
FIG. 9 is a HPLC chromatograph for AM03704 conjugated to Structure 103d (which is described below in Example 5).

The compositions were solubilized in dichloromethane (DCM) and dried over sieves. The phosphoramidite compound of Structure 103d (i.e., having a PEG-4 linker) presented gelling issues at both 0.05M and 0.25M. As shown in FIG. 9, under these conditions only a very small amount of the targeting ligand Structure 103d was able to conjugate to 5' terminal end of oligonucleotide AM03704-SS.

Figure 10:
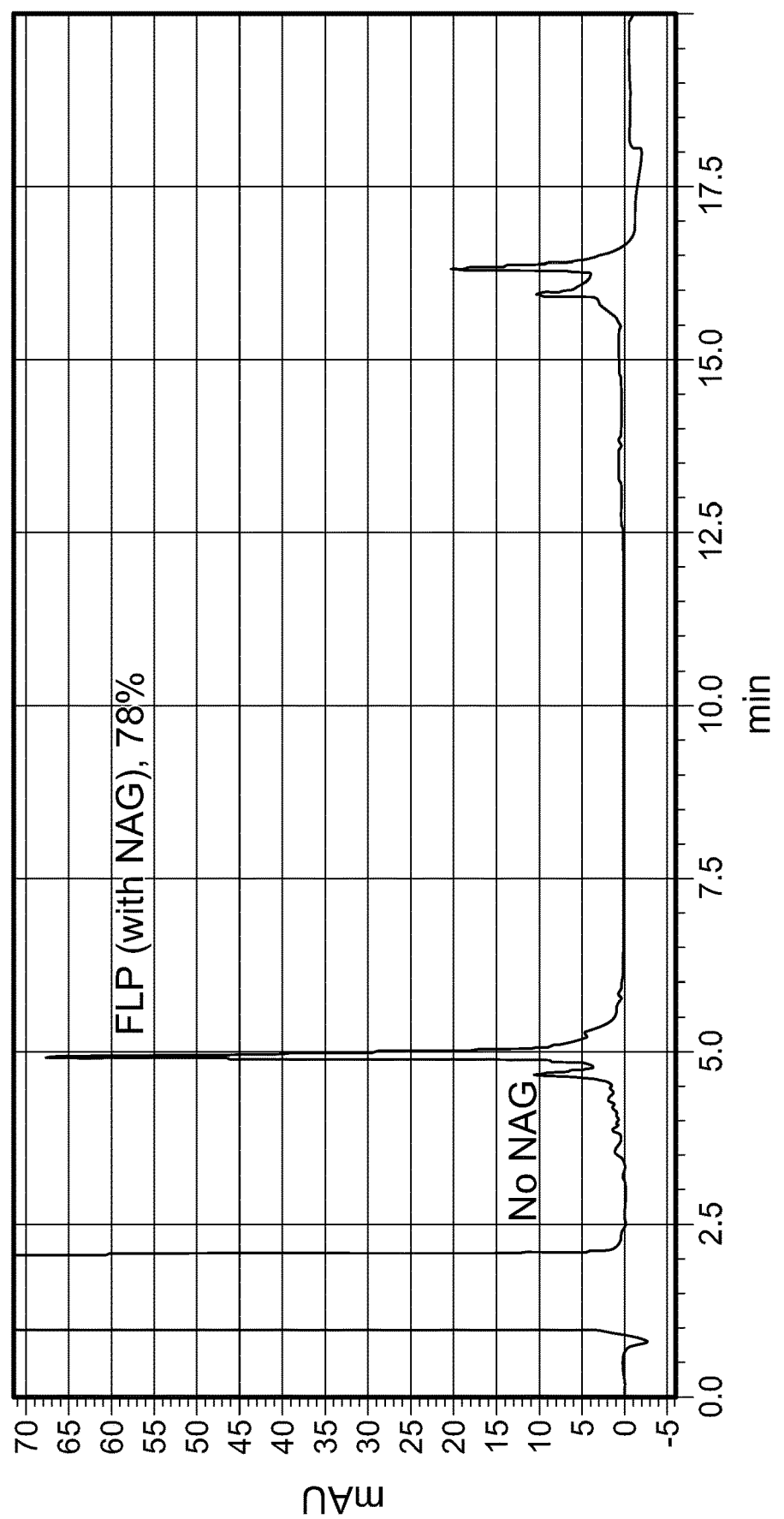
FIG. 10 is a HPLC chromatograph for AM03704 conjugated to Structure 101d (which is described below in Example 5).
Figure 11:
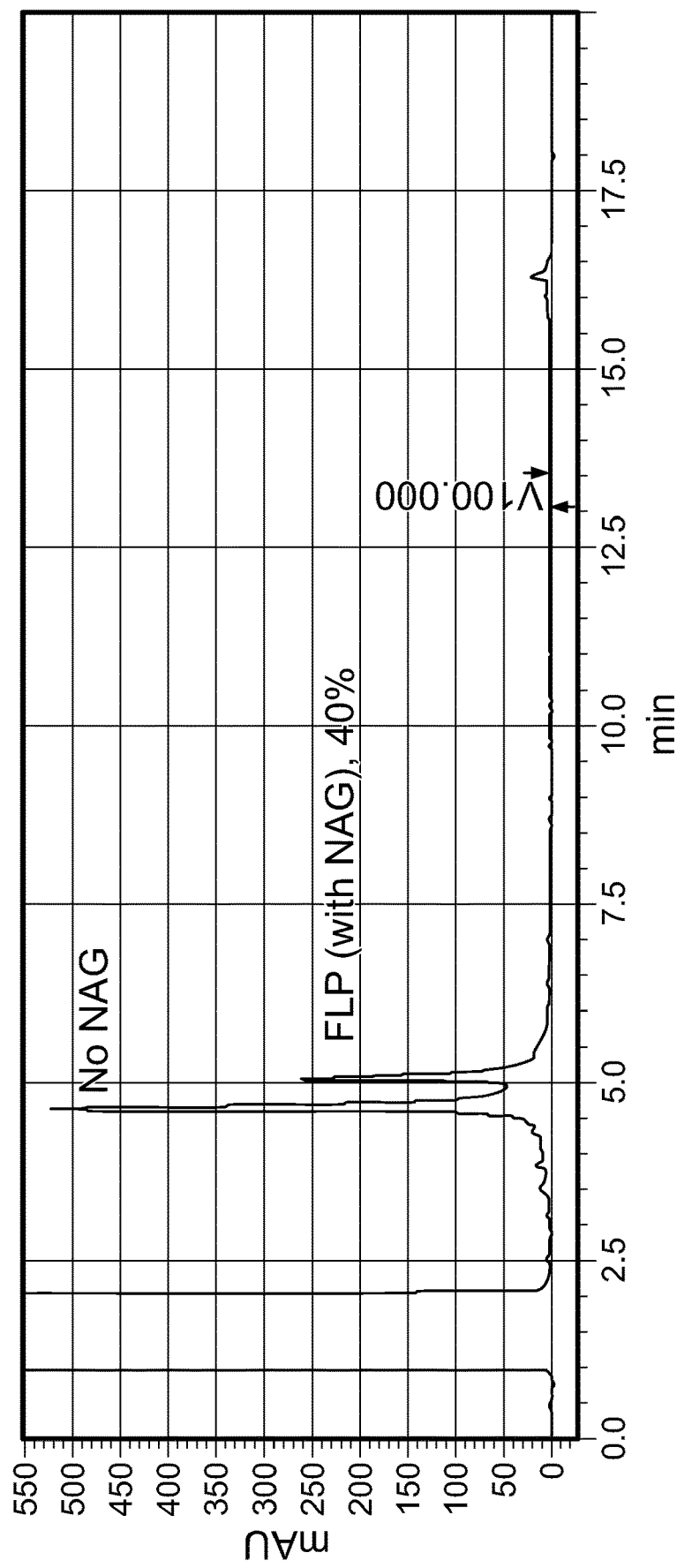
FIG. 11 is a HPLC chromatograph for AM03704 conjugated to Structure 102d (which is described below in Example 5).

Structures 101d and 102d both showed conjugation of the targeting ligand to the oligonucleotide. FIG. 9 shows the HPLC chromatograph for AM03704 conjugated to Structure 101d. It was determined that for the targeting ligand of Structure 101, approximately 78% of the targeting ligand-conjugated oligonucleotide (FLP=full length product) was formed. FIG. 10 shows the HPLC chromatograph for AM03704 conjugated to Structure 102d. Approximately 40% of the targeting ligand-conjugated oligonucleotide was formed, while approximately 60% of the oligonucleotide remained unconjugated.

Surprisingly and unexpectedly, at 16 equivalents, Structure 101d substantially outperformed both Structure 102d and Structure 103d with respect to conjugation to the oligonucleotide at the 5' end of the sequence. Additionally, both Structure 101d and 102d showed greater solubility compared to Structure 103d. As noted above, Structure 103d was difficult to dissolve using standard concentrations and solvent conditions typical for oligonucleotide synthesis. The manufacture of the targeting ligands linked to expression-inhibiting oligomeric compounds having the targeting ligand of Structure 103 (by using the phosphoramidite compound of Structure 103d) required the addition of more aggressive polar solvents.

Example 6. Comparison of 3' and 5' Sense Strand Attachment Sites for GalNAc Targeting Ligands using F12 Expression-inhibiting Oligomeric Compounds in Wild Type Mice To assess differences in the site of attachment of GalNAc ligands between the 3' and 5' terminal end of the sense strand, expression-inhibiting oligomeric compounds (double-stranded RNAi agents) directed to F12 (referred to as F12 RNAi agents herein) were prepared having the sequences set forth in the following Table 2:

TABLE 2

F12 expression-inhibiting oligomeric compounds (RNAi agent duplexes) of Example 6.

| Duplex ID: AD02803 | 5'→3' | SEQ ID NO: |
|---|---|---|
| Sense Strand Sequence: (AM03628-SS) | uAuAugscsccaagaAfaGfugaaagacca(NAG15) | 2 |
| Antisense Strand Sequence: (AM03157-AS) | usGfsgucuuUfcAfcuuUfcuugggcsuscuAu | 3 |

| Duplex ID: AD02807 | 5'→3' | SEQ ID NO: |
|---|---|---|
| Sense Strand Sequence: (AM03632-SS) | (NAG18)uauaugscsccaagaAfaGfugaaagacc(invdA) | 4 |
| Antisense Strand Sequence: (AM03157-AS) | usGfsgucuuUfcAfcuuUfcuugggcsuscuAu | 5 |

In Table 2, above, the following notations are used:

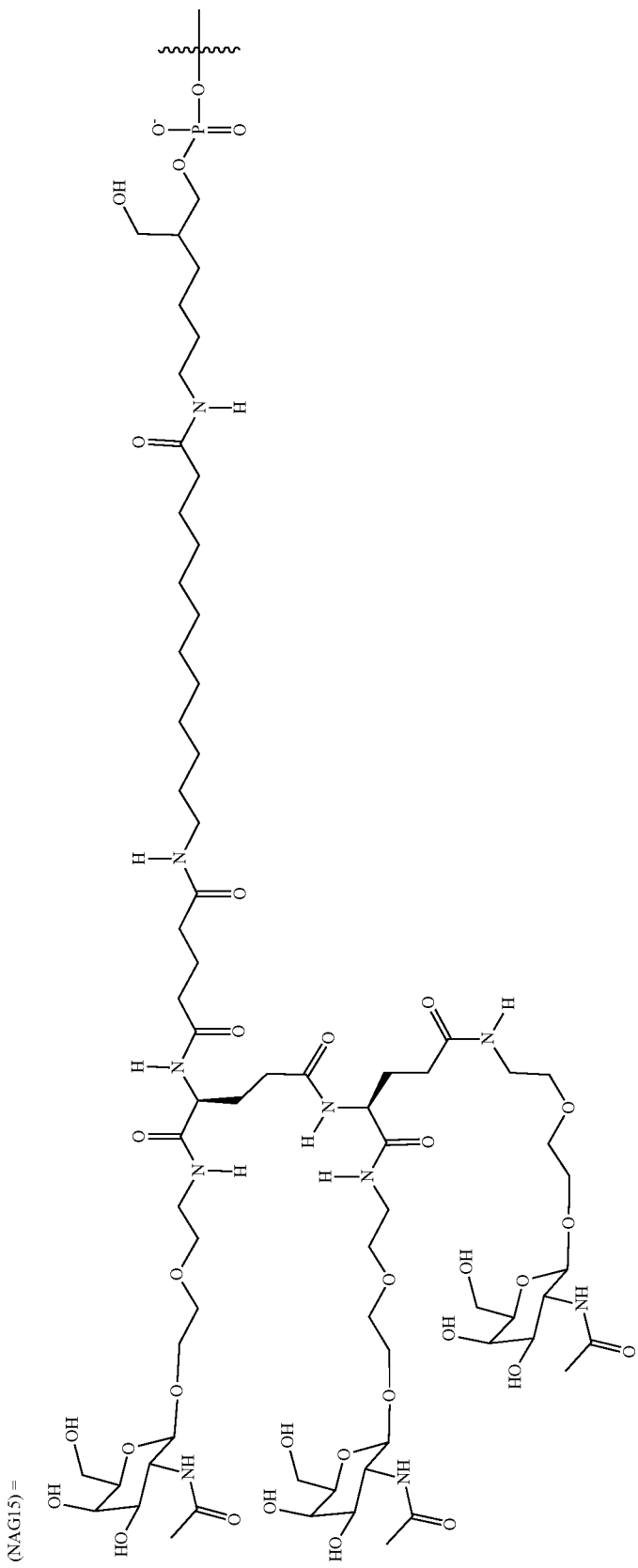

(NAG 18) = 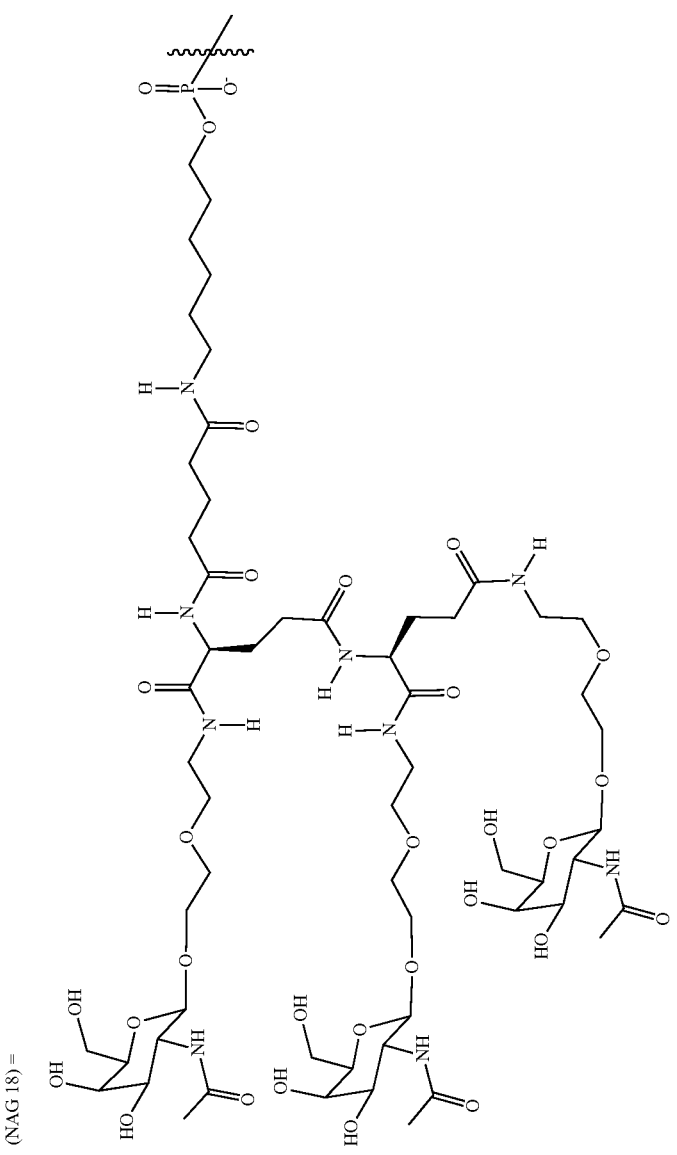

(NAG18) has the chemical structure represented by Structure 2 herein.

Each strand of the F12 RNAi agents was synthesized according to phosphoramidite technology on solid phase used in oligonucleotide synthesis using either a MerMade96E® (Bioautomation) or a MerMade12® (Bioautomation), and complementary strands were mixed by combining equimolar RNA solutions (sense and antisense) in 0.2×PBS (Phosphate-Buffered Saline, 1×, Corning, Cellgro) to form the duplexes, following the methods generally described in Example 4 herein.

The F12 RNAi agents linked to the respective GalNAc ligand (i.e., (NAG15) or (NAG18)) were combined in a pharmaceutically acceptable buffer as known in the art for subcutaneous (SC) injection.

The F12 RNAi agents linked to the respective GalNAc ligands were delivered via SC injection. On day 1, SC injection was made into the loose skin on the back between the shoulders of 200 µl solution/20 g mouse containing either saline or a 3 mg/kg (mpk) dose of one of two F12 RNAi agents (AD02803 or AD02807) in buffered saline. There were three (3) wild type mice per treatment group. As shown above, AD02803 includes (NAG15) attached to the 3' terminal end of the sense strand, while AD 2807 includes (NAG18) attached to the 5' end of the sense strand.

Serum samples from treated mice were taken on days 8, 15, 22 and 29 to monitor knockdown. Knockdown was measured by quantifying circulating mouse F12 protein (mF12) levels in serum by an internally developed mF12 alphaLISA® (Perkin Elmer). Expression at a specific bleed date was normalized to the mean of the saline control group for that same date.

Figure 12:
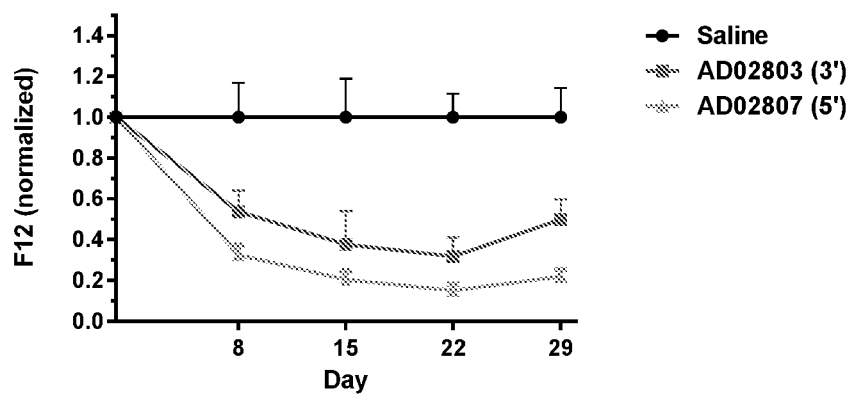
FIG. 12 is a graph illustrating normalized mouse Factor 12 (mF12) protein levels in wild type mice (which is described below in Example 6).

FIG. 12 shows the results from this study. At nadir (day 22), AD02803 showed approximately 70% reduction in circulating F12 levels, while AD02807 showed a greater than 80% reduction. The data also show a difference in length of knockdown effect, as at day 29 AD02803-treated mice showed a faster return to baseline as compared to AD2807-treated mice. These data support that the linkage of a GalNAc ligand on the 5' end of the sense strand outperforms linkage at the 3' sense strand.

Example 7. Further Comparison of 3' and 5' Sense Strand Attachment Sites for GalNAc Targeting Ligands Using F12 Expression-Inhibiting Oligomeric Compounds in Wild Type Mice To further assess the site of attachment of GalNAc ligands on the 3' and 5' terminal ends of the sense strand of double-stranded expression-inhibiting oligomeric compounds (double-stranded RNAi agents), compositions directed to the F12 gene were prepared having the sequences set forth in the following Table 3:

TABLE 3

F12 expression-inhibiting oligomeric compounds (RNAi agent duplexes) of Example 7.

| Duplex ID: AD02815 | 5'→3' | SEQ ID NO: |
|---|---|---|
| Sense Strand Sequence: (AM03640-SS) | (NAG20)uauaugscsccaagaAfaGfugaaagacc(invdA) | 6 |
| Antisense Strand Sequence: (AM03157-AS) | usGfsgucuuUfcAfcuuUfcuugggcsuscuAu | 7 |

| Duplex ID: AD02816 | 5'→3' | SEQ ID NO: |
|---|---|---|
| Sense Strand Sequence: (AM03641-SS) | uAuAugscsccaagaAfaGfugaaagacca(NAG20) | 8 |
| Antisense Strand Sequence: (AM03157-AS) | usGfsgucuuUfcAfcuuUfcuugggcsuscuAu | 9 |

In Table 3, above, the following notations are used:

(NAG20) =

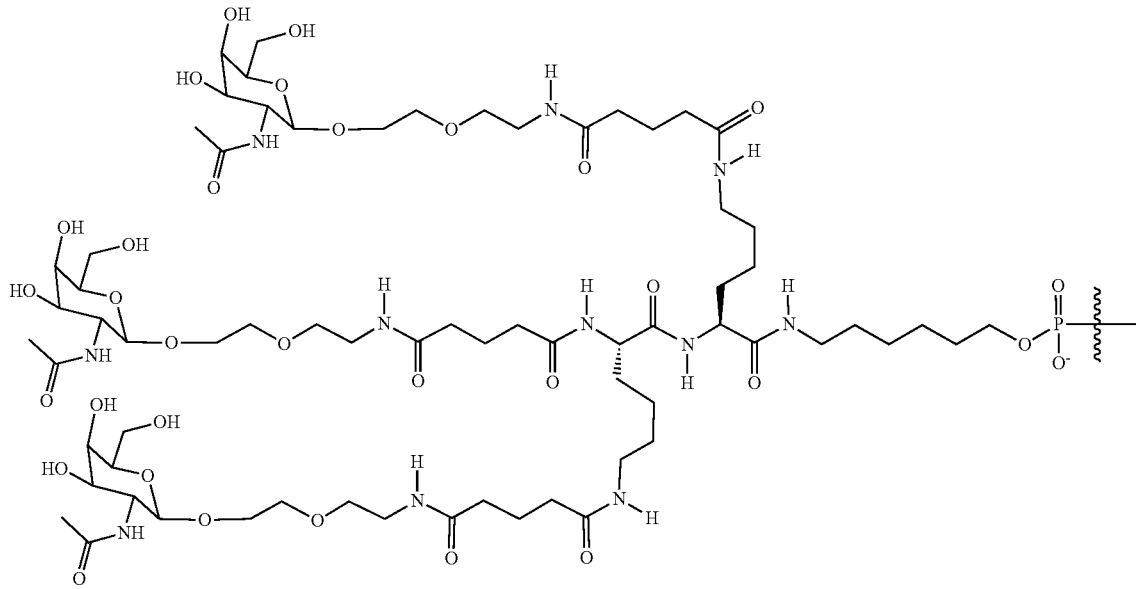

(NAG20) has the chemical structure represented by Structure 4 herein.

Each strand of the F12 RNAi agents was synthesized according to phosphoramidite technology on solid phase used in oligonucleotide synthesis using either a MerMade96E® (Bioautomation) or a MerMade12® (Bioautomation), and complementary strands were mixed by combining equimolar RNA solutions (sense and antisense) in 0.2×PBS (Phosphate-Buffered Saline, 1×, Corning, Cellgro) to form the duplexes, following the methods generally described in Example 4 herein.

The F12 RNAi agents linked to the respective GalNAc ligand (i.e., (NAG20)) were combined in a pharmaceutically acceptable buffer as known in the art for subcutaneous (SC) injection.

The F12 RNAi agents linked to the respective GalNAc ligand were delivered via SC injection. On day 1, SC injection was made into the loose skin on the back between the shoulders of 200 μl solution/20 g mouse containing either saline or a 3 mg/kg (mpk) dose of one of the two RNAi agents (AD02815 or AD02816) in buffered saline. There were three (3) wild type mice per treatment group. As shown above in Table 3, AD02815 includes (NAG20) attached to the 5' end of the sense strand, while AD02816 includes (NAG20) attached to the 3' terminal end of the sense strand.

Serum samples from treated mice were taken on days 8, 15, 22 and 29 to monitor knockdown. Knockdown was measured by quantifying circulating mouse F12 protein (mF12) levels in serum by an internally developed mF12 alphaLISA® (Perkin Elmer). Expression at a specific bleed date was normalized to the mean of the saline control group for that same date.

Figure 13:
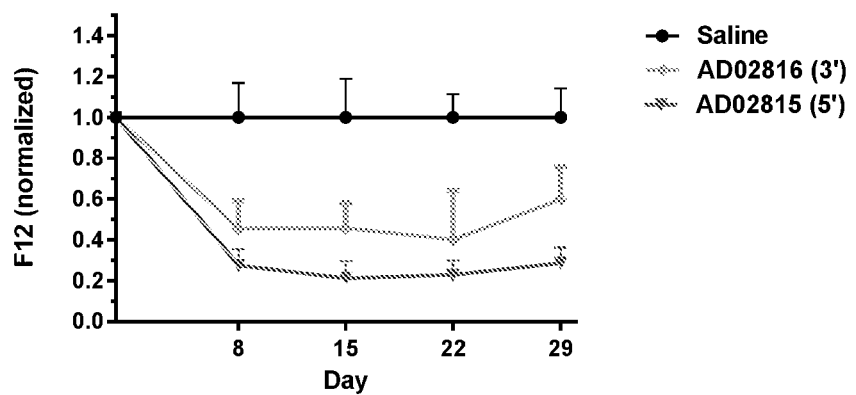
FIG. 13 is a graph illustrating normalized mouse Factor 12 (F12) protein levels in wild type mice (which is described below in Example 7).

FIG. 13 shows the results from this experiment. At nadir (day 22), AD02816 showed approximately 60% reduction in circulating F12 protein levels, while AD02815 showed a 79% reduction. The data also show a difference in length of knockdown effect. At day 29, AD02816-treated mice show 40% knockdown while AD02815-treated mice show 71% knockdown from saline levels. These data support linkage of a GalNAc ligand at the 5' terminal end of the sense strand.

Example 8. Lp(a) Expression-Inhibiting Oligomeric Compounds (Double-Stranded RNAi Agents) Linked to Targeting Ligands of Structure 101 in Lp(a) Transgenic (Tg) Mice Lp(a) expression-inhibiting oligomeric compounds (double-stranded Lp(a) RNAi agents) were prepared having the sequences set forth in the following Table 5:

TABLE 4

LP(a) expression-inhibiting oligomeric compounds (RNAi agent duplexes) of Example 8.

| Duplex ID: AD03547 | 5'→3' | SEQ ID NO: |
|---|---|---|
| Sense Strand Sequence: (AM04498-SS) | (NAG29)uauauaasuuaucgaGfGfcucauucucsa(invAb) | 10 |
| Antisense Strand Sequence: (AM04507-AS) | usGfsasGfaAfuGfaGfccuCfgAfuAfausuAUAUA | 11 |

TABLE 4-continued
LP(a) expression-inhibiting oligomeric compounds (RNAi agent duplexes) of Example 8.
| Duplex ID: AD03549 | 5'→3' | SEQ ID NO: |
|---|---|---|
| Sense Strand Sequence: (AM04502-SS) | (NAG25)uauauaasuuaucgaGfGfcucauucucsa(invAb) | 12 |
| Antisense Strand Sequence: (AM04507-AS) | usGfsasGfaAfuGfaGfccuCfgAfuAfausuAUAUA | 13 |
In Table 4, above, the following notations are used:
(NAG25) =
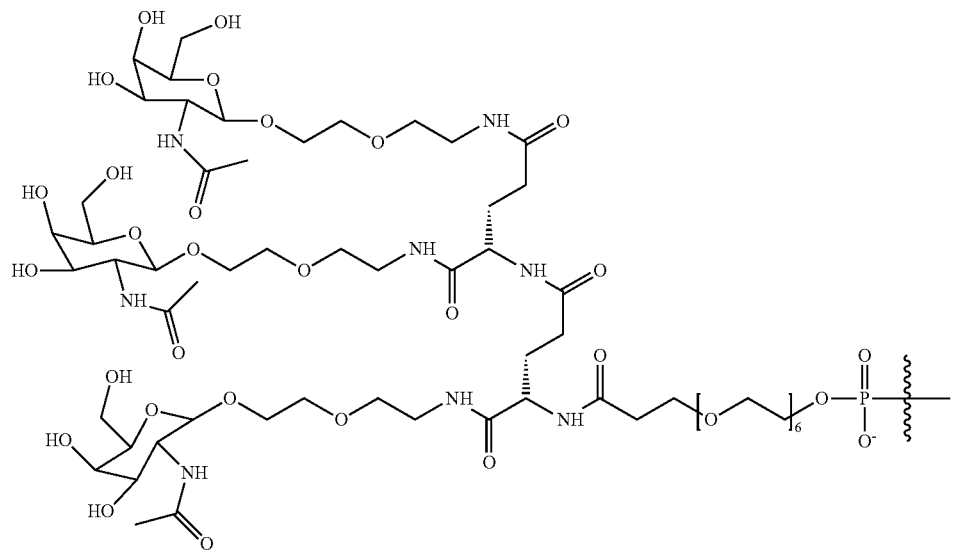
(NAG29) =
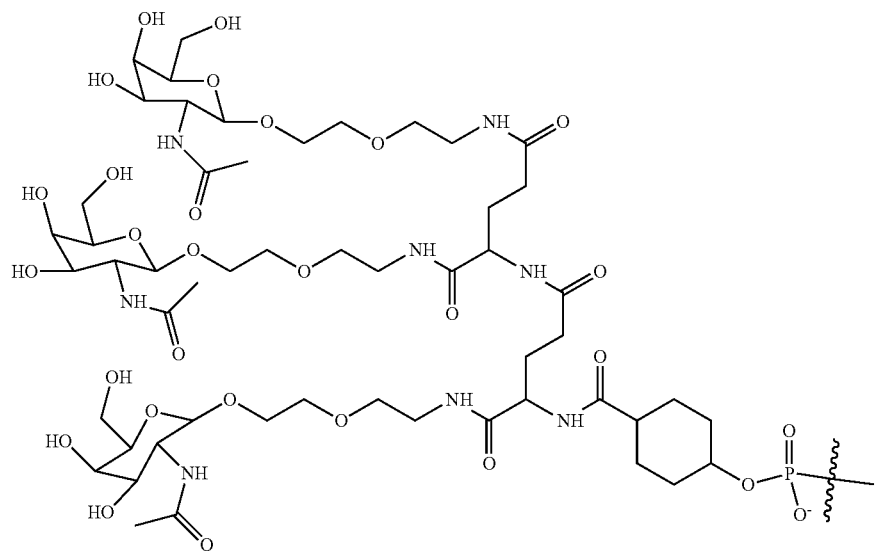

(NAG25) has the chemical structure represented by Structure 101 herein.

Each strand of the Lp(a) RNAi agents was synthesized according to phosphoramidite technology on solid phase used in oligonucleotide synthesis using either a MerMade96E® (Bioautomation) or a MerMade12® (Bioautomation), and complementary strands were mixed by combining equimolar RNA solutions (sense and antisense) in 0.2×PBS (Phosphate-Buffered Saline, 1×, Corning, Cellgro) to form the duplexes, following the methods generally described in Example 4 herein.

Lp(a) transgenic (Tg) mice (Frazer K A et al 1995, Nature Genetics 9:424-431) were used to evaluate the efficacy of double-stranded RNAi agents with conjugated N-acetylgalactosamine ligands in vivo. This mouse expresses human apo(a) from a YAC containing the full LPA gene (encoding apo(a) protein) with additional sequences both 5' and 3', as well as the human apoB-100, thereby producing humanized Lp(a) particles (hereinafter referred to as "Lp(a) Tg mice.") (Callow M J et al 1994, PNAS 91:2130-2134).

The Lp(a) RNAi agents linked to the respective GalNAc ligands (i.e., (NAG25) or (NAG29)) were combined in a pharmaceutically acceptable buffer as known in the art for subcutaneous (SC) injection.

The Lp(a) RNAi agents linked to the respective GalNAc ligands (i.e., (NAG25) or (NAG29)) at the 5' end of the sense strand were delivered via SC injection. On day 1, SC injection was made into the loose skin on the back between the shoulders of 200 μl solution/20 g mouse containing either saline or a 1 mg/kg (mpk) dose of the respective Lp(a) RNAi agent (AD03547 or AD03549) in buffered saline. There were four (4) Lp(a) Tg mice per treatment group.

Serum samples from treated mice were taken on days −1 (pre-dose), 5, 11, 16, 22, 29, and 36. Knockdown was determined by calculating circulating Lp(a) particle levels in serum. Lp(a) particle levels were measured on a Cobas® Integra 400 (Roche Diagnostics) according to the manufacturer's recommendations. For normalization, Lp(a) level for each animal at a time point was divided by the pre-dose level of expression in that animal (in this case at day −1) to determine the ratio of expression "normalized to day −1." Expression at a specific time point was then normalized to the saline control group by dividing the "normalized to day −1" ratio for an individual animal by the mean "normalized to day −1" ratio of all mice in the saline control group. This resulted in expression for each time point normalized to that in the control group. Experimental error is given as standard deviation.

Figure 14:
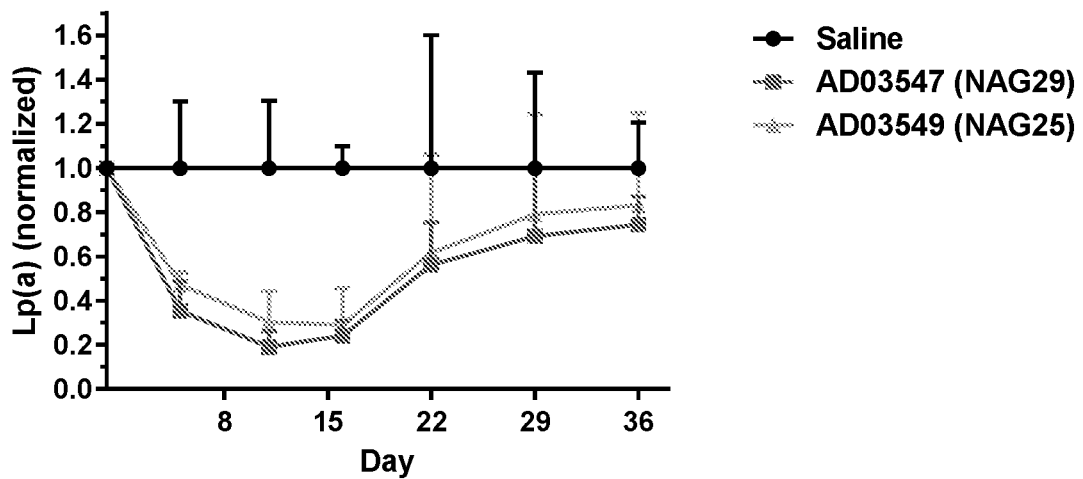
FIG. 14 is a graph illustrating normalized lipoprotein(a) (Lp(a)) particle levels in Lp(a) transgenic (Tg) mice (which is described below in Example 8).

Results are shown in FIG. 14. AD03549 (NAG25) showed 71% knockdown at nadir (day 16), and AD03547 (NAG29) showed 81% knockdown at nadir (day 11). Both triggers showed similar recovery curves after nadir, with less than 26% knockdown on day 36. These data support that the GalNAc ligands shown are comparable in both initial knockdown activity and duration of knockdown in Lp(a) Tg mice with a single 1 mg/kg dose.

Example 9. Lp(a) Knockdown in Lp(a) transgenic (Tg) Mice Following Administration of Lp(a) Expression-inhibiting Oligomeric Compounds (Double-stranded RNAi agents) Linked to Targeting Ligand Structure 101

Lp(a) expression-inhibiting oligomeric compounds (double-stranded Lp(a) RNAi agents) were prepared having the sequences set forth in the following Table 5:

TABLE 5

LP(a) expression-inhibiting oligomeric compounds (RNAi agent duplexes) of Example 9.

| Duplex ID: AD03272 | 5'→3' | SEQ ID NO: |
|---|---|---|
| Sense Strand Sequence: (AM04138-SS) | (NAG25)uauausasguuaucgAfGfGfcucauucuc(invdA) | 14 |
| Antisense Strand Sequence: (AM02860-AS) | usGfsaGfaAfuGfaGfccuCfgAfuAfaCfucsusuAu | 15 |

In Table 5, (NAG25) is the same structure as shown in Example 8, above, and has the chemical structure represented by Structure 101 herein.

Each strand of the Lp(a) RNAi agents was synthesized according to phosphoramidite technology on solid phase used in oligonucleotide synthesis using either a MerMade96E® (Bioautomation) or a MerMade12® (Bioautomation), and complementary strands were mixed by combining equimolar RNA solutions (sense and antisense) in 0.2×PBS (Phosphate-Buffered Saline, 1×, Corning, Cellgro) to form the duplexes, following the methods generally described in Example 4 herein.

Lp(a) Tg mice were used to evaluate the efficacy of double-stranded RNAi agents with conjugated N-acetylgalactosamine ligands in vivo.

The Lp(a) RNAi agent linked to targeting ligand Structure 101 was combined in a pharmaceutically acceptable buffer as known in the art for subcutaneous (SC) injection.

The Lp(a) RNAi agent linked to the targeting ligand at the 5' end of the sense strand was delivered via SC injection. On day 1, a SC injection was administered into the loose skin on the back between the shoulders at 200 μl solution/20 g mouse of either saline or a 1 mg/kg (mpk) dose of RNAi agent AD03272 in buffered saline. There were four (4) Lp(a) Tg mice per treatment group.

Serum samples from treated mice were taken on days −1 (pre-dose), 8, 15, 22, 29, 36, and 43. Knockdown was determined by calculating circulating Lp(a) particle levels in serum. Lp(a) particle levels were measured on a Cobas® Integra 400 (Roche Diagnostics) according to the manufacturer's recommendations. For normalization, Lp(a) level for each animal at a time point was divided by the pre-dose level of expression in that animal (in this case at day −1) to determine the ratio of expression "normalized to day −1." Expression at a specific time point was then normalized to the saline control group by dividing the "normalized to day −1" ratio for an individual animal by the mean "normalized to day −1" ratio of all mice in the saline control group. This resulted in expression for each time point normalized to that in the control group. Experimental error is given as standard deviation.

Figure 15:
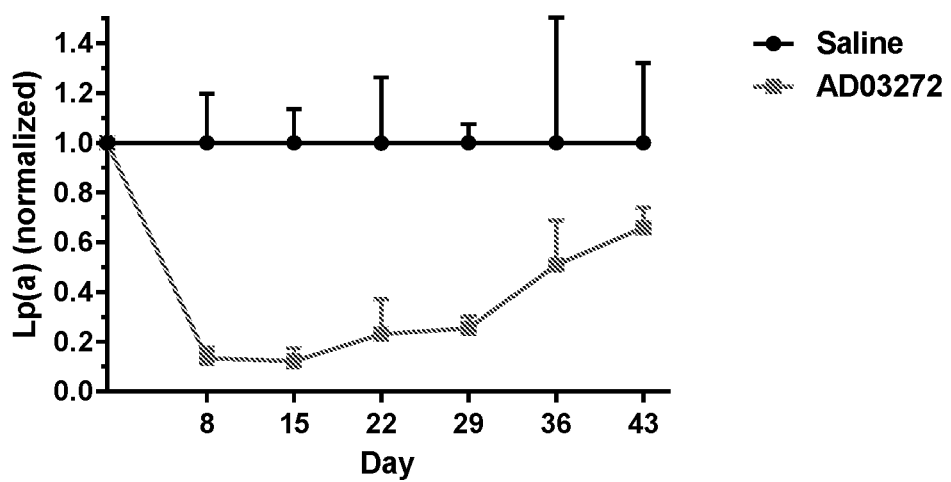
FIG. 15 is a graph illustrating normalized lipoprotein(a) (Lp(a)) particle levels in Lp(a) Tg mice (which is described below in Example 9).

Results are shown in FIG. 15. AD03272 showed 88% knockdown at nadir (day 15), and maintained knockdown of 75% at day 29. These data support that the targeting ligand of Structure 1008 can target LPA-targeted RNAi agents to the liver and obtain >85% knockdown with a single 1 mg/kg dose in transgenic mice.

Example 10. Apolipoprotein(a) (apo(a)) Knockdown in apo(a) Transgenic (Tg) Mice Following Administration of Lp(a) Expression-inhibiting Oligomeric Compounds (Double-stranded RNAi Agents) Linked to Targeting Ligand Structures 101, 102, and 103

Lp(a) expression-inhibiting oligomeric compounds (double-stranded Lp(a) RNAi agents) were prepared having the sequences set forth in the following Table 4:

TABLE 6

LP(a) expression-inhibiting oligomeric compounds (RNAi agent duplexes) of Example 10.

| Duplex ID: AD03275 | 5'→3' | SEQ ID NO: |
|---|---|---|
| Sense Strand Sequence: (AM04138-SS) | (NAG25)uauausasguuaucgAfGfGfcucauucuc(invdA) | 16 |
| Antisense Strand Sequence: (AM04133-AS) | usGfsagaauGfaGfccuCfgauaacucsusuau | 17 |

| Duplex ID: AD03341 | 5'→3' | SEQ ID NO: |
|---|---|---|
| Sense Strand Sequence: (AM04233-SS) | (NAG26)uauausasguuaucgAfGfGfcucauucuCM(invdA) | 18 |
| Antisense Strand Sequence: (AM04133-AS) | usGfsagaauGfaGfccuCfgauaacucsusuau | 19 |

| Duplex ID: AD03421 | 5'→3' | SEQ ID NO: |
|---|---|---|
| Sense Strand Sequence: (AM04372-SS) | (NAG27)uauausasguuaucgAfGfGfcucauucuCM(invdA) | 20 |
| Antisense Strand Sequence: (AM04133-AS) | usGfsagaauGfaGfccuCfgauaacucsusuau | 21 |

In Table 6, above, the following notations are used:

(NAG26) =

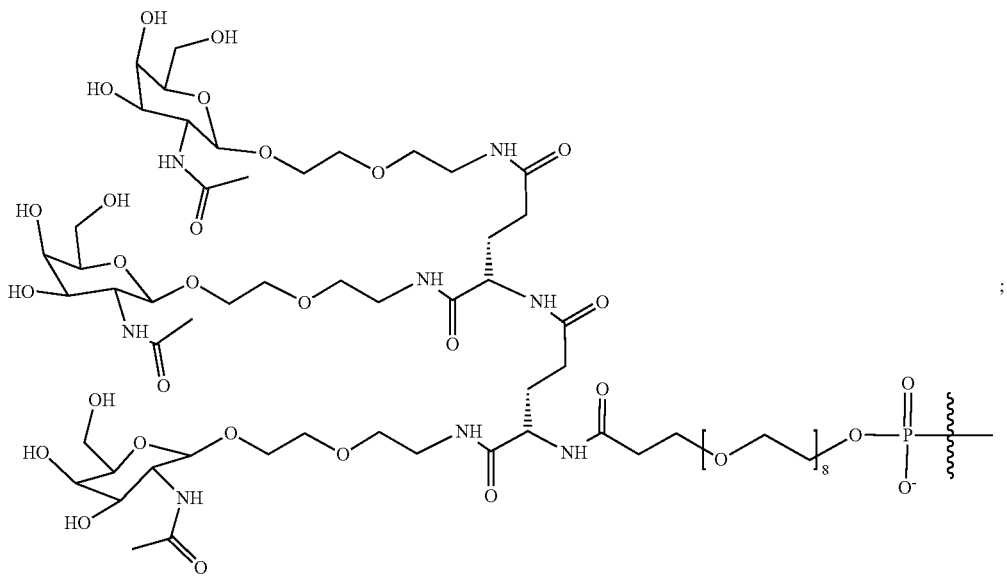

(NAG27) =

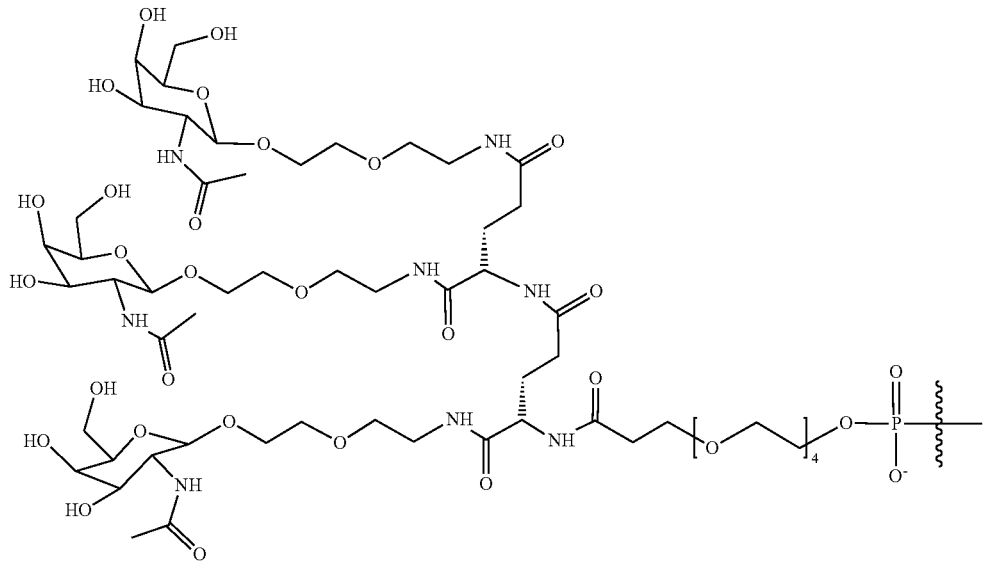

Additionally, (NAG25) is the same structure as shown in Example 8, above, and has the chemical structure represented by Structure 101 herein. (NAG26) has the chemical structure represented by Structure 102 herein. (NAG27) has the chemical structure represented by Structure 103 herein. As shown above in Table 7, other than the different targeting ligand selected, the compositions are identical.

Each strand of the Lp(a) RNAi agents was synthesized according to phosphoramidite technology on solid phase used in oligonucleotide synthesis using either a MerMade96E® (Bioautomation) or a MerMade12® (Bioautomation), and complementary strands were mixed by combining equimolar RNA solutions (sense and antisense) in 0.2×PBS (Phosphate-Buffered Saline, 1×, Corning, Cellgro) to form the duplexes, following the methods generally described in Example 10 herein.

Apo(a) transgenic (Tg) mice were used to evaluate the efficacy of double-stranded RNAi agents with conjugated N-acetyl-galactosamine ligands in vivo. Apo(a) Tg mice (Frazer K A et al 1995, Nature Genetics 9:424-431) express human apo(a) from a YAC containing the full LPA gene (encoding apo(a) protein) with additional sequences both 5' and 3' (hereinafter referred to as "apo(a) Tg mice").

The Lp(a) RNAi agents linked to the respective GalNAc ligands (i.e., (NAG25), (NAG26), or (NAG27)) were combined in a pharmaceutically acceptable buffer as known in the art for subcutaneous (SC) injection.

The Lp(a) RNAi agents linked to the respective GalNAc ligands (i.e., (NAG25), (NAG26), or (NAG27)) at the 5' end of the sense strand were delivered via SC injection. On day 1, a SC injection was administered into the loose skin on the back between the shoulders of 200 µl solution/20 g mouse containing either saline or a 1 mg/kg (mpk) dose of the respective RNAi agent (AD03275, AD03341, or AD03421) in buffered saline. There were three (3) apo(a) Tg mice per treatment group.

Serum samples from treated mice were taken on days −1 (pre-dose), 8, 15, 22, 29, 36 and 43. Knockdown was determined by monitoring circulating apo(a) protein levels in serum using an ELISA for apo(a) (Abcam). For normalization, apo(a) level for each animal at a time point was divided by the pre-treatment level of expression in that animal (in this case at day −1) to determine the ratio of expression "normalized to day −1". Expression at a specific time point was then normalized to the saline control group by dividing the "normalized to day −1" ratio for an individual animal by the mean "normalized to day −1" ratio of all mice in the saline control group. This resulted in expression for each time point normalized to that in the control group. Experimental error is given as standard error of the mean.

Figure 16:
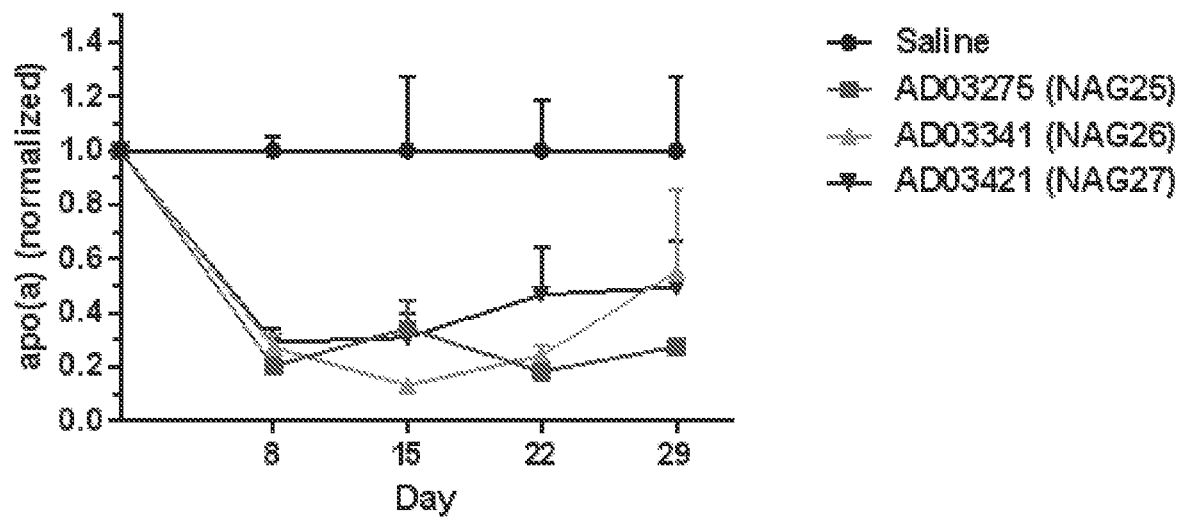
FIG. 16 is a graph illustrating normalized apo(a) levels in apo(a) transgenic (Tg) mice (which is described below in Example 10).

Results are shown in FIG. 16. Lp(a) RNAi agent AD03275, containing targeting ligand Structure 101 (NAG25), showed 82% knockdown at nadir (day 22), and maintained knockdown of 72% at day 29. Lp(a) RNAi agent AD03341, containing targeting ligand Structure 102 (NAG26), showed 87% knockdown at nadir (day 15), however, knockdown at day 29 was 45%, indicating an increased return to pre-dose apo(a) levels. Lp(a) RNAi agent AD03421, containing targeting ligand Structure 103 (NAG27), showed 70% knockdown at nadir (day 15), and knockdown at day 29 was 50%. These data support that Structure 101 (NAG25), Structure 102 (NAG26), and Structure 103 (NAG27), all initially show similar knockdown activity. However, these data also show that AD03275 (Structure 101 (NAG25)) has superior duration and maintains knockdown (72% knockdown on day 29) better than Structure 102 (NAG26) and Structure 103 (NAG27).

Example 11. LP(a) Expression-Inhibiting Oligomeric Compounds (Double-Stranded RNAi Agents) Linked to Targeting Ligand Structure 101 in Cynomolgus Monkeys Five different LPA RNAi agents linked to targeting ligand represented by structure 101 were prepared to evaluate their performance in cynomolgus macaque (*Macaca fascicularis*) primates: AD03460, AD03536, AD03851, AD03853, and AD04110.

Each strand of the Lp(a) RNAi agents was synthesized according to phosphoramidite technology on solid phase used in oligonucleotide synthesis using either a MerMade96E® (Bioautomation) or a MerMade12® (Bioautomation), and complementary strands were mixed by combining equimolar RNA solutions (sense and antisense) in 0.2×PBS (Phosphate-Buffered Saline, 1×, Corning, Cellgro) to form the duplexes, following the methods generally described in Example 4 herein.

The targeting ligands for all five (5) Lp(a) RNAi agents were added to the 5' terminal end of the sense strand, using non-nucleoside phosphoramidite synthesis generally described herein and known in the art. The targeting ligand for each of the Lp(a) RNAi agents was linked to the 5' terminal end of the respective RNAi agent using the following phosphoramidite compound:

(Structure 101d)
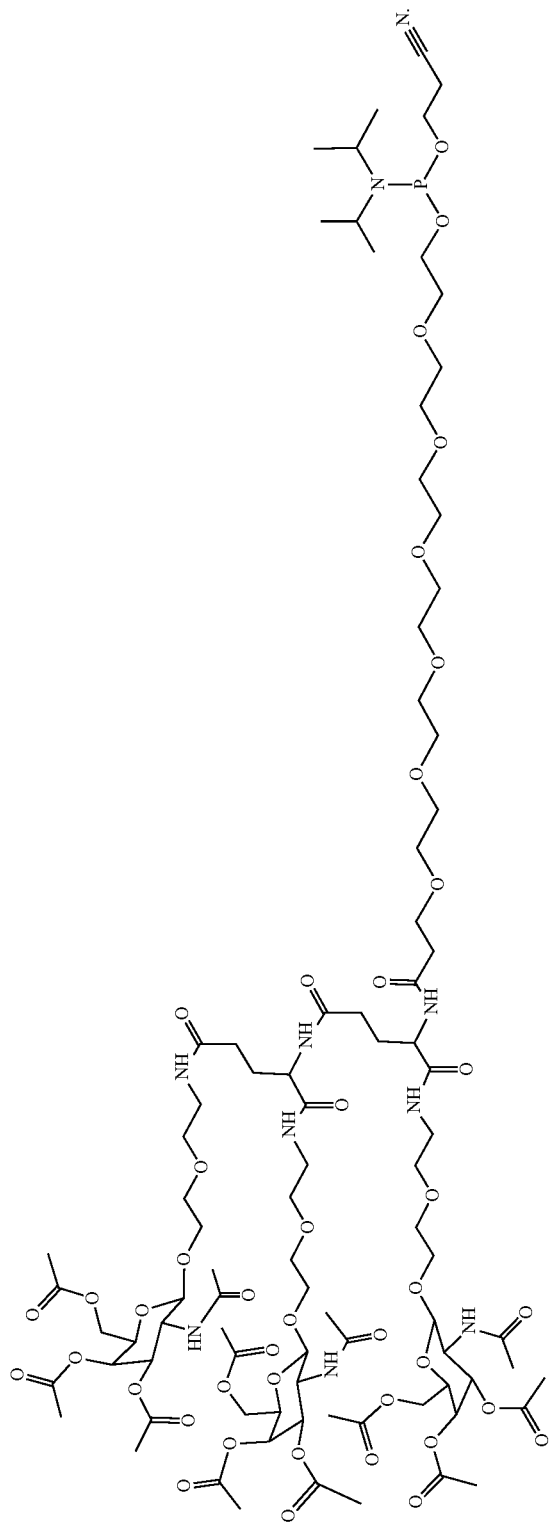

AD03460 and AD03536 included targeting ligand (NAG25) conjugated to the 5' end of the sense strand of the respective RNAi agent. (NAG25) has the same structure as shown in Example 8, above.

AD03851, AD03853, and AD04110 contained targeting ligand (NAG25)s conjugated to the 5' end of the sense strand of the respective RNAi agent.

(NAG25)s =

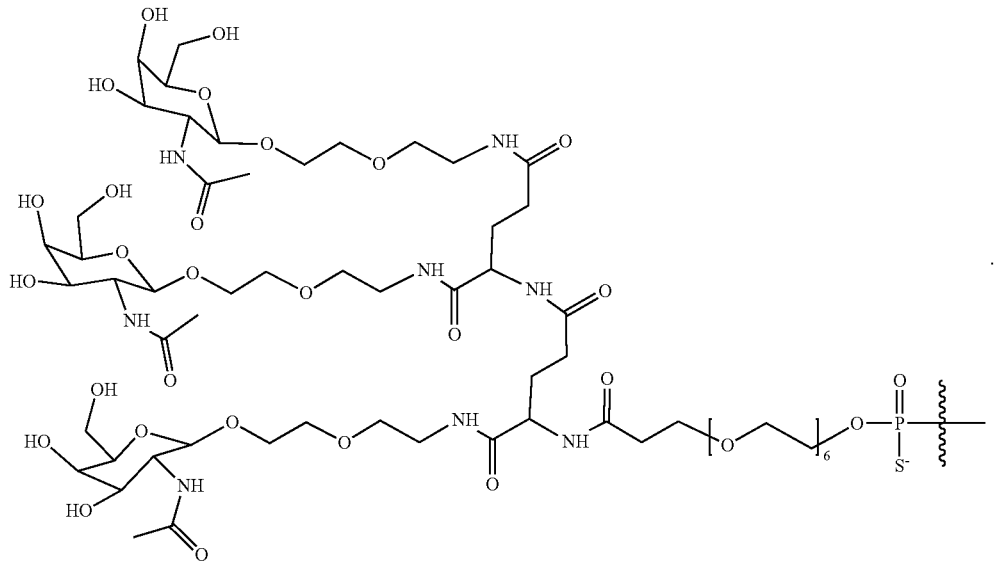

Blood samples were drawn and analyzed for Lipoprotein (a) levels on day 8 and day 15. Lp(a) levels were normalized to average of three pre-dose values. Normalized Lp(a) levels are reported in the following table:

|  | Normalized Lp(a) Day 8 | Normalized Lp(a) Day 15 |
| --- | --- | --- |
| Saline | 1.01 ± 0.06 | 1.15 ± 0.07 |
| AD03460 | 0.68 ± 0.12 | 0.40 ± 0.13 |
| AD03536 | 0.54 ± 0.07 | 0.21 ± 0.06 |
| AD03851 | 0.41 ± 0.08 | 0.18 ± 0.08 |
| AD03853 | 0.50 ± 0.23 | 0.27 ± 0.17 |
| AD04110 | 0.59 ± 0.13 | 0.43 ± 0.10 |

These data show that significant knockdown was achieved in cynomolgus monkeys at 2 mg/kg (mpk) doses of multiple different Lp(a) RNAi agents conjugated to the same targeting ligand structure of Structure 101 herein.

Example 12: F12 Expression-Inhibiting Oligomeric Compounds (Double-Stranded RNAi Agents) Linked to Targeting Ligands of Structure 101 in Cynomolgus Monkeys F12 expression-inhibiting oligomeric compounds (double-stranded F12 RNAi agents) were prepared having the sequences set forth in the following Table 7:

TABLE 7

F12 expression-inhibiting oligomeric compounds (RNAi agent duplexes) of Example 12.

| Duplex ID: AD03635 | 5'→3' | SEQ ID NO: |
| --- | --- | --- |
| Sense Strand Sequence: (AM04130-SS) | (NAG25)uauaugscsccaagaAfaGfugaaagacc(invdA) | 22 |
| Antisense Strand Sequence: (AM03157-AS) | usGfsgucuuUfcAfcuuUfcuugggcsuscuAu | 23 |

In Table 7, above, (NAG25) represents the same structure as shown in Example 8, above, and is represented by Structure 101 herein.

Each strand of the Lp(a) RNAi agents was synthesized according to phosphoramidite technology on solid phase used in oligonucleotide synthesis using either a MerMade96E® (Bioautomation) or a MerMade12® (Bioautomation), and complementary strands were mixed by combining equimolar RNA solutions (sense and antisense) in 0.2×PBS (Phosphate-Buffered Saline, 1×, Corning, Cellgro) to form the duplexes, following the methods generally described in Example 4 herein.

The F12 RNAi agent conjugated to the targeting ligand at the 5' end of the sense strand was made and combined in a pharmaceutically acceptable buffer as known in the art for subcutaneous (SC) injection.

On day 1, cynomolgus macaque (*Macaca fascicularis*) primates were injected subcutaneously with 3 mg/kg of AD03635. Three (3) monkeys were dosed per treatment group.

Serum samples from treated cynomolgus monkeys were taken on day −7 and day 1 (pre-dose), and on days 8, 15 and 22 to monitor knockdown. Knockdown was measured by quantifying circulating cyno F12 protein (cF12) levels in serum by a human F12 ELISA kit (Molecular Innovations). cF12 levels for each animal at a respective time point was divided by the pre-treatment level (average of day −7 and day 1) of expression in that animal to determine the ratio of expression "normalized to pre-dose". Experimental error is given as standard deviation.

Figure 17:
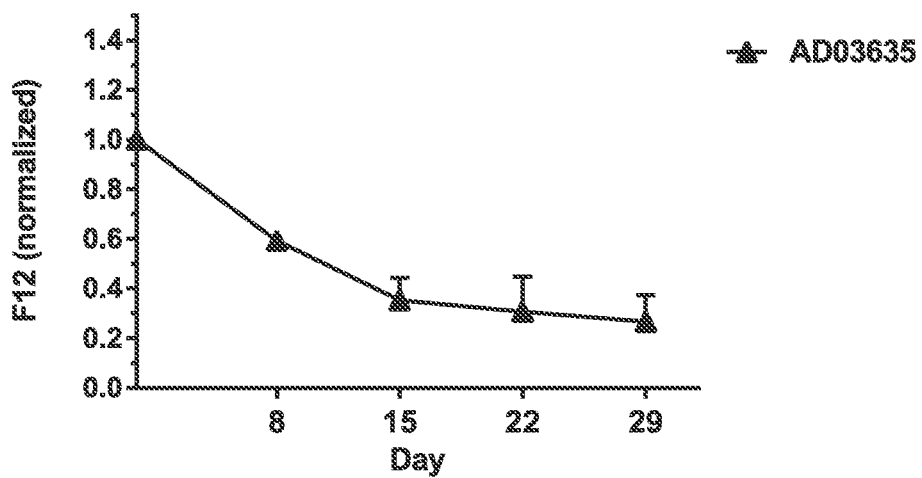
FIG. 17 is a graph illustrating normalized cF12 protein levels in cynomolgus monkeys (which is described below in Example 12).

FIG. 17 shows the results. The F12 RNAi agent linked to (NAG25) (Structure 101 herein) showed knockdown in cynomolgus monkeys.

Example 13: Alpha-1 Antitrypsin Expression-Inhibiting Oligomeric Compounds (Double-Stranded RNAi Agents) Linked to Targeting Ligands of Structure 101 in PiZ Transgenic Mice To evaluate RNAi agents directed to the alpha-1 antitrypsin (AAT) gene in vivo, a transgenic PiZ mouse model (PiZ mice) was used. PiZ mice harbor the human PiZ AAT mutant allele and model human AATD (Carlson et al., Journal of Clinical Investigation 1989).

AAT expression-inhibiting oligomeric compounds (double stranded RNAi agents) were prepared having the sequences set forth in the following Table 8:

TABLE 8

AAT expression-inhibiting oligomeric compounds (RNAi agent duplexes) of Example 13.

| Duplex ID: AD04454 | 5'→3' | SEQ ID NO: |
|---|---|---|
| Sense Strand Sequence: (AM05662-SS) | (NAG25)scsgauaucaUfCfAfccaaguuccsa(invAb) | 24 |
| Antisense Strand Sequence: (AM05663-AS) | usGfsgAfaCfuugguGfaUfgAfuAfusCfsg | 25 |

In Table 8, (NAG25)s has the chemical structure as shown in Example 11, above.

The AAT RNAi agent was prepared in a pharmaceutically acceptable saline buffer and administered by subcutaneous (SC) injection into the loose skin on the back between the shoulders of 200 µl solution/20 g mouse to PiZ mice to evaluate knockdown of AAT gene expression. Each mouse received a single SC dose of 5 mg/kg (mpk) of AD04454. Three mice were dosed with the AAT RNAi agent (n=3).

Plasma samples were drawn and analyzed for AAT (Z-AAT) protein levels on days −1, day 1 (pre-dose), day 8, and day 15. AAT levels were normalized to day 1 (pre-dose) AAT plasma levels. Protein levels were measured by quantifying circulating human Z-AAT levels in plasma by an ELISA kit.

Figure 18:
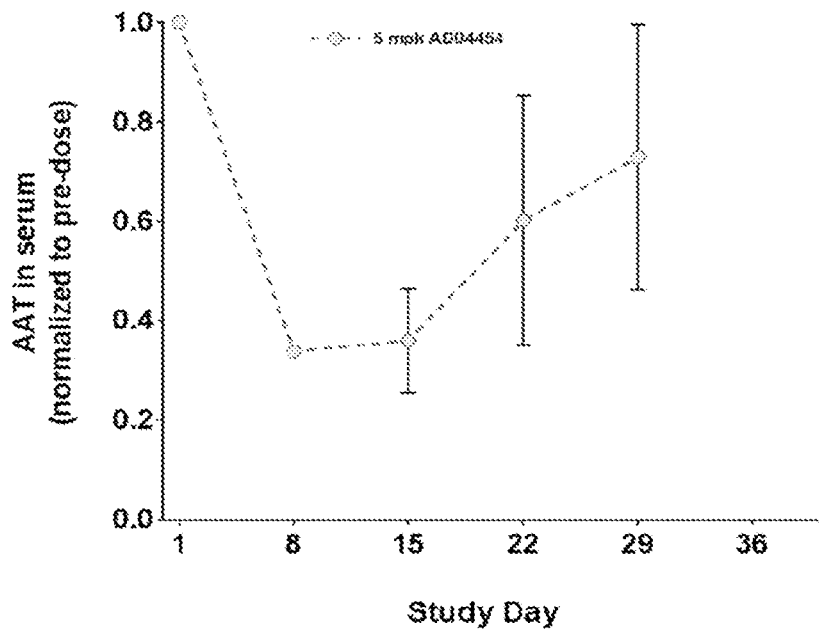
FIG. 18 is a graph illustrating normalized AAT (Z-AAT) protein levels in PiZ transgenic mice (which is described below in Example 13).

The average normalized AAT (Z-AAT) levels are shown in FIG. 18. The AAT RNAi agent linked to the targeting ligand of Structure 101 herein showed knockdown in PiZ transgenic mice.

Example 14: F12 Knockdown in Wild Type Mice Following Administration of F12 Expression-Inhibiting Oligomeric Compounds (Double-Stranded RNAi Agents) Linked to Targeting Ligands of Structure 101

F12 expression-inhibiting oligomeric compounds (double-stranded F12 RNAi agents) were prepared having the sequences set forth in the following Table 9:

TABLE 9

F12 expression-inhibiting oligomeric compounds (RNAi agent duplexes) of Example 14.

| Duplex ID: AD03632 | 5'→3' | SEQ ID NO: |
|---|---|---|
| Sense Strand Sequence: (AM04613-SS) | (NAG25)gcgaugscsccaagaAfaGfugaaagacc(invdA) | 26 |
| Antisense Strand Sequence: (AM04048-AS) | usGfsgucuuUfcAfcuuUfcuugggcsasucgc | 27 |

In Table 9, (NAG25) has the chemical structure as shown in Example 8, above, and is represented by Structure 101 disclosed herein.

Each strand of the F12 RNAi agents was synthesized according to phosphoramidite technology on solid phase used in oligonucleotide synthesis using either a MerMade96E® (Bioautomation) or a MerMade12® (Bioautomation), and complementary strands were mixed by combining equimolar RNA solutions (sense and antisense) in 0.2×PBS (Phosphate-Buffered Saline, 1×, Corning, Cellgro) to form the duplexes, following the methods generally described in Example 10 herein.

The F12 RNAi agents conjugated to the respective GalNAc targeting ligand (i.e., (NAG25)) was combined in a pharmaceutically acceptable buffer as known in the art for subcutaneous (SC) injection.

The composition was delivered via SC injection. On day 1, a SC injection was administered into the loose skin on the back between the shoulders of 200 ul solution/20 g mouse containing either saline or a 3 mg/kg (mpk) dose of AD03632 in buffered saline. There were three (3) wild type mice per treatment group. As shown above, AD03632 includes the structure (NAG25) linked at the 5' terminal end of the sense strand.

Serum samples from treated mice were taken on days −1 (pre-dose), 8, 15 22, 29 and 36 to monitor knockdown. Knockdown was measured by quantifying circulating mouse F12 protein (mF12) levels in serum by an internally developed mF12 alphaLISA® (Perkin Elmer). mF12 levels for each animal at a respective time point was divided by the pre-treatment level of expression in that animal to determine the ratio of expression "normalized to pre-dose". Expression at a specific time point was then normalized to the saline control group by dividing the "normalized to day pre-dose" ratio for an individual animal by the mean "normalized to day pre-dose" ratio of all mice in the saline control group. This resulted in expression for each time point normalized to that in the control group. Experimental error is given as standard deviation.

Figure 19:
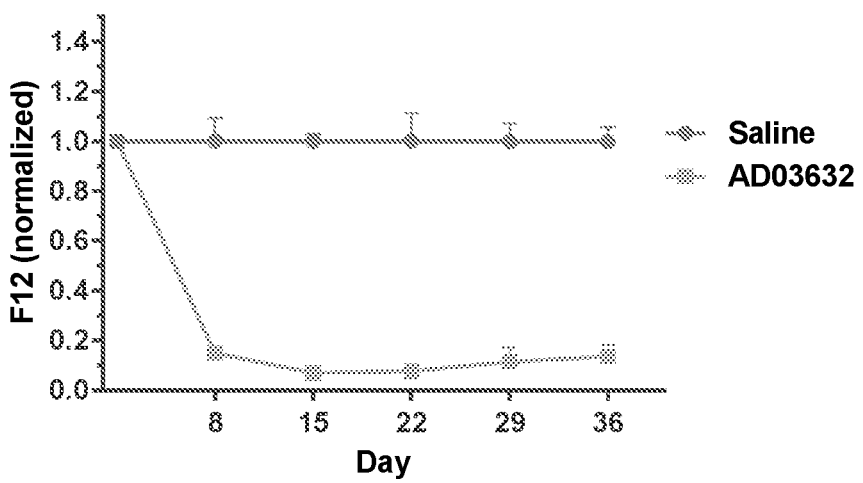
FIG. 19 is a graph illustrating normalized mouse Factor 12 (F12) protein levels in wild type mice (which is described below in Example 14).

Results from this study are shown in FIG. 19. AD03632, which includes targeting ligand Structure 101 disclosed herein attached at the 5' terminal end, shows significant knockdown across all time points.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

The invention claimed is:

1. A targeting ligand selected from the group consisting of:

[chemical structures]

and wherein Targeting Moiety is selected from the group consisting of: carbohydrates, glycans, haptens, vitamins, folate, biotin, aptamers, peptides, insulin, EGF and transferrin.

2. The targeting ligand of claim 1, wherein the Targeting Moiety is a carbohydrate.

3. The targeting ligand of claim 1, wherein the targeting ligand is selected from the group consisting of:

135
(Structure 2)
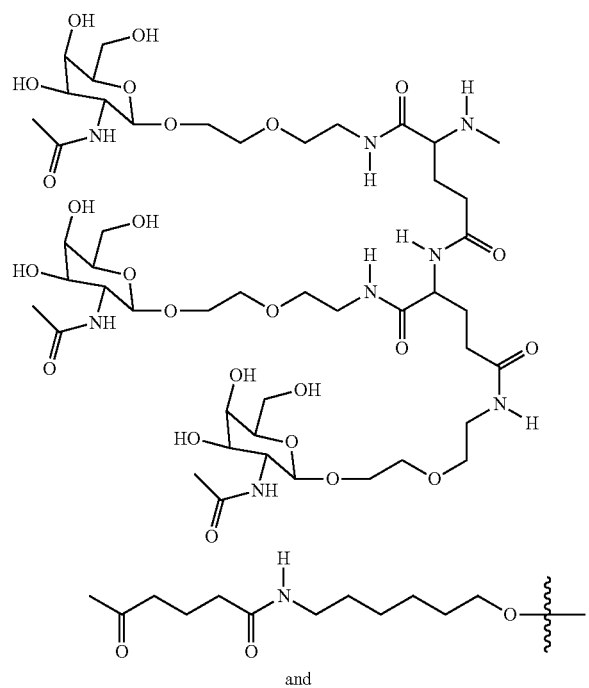
and
136
-continued
(Structure 6)
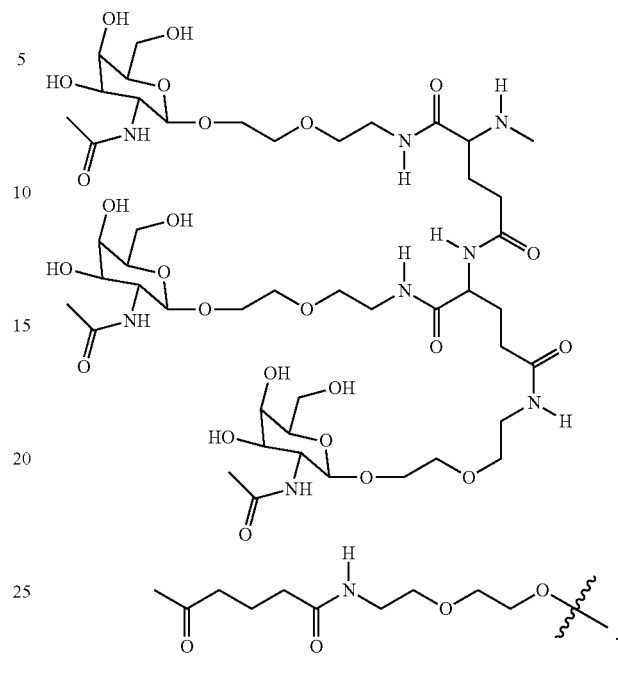
* * * * *

SEQUENCE LISTING

```
<160> NUMBER OF SEQ ID NOS: 27

<210> SEQ ID NO 1
<211> LENGTH: 26
<212> TYPE: RNA
<213> ORGANISM: artificial sequence
<220> FEATURE:
<223> OTHER INFORMATION: RNAi agent sense strand
<220> FEATURE:
<221> NAME/KEY: source
<223> OTHER INFORMATION: /note="Description of Combined DNA/RNA
```

Molecule"

<400> SEQUENCE: 1
uauaugccca agaaagugaa agacca                                          26

<210> SEQ ID NO 2
<211> LENGTH: 26
<212> TYPE: RNA
<213> ORGANISM: artificial sequence
<220> FEATURE:
<223> OTHER INFORMATION: RNAi agent sense strand

<400> SEQUENCE: 2
uauaugccca agaaagugaa agacca                                          26

<210> SEQ ID NO 3
<211> LENGTH: 26
<212> TYPE: RNA
<213> ORGANISM: artificial sequence
<220> FEATURE:
<223> OTHER INFORMATION: RNAi agent antisense strand

<400> SEQUENCE: 3
uggucuuuca cuuucuuggg cucuau                                          26

<210> SEQ ID NO 4
<211> LENGTH: 26
<212> TYPE: RNA
<213> ORGANISM: artificial sequence
<220> FEATURE:
<223> OTHER INFORMATION: RNAi agent sense strand
<220> FEATURE:
<221> NAME/KEY: source
<223> OTHER INFORMATION: /note="Description of Combined DNA/RNA
      Molecule"

<400> SEQUENCE: 4
uauaugccca agaaagugaa agacca                                          26

<210> SEQ ID NO 5
<211> LENGTH: 26
<212> TYPE: RNA
<213> ORGANISM: artificial sequence
<220> FEATURE:
<223> OTHER INFORMATION: RNAi agent antisense strand

<400> SEQUENCE: 5
uggucuuuca cuuucuuggg cucuau                                          26

<210> SEQ ID NO 6
<211> LENGTH: 26
<212> TYPE: RNA
<213> ORGANISM: artificial sequence
<220> FEATURE:
<223> OTHER INFORMATION: RNAi agent sense strand
<220> FEATURE:
<221> NAME/KEY: source
<223> OTHER INFORMATION: /note="Description of Combined DNA/RNA
      Molecule"

<400> SEQUENCE: 6
uauaugccca agaaagugaa agacca                                          26

<210> SEQ ID NO 7
<211> LENGTH: 26
<212> TYPE: RNA
<213> ORGANISM: artificial sequence

```
<220> FEATURE:
<223> OTHER INFORMATION: RNAi agent antisense strand

<400> SEQUENCE: 7 ugucuuuca cuuucuuggg cucuau                                    26

<210> SEQ ID NO 8
<211> LENGTH: 26
<212> TYPE: RNA
<213> ORGANISM: artificial sequence
<220> FEATURE:
<223> OTHER INFORMATION: RNAi agent sense strand

<400> SEQUENCE: 8
uauaugccca agaaagugaa agacca                                   26

<210> SEQ ID NO 9
<211> LENGTH: 26
<212> TYPE: RNA
<213> ORGANISM: artificial sequence
<220> FEATURE:
<223> OTHER INFORMATION: RNAi agent antisense strand

<400> SEQUENCE: 9 ugucuuuca cuuucuuggg cucuau                                    26

<210> SEQ ID NO 10
<211> LENGTH: 26
<212> TYPE: RNA
<213> ORGANISM: artificial sequence
<220> FEATURE:
<223> OTHER INFORMATION: RNAi agent sense strand

<400> SEQUENCE: 10
uauauaauua ucgaggcuca uucuca                                   26

<210> SEQ ID NO 11
<211> LENGTH: 26
<212> TYPE: RNA
<213> ORGANISM: artificial sequence
<220> FEATURE:
<223> OTHER INFORMATION: RNAi agent antisense strand

<400> SEQUENCE: 11
ugagaaugag ccucgauaau uauaua                                   26

<210> SEQ ID NO 12
<211> LENGTH: 26
<212> TYPE: RNA
<213> ORGANISM: artificial sequence
<220> FEATURE:
<223> OTHER INFORMATION: RNAi agent sense strand

<400> SEQUENCE: 12
uauauaauua ucgaggcuca uucuca                                   26

<210> SEQ ID NO 13
<211> LENGTH: 26
<212> TYPE: RNA
<213> ORGANISM: artificial sequence
<220> FEATURE:
<223> OTHER INFORMATION: RNAi agent antisense strand

<400> SEQUENCE: 13
ugagaaugag ccucgauaau uauaua                                   26
```

```
<210> SEQ ID NO 14
<211> LENGTH: 26
<212> TYPE: RNA
<213> ORGANISM: artificial sequence
<220> FEATURE:
<223> OTHER INFORMATION: RNAi agent sense strand
<220> FEATURE:
<221> NAME/KEY: source
<223> OTHER INFORMATION: /note="Description of Combined DNA/RNA
      Molecule"

<400> SEQUENCE: 14
uauauaguua ucgaggcuca uucuca                                              26

<210> SEQ ID NO 15
<211> LENGTH: 26
<212> TYPE: RNA
<213> ORGANISM: artificial sequence
<220> FEATURE:
<223> OTHER INFORMATION: RNAi agent antisense strand

<400> SEQUENCE: 15
ugagaaugag ccucgauaac ucuuau                                              26

<210> SEQ ID NO 16
<211> LENGTH: 26
<212> TYPE: RNA
<213> ORGANISM: artificial sequence
<220> FEATURE:
<223> OTHER INFORMATION: RNAi agent sense strand
<220> FEATURE:
<221> NAME/KEY: source
<223> OTHER INFORMATION: /note="Description of Combined DNA/RNA
      Molecule"

<400> SEQUENCE: 16
uauauaguua ucgaggcuca uucuca                                              26

<210> SEQ ID NO 17
<211> LENGTH: 26
<212> TYPE: RNA
<213> ORGANISM: artificial sequence
<220> FEATURE:
<223> OTHER INFORMATION: RNAi agent antisense strand

<400> SEQUENCE: 17
ugagaaugag ccucgauaac ucuuau                                              26

<210> SEQ ID NO 18
<211> LENGTH: 26
<212> TYPE: RNA
<213> ORGANISM: artificial sequence
<220> FEATURE:
<223> OTHER INFORMATION: RNAi agent sense strand
<220> FEATURE:
<221> NAME/KEY: source
<223> OTHER INFORMATION: /note="Description of Combined DNA/RNA
      Molecule"

<400> SEQUENCE: 18
uauauaguua ucgacgcuca uucuca                                              26

<210> SEQ ID NO 19
<211> LENGTH: 26
<212> TYPE: RNA
<213> ORGANISM: artificial sequence
<220> FEATURE:
<223> OTHER INFORMATION: RNAi agent antisense strand
```

```
<400> SEQUENCE: 19
ugagaaugag ccucgauaac ucuuau                                  26

<210> SEQ ID NO 20
<211> LENGTH: 26
<212> TYPE: RNA
<213> ORGANISM: artificial sequence
<220> FEATURE:
<223> OTHER INFORMATION: RNAi agent sense strand
<220> FEATURE:
<221> NAME/KEY: source
<223> OTHER INFORMATION: /note="Description of Combined DNA/RNA
      Molecule"

<400> SEQUENCE: 20
uauauaguua ucgaggcuca uucuca                                  26

<210> SEQ ID NO 21
<211> LENGTH: 26
<212> TYPE: RNA
<213> ORGANISM: artificial sequence
<220> FEATURE:
<223> OTHER INFORMATION: RNAi agent antisense strand

<400> SEQUENCE: 21
ugagaaugag ccucgauaac ucuuau                                  26

<210> SEQ ID NO 22
<211> LENGTH: 26
<212> TYPE: RNA
<213> ORGANISM: artificial sequence
<220> FEATURE:
<223> OTHER INFORMATION: RNAi agent sense strand
<220> FEATURE:
<221> NAME/KEY: source
<223> OTHER INFORMATION: /note="Description of Combined DNA/RNA
      Molecule"

<400> SEQUENCE: 22
uauaugccca agaaagugaa agacca                                  26

<210> SEQ ID NO 23
<211> LENGTH: 26
<212> TYPE: RNA
<213> ORGANISM: artificial sequence
<220> FEATURE:
<223> OTHER INFORMATION: RNAi agent antisense strand

<400> SEQUENCE: 23
uggucuuuca cuuucuuggg cucuau                                  26

<210> SEQ ID NO 24
<211> LENGTH: 21
<212> TYPE: RNA
<213> ORGANISM: artificial sequence
<220> FEATURE:
<223> OTHER INFORMATION: RNAi agent sense strand

<400> SEQUENCE: 24
cgauaucauc accaaguucc a                                       21

<210> SEQ ID NO 25
<211> LENGTH: 21
<212> TYPE: RNA
<213> ORGANISM: artificial sequence
<220> FEATURE:
```

```
<223> OTHER INFORMATION: RNAi agent antisense strand

<400> SEQUENCE: 25
uggaacuugg ugaugauauc g                                    21

<210> SEQ ID NO 26
<211> LENGTH: 26
<212> TYPE: RNA
<213> ORGANISM: artificial sequence
<220> FEATURE:
<223> OTHER INFORMATION: RNAi agent sense strand
<220> FEATURE:
<221> NAME/KEY: source
<223> OTHER INFORMATION: /note="Description of Combined DNA/RNA
      Molecule"

<400> SEQUENCE: 26
gcgaugccca agaaagugaa agacca                               26

<210> SEQ ID NO 27
<211> LENGTH: 26
<212> TYPE: RNA
<213> ORGANISM: artificial sequence
<220> FEATURE:
<223> OTHER INFORMATION: RNAi agent antisense strand

<400> SEQUENCE: 27
uggucuuuca cuuucuuggg caucgc                               26
```